(12) United States Patent
Nahmias et al.

(10) Patent No.: US 10,772,863 B2
(45) Date of Patent: Sep. 15, 2020

(54) METHODS OF INDUCING METABOLIC MATURATION OF HUMAN PLURIPOTENT STEM CELLS— DERIVED HEPATOCYTES

(71) Applicant: Yissum Research Development Company of the Hebrew University of Jerusalem Ltd., Jerusalem (IL)

(72) Inventors: Yaakov Nahmias, Rishon-LeZion (IL); Michal Zimerman, Caesarea (IL); Gahl Levy, Ramat-Gan (IL); Yishai Avior, Rosh HaAyin (IL)

(73) Assignee: Yissum Research Development Company of the Hebrew University of Jerusalem Ltd, Jerusalem (IL)

( * ) Notice: Subject to any disclaimer, the term of this patent is extended or adjusted under 35 U.S.C. 154(b) by 0 days.

(21) Appl. No.: 15/459,139

(22) Filed: Mar. 15, 2017

(65) Prior Publication Data

US 2017/0266145 A1 Sep. 21, 2017

Related U.S. Application Data

(60) Provisional application No. 62/308,372, filed on Mar. 15, 2016.

(51) Int. Cl.
*A61K 31/201* (2006.01)

(52) U.S. Cl.
CPC .................................. *A61K 31/201* (2013.01)

(58) Field of Classification Search
CPC ..................................................... A61K 31/201
See application file for complete search history.

(56) References Cited

U.S. PATENT DOCUMENTS

2007/0213282 A1    9/2007 Sasaki et al.

OTHER PUBLICATIONS

Turpeinen et al., Effects of cis-9, trans-11 CLA in Rats at intake levels Reported for Breast-fed Infants, 2006, Lipids, vol. 41, No. 7, pp. 669-677 (Year: 2006).*
Roelandt et al., Human Embryonic and Rat Adult Stem Cells with Primitive Endoderm-Like Phenotype Can Be Fated to Definitive Endoderm, and Finally Hepatocyte-Like Cells, 2010. PLoS One, vol. 5, Iss.8, e12101, pp. 1-11 (Year: 2010).*
Chen et al. "Disruption of Fusion Results in Mitochondrial Heterogeneity and Dysfunction", The Journal of Biological Chemistry, 280(28): 26185-26192, Jul. 15, 2005.
Halade et al. "Differential Effects of Conjugated Linoleic Acid Isomers in Insulin- Resistant Female C57Bl/6J Mice", Journal of Nutritional Biochemistry, 21(4): 332-337, Published Online May 9, 2009.
Halade et al. "Effect of CLA Isomers and Their Mixture on Aging C57Bl/6J Mice", European Journal of Nutrition, 48(7): 409-418, Published Online May 8, 2009.
Lue et al. "Transdifferentiation of Adipose-Derived Stem Cells Into Hepatocytes: A New Approach", Liver International, 30(6): 913-922, Published Online Mar. 26, 2010.
Moya-Camarena et al. "Conjugated Linoleic Acid Activates Peroxisome Proliferator-Activated Receptor Alpha and Beta Subtypes But Does Not Induce Hepatic Peroxisome Proliferation in Sprague-Dawley Rats", Biochimica et Biophysica Acta, 1436(3): 331-342, Jan. 4, 1999.
Nahmias et al. "Integration of Technologies for Hepatic Tissue Engineering", Advances in Biochemical Engineering/ Biotechnology, 103: 309-329, Published Online Sep. 12, 2006.
Postler "Conductance of Concentrated Aqueous Solutions of Electrolytes II. Strong Polyvalent Electrolytes", Collection of Czechoslovak Chemical Communications, 35(8):2244-2249, 1970.
Reynolds et al. "Conjugated Linoleic Acid and Inflammatory Cell Signalling", Prostaglandins, Leukotrienes and Essential Fatty Acids, 82(4): 199-204, Published Online Mar. 7, 2010.
Roelandt et al. "Directed Differentiation of Pluripotent Stem Cells to Functional Hepatocytes", Pluripotent Stem Cells: Methods and Protocols, Methods in Molecular Biology, 997(Chap.11): 141-147, 2013.
Stock et al. "The Generation of Hepatocytes From Mesenchymal Stem Cells and Engraftment Into Murine Liver", Nature Protocols, 5(4): 617-627, Published Online Mar. 11, 2010.
Chen et al. "Enhancement of Hepatocyte Differentiation From Human Embryonic Stem Cells by Chinese Medicine Fuzhenghuayu", Scientific Reports, 6(18841): 1-13, Jan. 6, 2016.
Chen et al. "Liver X Receptor Alpha (LXR Alpha/NR1H3) Regulates Differentiation of Hepatocyte-Like Cells Via Reciprocal Regulation of HNF4Alpha", Journal of Hepatology, 61(6): 1276-1286, Dec. 31, 2014.
Chen et al. "Rapid Generation of Mature Hepatocyte-Like Cells From Human Induced Pluripotent Stem Cells by an Efficient Three-Step Protocol", Hepatology, 55(4): 1193-1203, Published Online Mar. 1, 2012.
Choi et al. "Effects of Three Different Conjugated Linoleic Acid Preparations on Insulin Signalling, Fat Oxidation and Mitochondrial Function in Rats Fed a High-Fat Diet", British Journal of Nutrition, 98(2): 264-275, Published Online Apr. 4, 2007.
Duan et al. "Differentiation and Characterization of Metabollically Functioning Hepatocytes From Human Embryonic Stem Cells", Stem Cells, 28(4): 674-686, Published Online Feb. 4, 2010.

(Continued)

*Primary Examiner* — Kortney L. Klinkel
*Assistant Examiner* — Tori Strong
(74) *Attorney, Agent, or Firm* — Kathleen D. Rigaut; Howson & Howson LLP

(57) ABSTRACT

Provided are methods of increasing metabolic maturation of an immature hepatocyte, by contacting an immature hepatocyte which expresses alpha-fetoprotein (AFP) and albumin with an effective amount of a fatty acid or a small molecule selected from the group consisting of: an amphipathic carboxylic acid, Thiazolidinedione (TZD), WY-14643 (Pirinixic Acid), GW409544, GW6471, Leukotriene B4, GW 7647, Perfluorooctanesulfonic Acid, Perfluorooctanoic Acid, CP-775146, CP-865520, UNII-999KY5ZIGB, and Gemfibrozil. Also provided are isolated hepatocytes and uses thereof.

15 Claims, 11 Drawing Sheets
(11 of 11 Drawing Sheet(s) Filed in Color)

Specification includes a Sequence Listing.

(56) References Cited

OTHER PUBLICATIONS

Esmaeli et al. "The Role of Albumin and PPAR-Alpha in Differentiation-Dependent Change of Fatty Acid Profile During Differentiation of Mesenchymal Stem Cells to Hepatocyte-Like Cells", Cell Biochemistry & Function, 32(5): 410-419, Published Online Mar. 3, 2014.
Gruppuso et al. "Identification of Candidate Growth-Regulating Genes That Are Overexpressed in Late Gestation Fetal Liver in the Rat", Biochimica et Biophysica Acta, 1494(3): 242-247, Dec. 1, 2000.
Inamura et al. "Efficient Generation of Hepatoblasts From Human ES Cells and iPS Cells by Transient Overexpression of Homeobox Gene HEX", Molecular Therapy, 19(2): 400-407, Published Online Nov. 23, 2010.
Kamiya et al. "Oncostatin M and Hepatocyte Growth Factor Induce Hepatic Maturation Via Distinct Signaling Pathways", FEBS Letters, 492(1-2): 90-94, Published Online Feb. 21, 2001.
Khetani et al. "Microscale Culture of Human Liver Cells for Drug Development", Nature Biotechnology, 26(1): 120-126 & Suppl. Information, Published Online Nov. 18, 2007.
Kidambi et al. "Oxygen-Mediated Enhancement of Primary Hepatocyte Metabolism, Functional Polarization, Gene Expression, and Drug Clearance", Proc. Natl. Acad. Sci. USA, PNAS, 106(37): 15714-15719, Sep. 15, 2009.
Parmentier et al. "Regulation of CYP4A1 and Peroxisome Proliferator-Activated Receptor Alpha Expression by Interleukin-1Beta, Interleukin-6, and Dexamethasone in Cultures Fetal Rat Hepatocytes", Biochemical Pharmacology, 54(8): 889-898, Oct. 15, 1997.
Poirier et al. "Nutritional Supplementation With Trans-10, Cis-12—Conjugated Linoleic Acid Induces Inflammation of White Adipose Tissue", Diabetes, 55(6): 1634-1641, Jun. 2006.
Schwartz et al. "Multipotent Adult Progenitor Cells From Bone Marrow Differentiate Into Functional Hepatocyte-Like Cells", The Journal of Clinical Investigation, 109(10): 1291-1302, May 2002.
Shan et al. "Identifiaction of Small Molecules for Human Hepatocyte Expansion and iPS Differentiation", Nature Chemical Biology, 9(8): 514-521, Published Online Jun. 2, 2013 & Supplementary Information.
Shulman et al. "Long-Term Culture and Coculture of Primary Rat and Human Hepatocytes", Methods in Molecular Biology, 945: 287-302, Sep. 24, 2013.
Si-Tayeb et al. "Highly Efficient Generation of Human Hepatocyte-Like Cells From Induced Pluripotent Stem Cells", Hepatology, 51(1): 297-305, Jan. 2010.
Song et al. "Efficient Generation of Hepatocyte-Like Cells From Human Induced Pluripotent Stem Cells", Cell Research, 19(11): 1233-1242, Published Online Sep. 8, 2009 & Supplementary Material.
Staudinger et al. "The Nuclear Receptor PXR Is a Lithocholic Acid Sensor That Protects Against Liver Toxicity", Proc. Natl. Acad. Sci. USA, PNAS, 98(6): 3369-3374, Mar. 13, 2001.
Stier et al. "Maturation of Peroxisomes in Differentiating Human Hepatoblastoma Cells (HepG2): Possible Involvement of the Peroxisome Proliferator-Activated Receptor Alpha (PPARAlpha)", Differentiation, 64(1): 55-66, Nov. 1998.
Sullivan et al. "Generation of Functional Human Hepatic Endoderm From Human iPS Cells", Hepatology, 51(1): 329-335, Jan. 2010.
Szkolnicka et al. "Accurate Prediction of Drug-Induced Liver Injury Using Stem Cell-Derived Populations", Stem Cells Translational Medicine, 3(2): 141-148, Published Online Dec. 27, 2013.
Tashiro et al. "Efficient Adipocyte and Osteoblast Differentiation From Mouse Induced Pluripotent Stem Cells by Adenoviral Transduction", Stem Cells, 27(8): 1802-1811, Published Online Apr. 30, 2009.
Wanet et al. "Mitochondrial Remodeling in Hepatic Differentiation and Dedifferentiation", The International Journal of Biochemistry & Cell Biology, 54: 174-185, Published Online Jul. 30, 2014.
Yu et al. "Hepatocyte-Like Cells Differentiated From Human Induced Pluripotent Stem Cells: Relevance to Cellular Therapies", Stem Cell Research, 9(3): 196-207, Available Online Jun. 28, 2012.
Zhu et al. "Mouse Liver Repopulation With Hepatocytes Generated From Human Fibroblasts", Nature, 508(7494): 93-97, Apr. 3, 2014.

\* cited by examiner

Fig. 1A
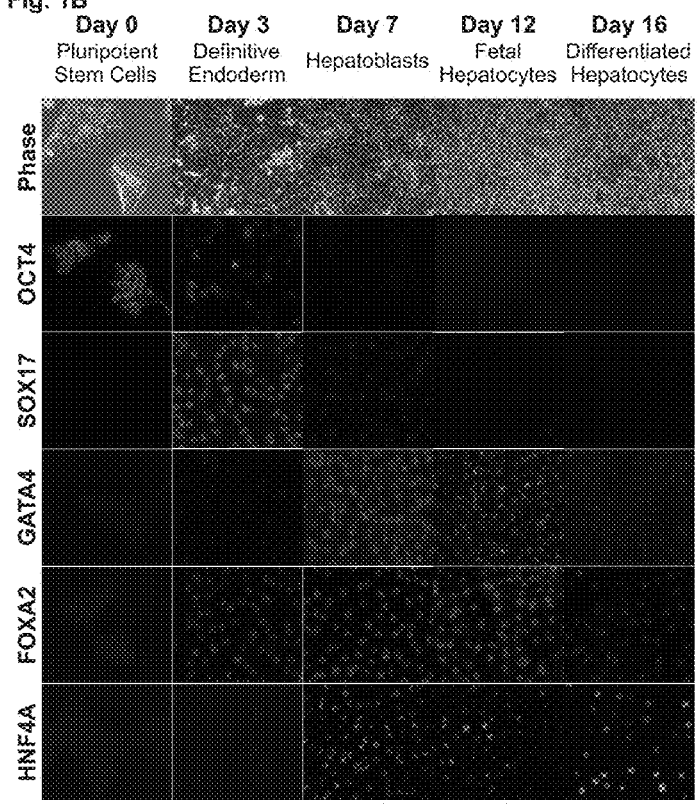
Fig. 1B
Day 0 — Pluripotent Stem Cells
Day 3 — Definitive Endoderm
Day 7 — Hepatoblasts
Day 12 — Fetal Hepatocytes
Day 16 — Differentiated Hepatocytes
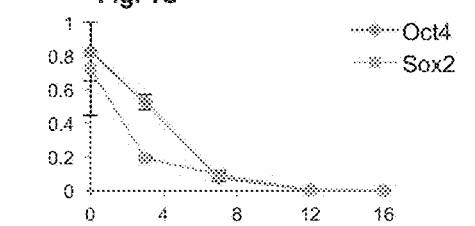
Fig. 1C
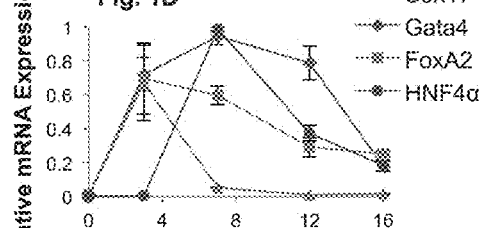
Fig. 1D
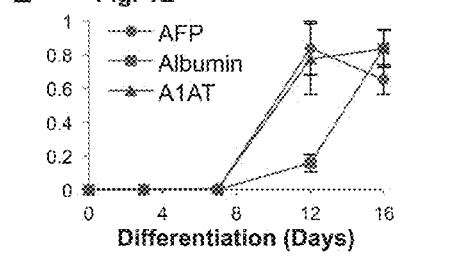
Fig. 1E
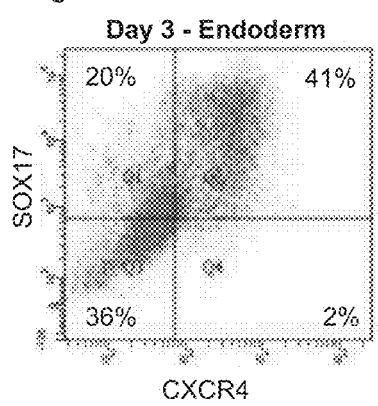
Fig. 1F — Day 3 - Endoderm
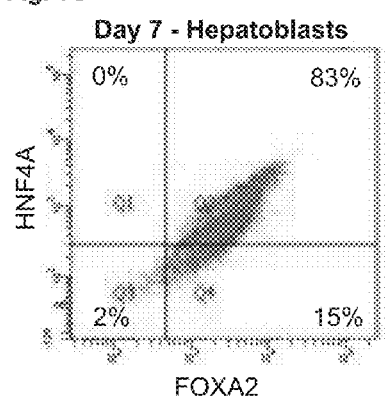
Fig. 1G — Day 7 - Hepatoblasts
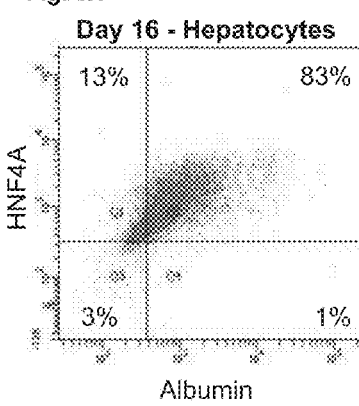
Fig. 1H — Day 16 - Hepatocytes

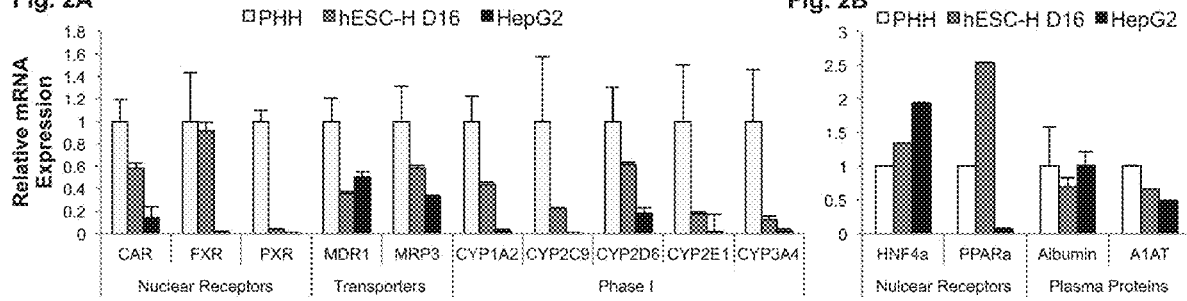
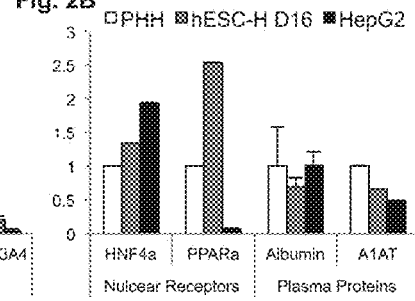
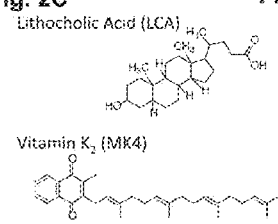
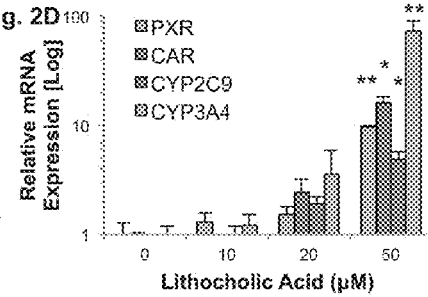
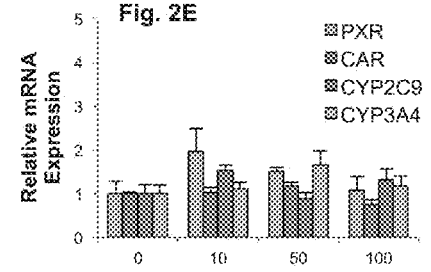
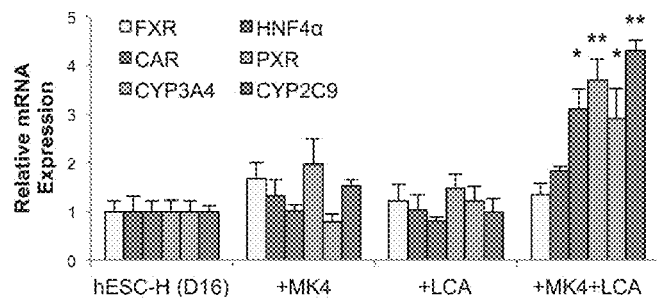
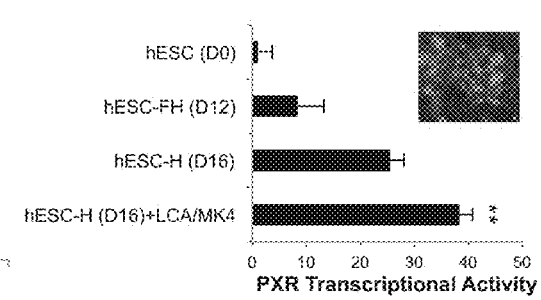
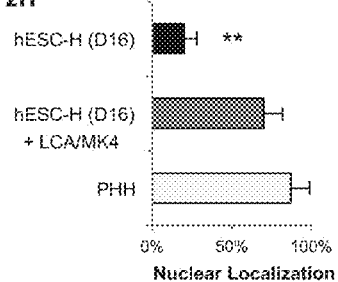
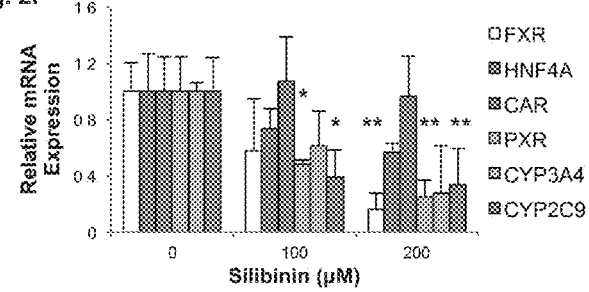

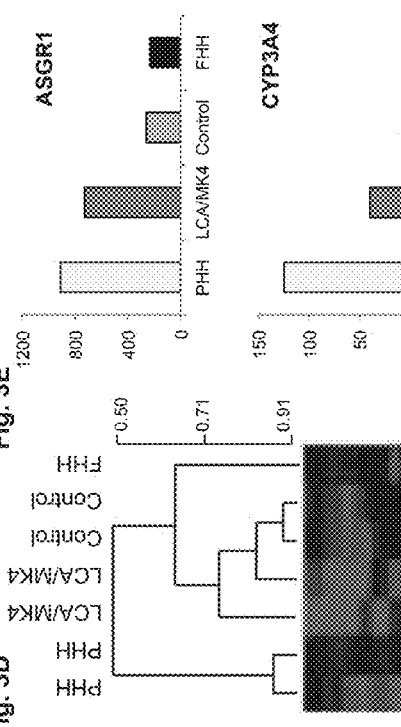
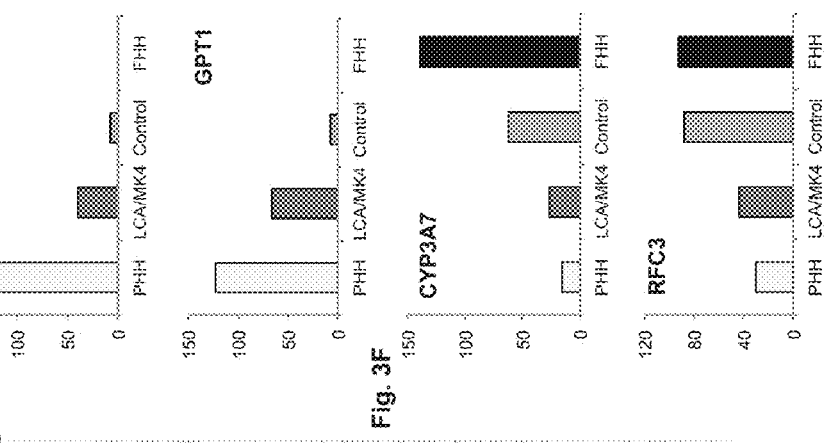
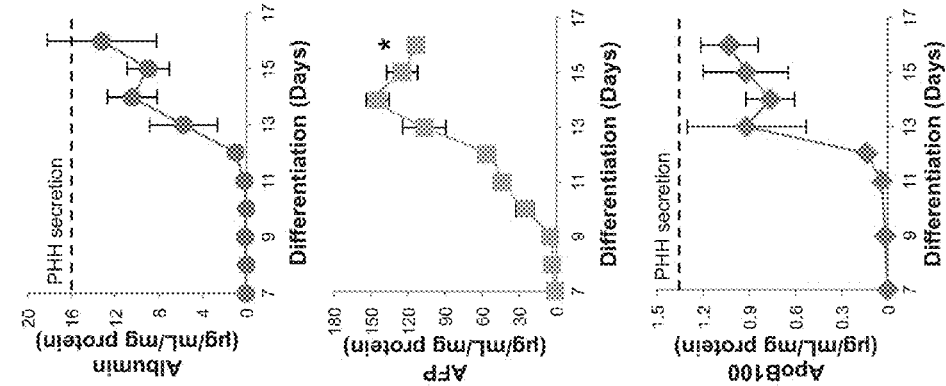
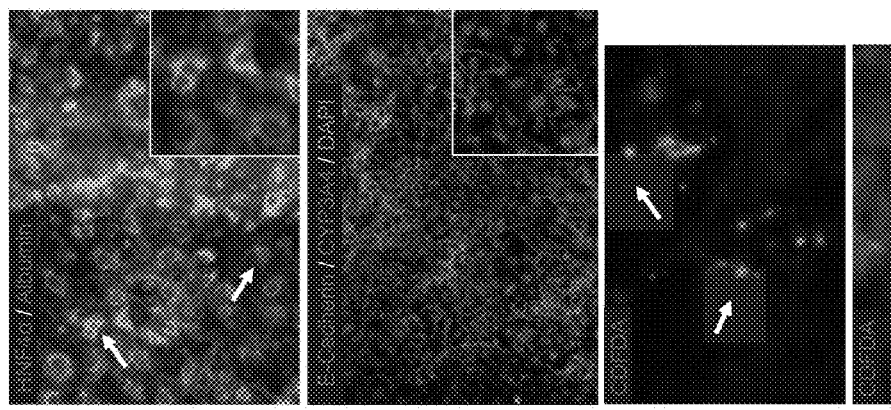
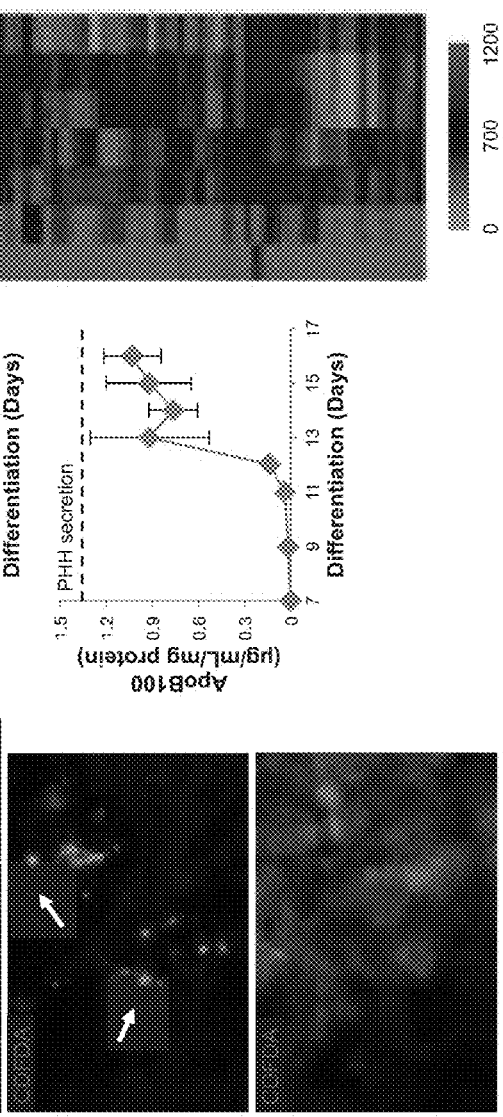

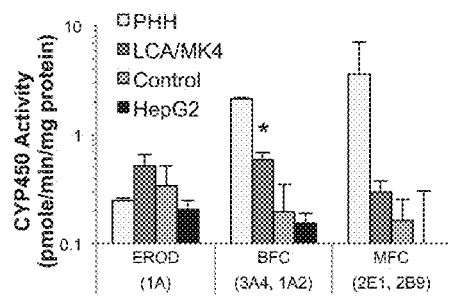
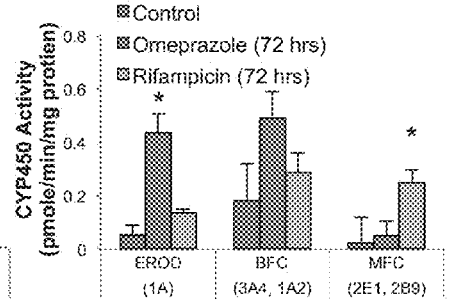
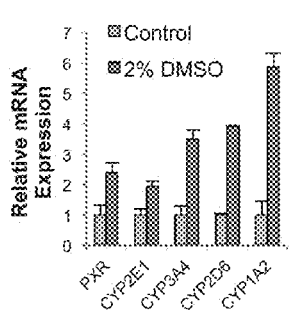
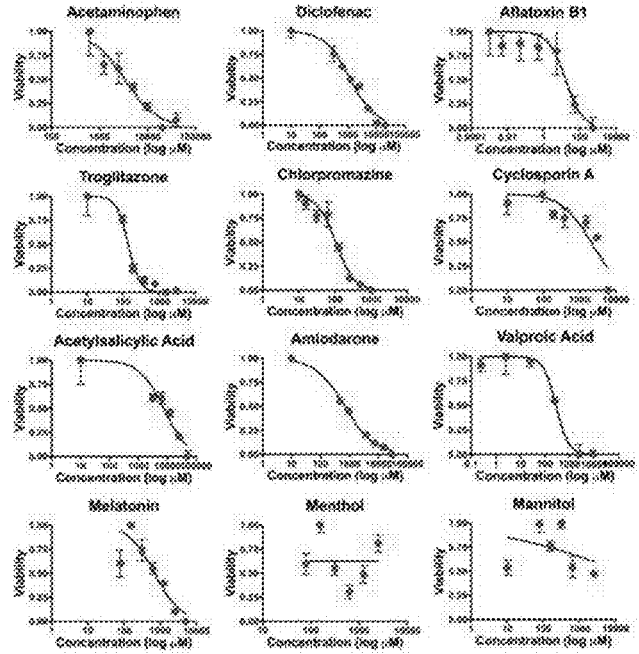
| Toxin | TC$_{50}$ Value (µM) | |
|---|---|---|
| | LCA/MK4 | Control |
| Acetaminophen | 3366±547 | 2061±2150 |
| Diclofenac | 1161±144 | 3241±313 |
| Aflatoxin B1 | 16±7 | 34±27 |
| Troglitazone | 136±9 | 926±141 |
| Chlorpromazine | 104±11 | 1576±27 |
| Acetylsalicylic Acid | 7424±1539 | 6155±1020 |
| Amiodarone | 686±57 | 2060±690 |
| Valproic Acid | 269±113 | 1481±197 |
| Melatonin | 699±223 | 1007±585 |
| Menthol | N.A. | N.A. |
| Mannitol | N.A. | N.A. |
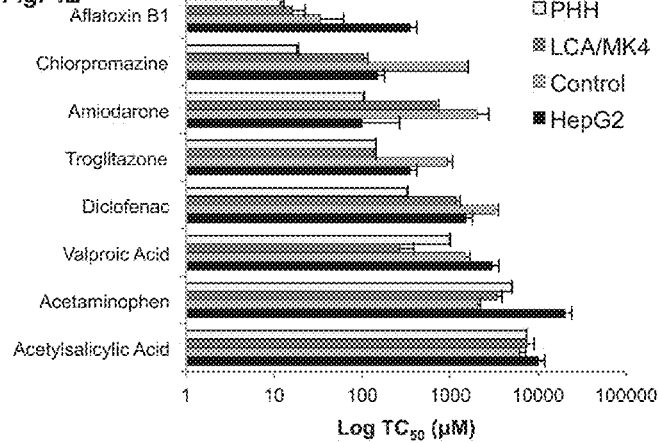
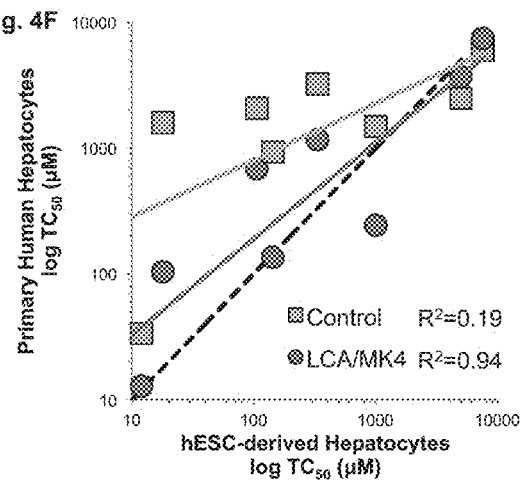

Fig. 5A
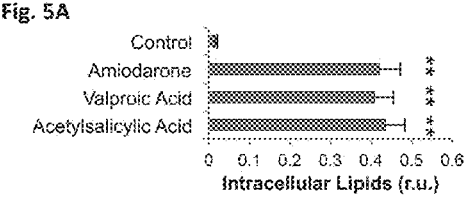
Fig. 5B LipidTOX™ / Hoechst
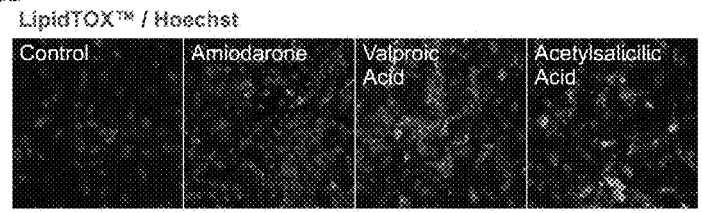
Fig. 5C
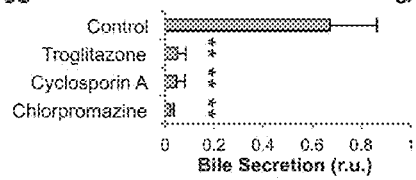
Fig. 5D CDFDA / Hoechst
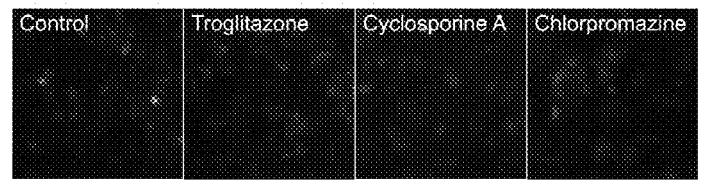
Fig. 5E
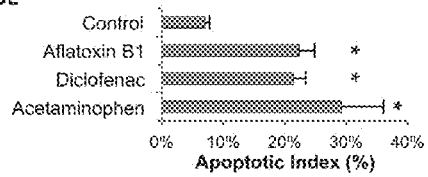
Fig. 5F TUNEL / Hoechst
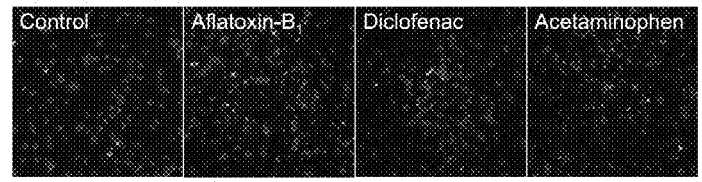
Fig. 5G
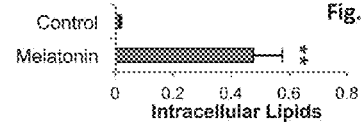
Fig. 5I LipidTOX™ / Hoechst    CDFDA / Hoechst
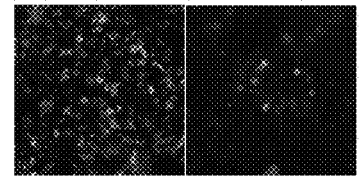
Fig. 5H
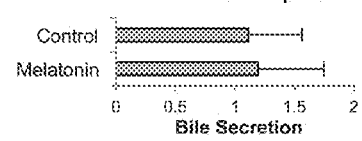

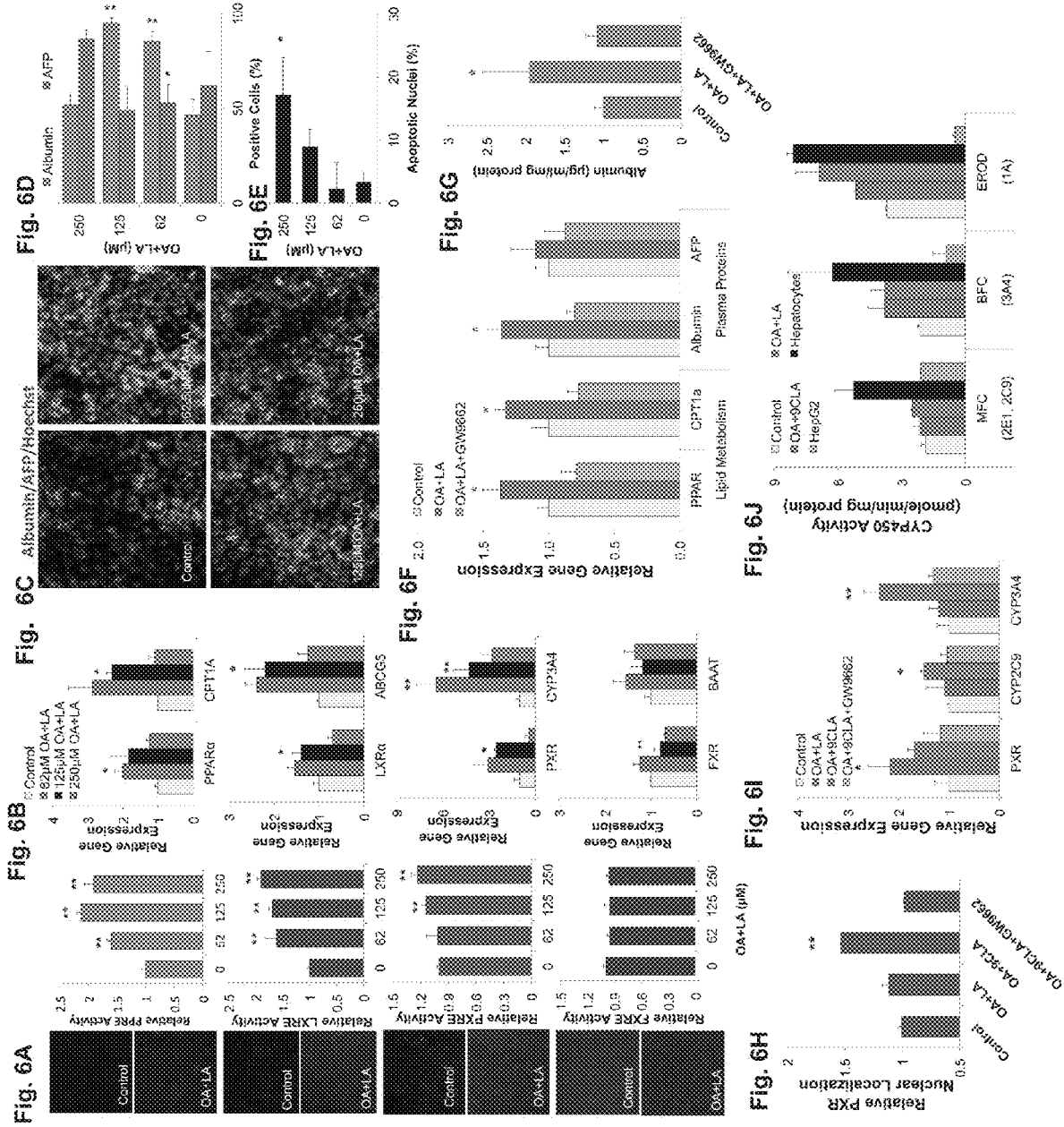

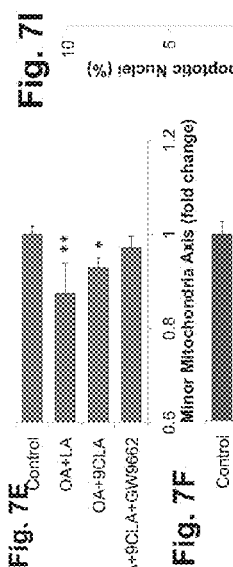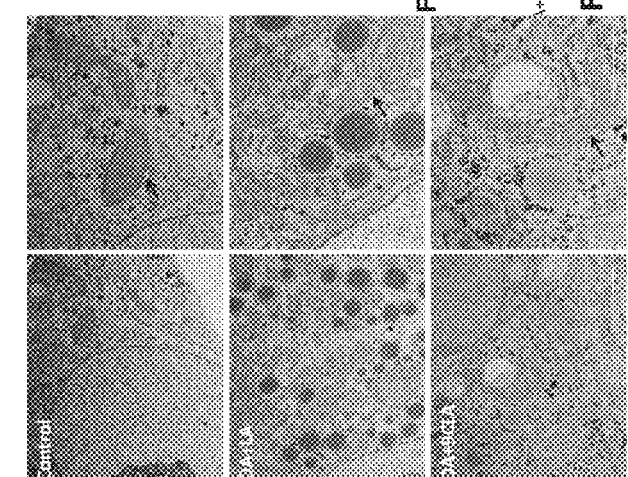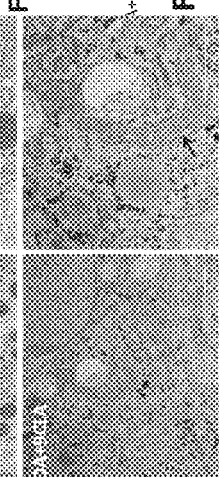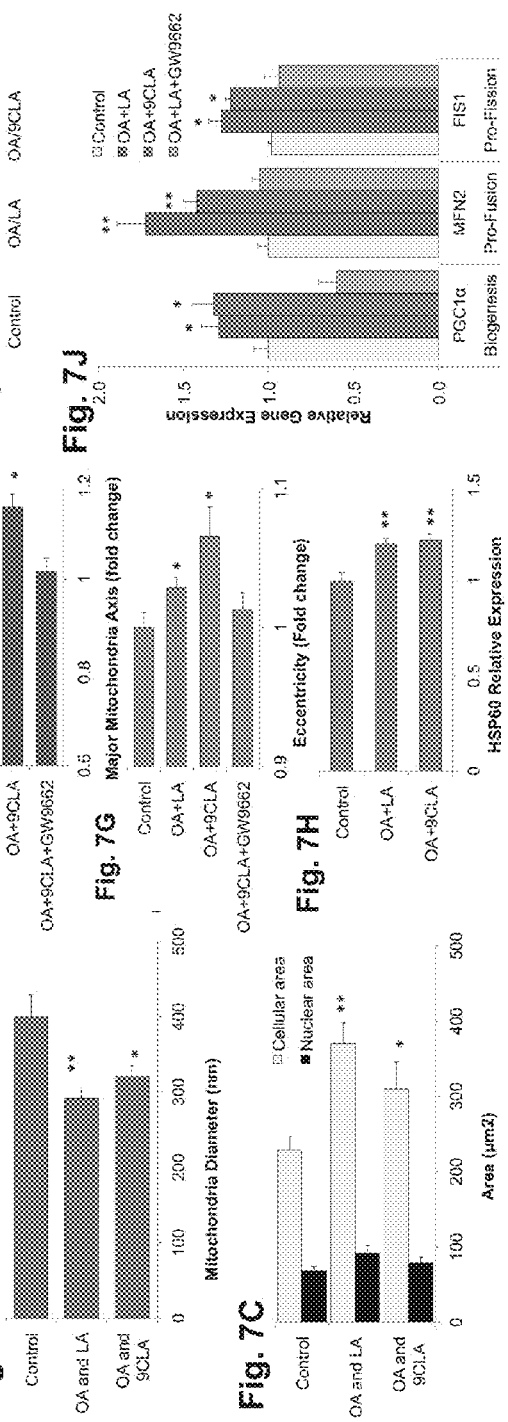

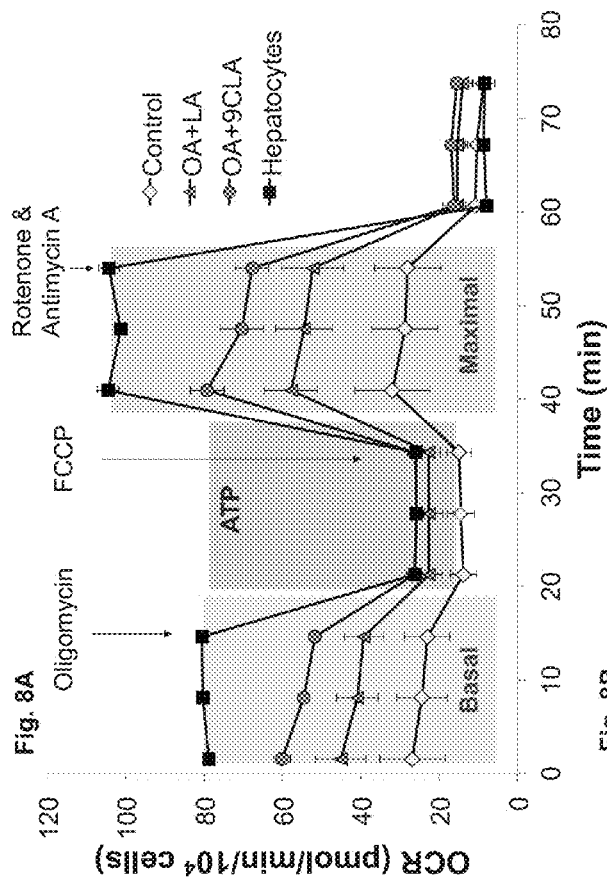
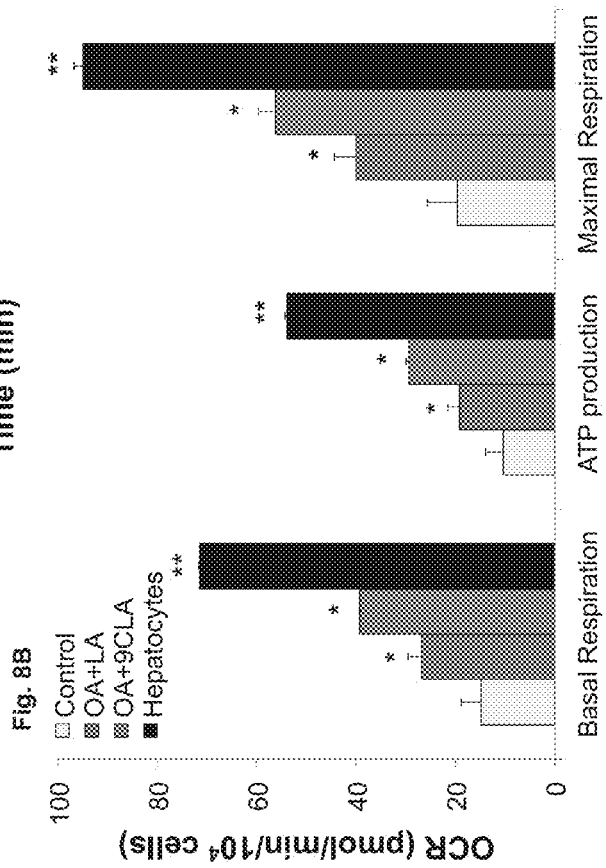

METHODS OF INDUCING METABOLIC MATURATION OF HUMAN PLURIPOTENT STEM CELLS— DERIVED HEPATOCYTES

RELATED APPLICATION

This application claims the benefit of priority under 35 USC 119(e) of U.S. Provisional Patent Application No. 62/308,372 filed on Mar. 15, 2016, the contents of which are incorporated herein by reference in their entirety.

The work leading to this invention has received funding from the European Research Council under the European Union's Seventh Framework Programme (FP7/2007-2013)/ERC grant agreement no. [248417].

SEQUENCE LISTING STATEMENT

The ASCII file, entitled 69429SequenceListing.txt, created on Mar. 15, 2017, comprising 169,445 bytes, submitted concurrently with the filing of this application is incorporated herein by reference.

FIELD AND BACKGROUND OF THE INVENTION

The present invention, in some embodiments thereof, relates to methods of increasing metabolic maturation of immature hepatocytes and isolated hepatocytes resulting thereof.

The liver is the largest internal organ in the human body, and is responsible for protein synthesis as well as glucose, lipid and nitrogen homeostasis. Transformation of lipid metabolites is primarily carried out by the cytochrome P450 (CYP450) family of monooxygenases, which is also responsible for the transformation of most xenobiotics, often as a first step for conjugation and secretion of water-soluble metabolites (Guengerich 2007). Due to these metabolic functions the organ is particularly sensitive to drug-induced liver injury (DILI), a leading cause of acute liver failure and post-market drug withdrawals (Kaplowitz 2005). Liver toxicity and drug metabolism are therefore a major focus of pharmaceutical and cosmetic industry compound development.

The low concordance between animal studies and clinical data (Olson, Betton et al. 2000, Gottmann, Kramer et al. 2001) and the low metabolic activity of hepatic cell lines necessitates the use of primary human hepatocytes for drug metabolism and toxicity studies (LeCluyse 2001). However, primary human hepatocytes are scarce, do not proliferate and rapidly lose their metabolic functions in vitro (Guillouzo 1998, Hewitt, Lechon et al. 2007). The recent development of micro-fabricated or oxygenated co-cultures was shown to support primary cell activity for several weeks in culture (Nahmias, Berthiaume et al. 2007, Khetani and Bhatia 2008, Kidambi, Yarmush et al. 2009, Shulman and Nahmias 2013), but did little to attenuate the need for functional cells. It is the scarcity in primary human hepatocytes that drives the current focus in hepatic cell differentiation. Although a few cell types can be coaxed into hepatic like cells (Schwartz, Reyes et al. 2002, Lue, Lin et al. 2010, Stock, Bruckner et al. 2010, Zhu, Rezvani et al. 2014), it is thought that only pluripotent stem cells (PSC) may provide the full gamete of mature hepatic function (Duan, Ma et al. 2010).

Indeed, several groups already reported the differentiation of hepatocyte-like cells from embryonic or induced pluripotent stem cells (Song, Cal et al. 2009, Duan, Ma et al. 2010, Si-Tayeb, Noto et al. 2010, Chen, Tseng et al. 2012, Roelandt, Vanhove et al. 2013, Shan et al. 2013, Chen et al. 2015). While these groups focused on albumin production, hepatocyte-like cells still display fetal markers such as α-fetoprotein (AFP) and lack the inducibility and function of most mature CYP450 enzymes, such as CYP3A4. In fact, recent attempts to use hPSC-derived hepatocytes in drug toxicity screening garnered a poor correlation with primary human hepatocytes, showing an $R^2$ of 0.49 (Szkolnicka, Farnworth et al. 2014). Interestingly, fetal markers such as AFP and CYP3A7 were shown to decrease only after birth, with a gradual increase in CYP3A4 expression taking place only during the first year of life (Lacroix, Sonnier et al. 1997, Guengerich 2007). These in vivo results suggest that postpartum cues may drive the final maturation step of liver cells.

Postnatal maturation of mitochondria is another key limiting factor in the derivation of functional hepatocytes. Fetal hepatocytes rely on placenta-transferred carbohydrates and anaerobic glycolysis (Hommes, 1973; Hommes, 1975), while postnatal functional and structural maturation of over 1400 mitochondria in liver cells enables much higher metabolic rates (Pollak, 1980).

Therefore, recently, mitochondrial biogenesis and metabolism emerged as important factors in evaluating hepatic maturity and functionality in vitro (Yue Yu, 2012; Anais Waneta, 2014).

The liver microenvironment changes significantly by the transition from placental to enteral nutrition (Morelli 2008). Fatty acids from breastfeeding become the primary energy source, while gut colonization exposes the liver to bacterial-derived secondary metabolites, such as litocholic acid (LCA) and menaquinone-4 (MK4). LCA is a secondary bile acid, produced by intestinal bacteria, and shown to activate the pregnane X receptor (PXR), a nuclear receptor controlling the expression of CYP450 enzymes such as CYP2C9 and CYP3A4 (Staudinger, Goodwin et al. 2001). Vitamin K is a group of essential fat-soluble vitamins, whose active metabolite MK4 (vitamin $K_2$) is synthesized by colon bacteria (Conly and Stein 1992).

Prenatal levels of vitamin K are low due to poor placental travel (Shearer, Rahim et al. 1982), and it is regularly administered to newborns immediately after birth to prevent vitamin K deficiency that leads to fatal bleeding (Shearer 2009). MK4 was also shown to activate PXR, primarily in bone cells (Tabb, Sun et al. 2003, Ichikawa, Horie-Inoue et al. 2006).

Intestinal microbial colonization in newborns is also influenced by the lipid rich diet (Morelli, 2008; DA, 2014). *Bifidobacterium* and *lactobacillus* thrive on breast milk glycans and lactate, respectively, thus becoming predominant during the lactation period (Conway, 1997; Haarman, 2005; Haarman, 2006; Sela, 2014). Both strains metabolize one of the main unsaturated fatty acid in the human breast milk, linoleic acid (LA) (Finley, 1985, Supplement table 1), to conjugated linoleic acid (CLA), mainly to cis-9,trans-11-octadecadienoic acid 18:2 (9CLA), which is known for its bioactive properties (Halade, 2009; Halade, 2010; Poirier, 2006; Reynolds, 2010; Choi, 2007). 9CLA enhances hepatic mitochondrial function in rats (Choi, 2007) and acts as a high affinity ligand of Peroxisome proliferator-activated receptor, isoform a (PPARα) (Moya-Camarena, 1999). PPARα is a lipid activated nuclear receptor whose expression and activity increase significantly during the suckling period (Beck, 1992; Panadero, 2000).

Additional background art includes U.S. Patent Application Publication US 20070213282 A1 [Peroxisome proliferator-activated receptor (PPAR) activator, and drugs, supplements, functional foods and food additives using the same]; Tashiro K., et al., 2009 (Stem Cells 27: 1802-1811); Inamura M et al. 2011 (Mol. Therapy, 19:400-407); Sullivan G J., et al. 2011 (Hepatology 51: 329-335); Si-Tayeb K., et al., 2010 (Hepatology 51: 297-305); Song Z., et al. 2009 (Cell Research 19: 1233-1242); Shan J., et al., 2013 (Nature Chemical Biology 9: 514-521); Kai-Ting Chen et al., 2014 (Journal of Hepatology, Elsevier, 2014, 61 (6), pp. 1276-1286); Parmentier J H 1997 (Biochemical Pharmacology 54: 889-898); Gruppuso P A., et al. 2000 (Biochimica et Biophysica Acta 1494:242-247); Esmaeli S., et al. 2014 (Cell Biochemistry and Function 32: 410-419); Chen J., et al., 2016 (Scientific Reports 6: 18841 DOI: 10.1038/srep18841); Stier H., et al., 1998 (Differentiation 64: 55-66).

SUMMARY OF THE INVENTION

According to an aspect of some embodiments of the present invention there is provided a method of increasing metabolic maturation of an immature hepatocyte, the method comprising contacting an immature hepatocyte which expresses alpha-fetoprotein (AFP) and albumin with an effective amount of a fatty acid or a small molecule selected from the group consisting of: an amphipathic carboxylic acid, Thiazolidinedione (TZD), WY-14643 (Pirinixic Acid), GW409544, GW6471, Leukotriene B4, GW 7647, Perfluorooctanesulfonic Acid, PERFLUOROOCTANOIC ACID, CP-775146, CP-865520, UNII-999KY5ZIGB, and Gemfibrozil, thereby increasing the metabolic maturation of the immature hepatocyte.

According to an aspect of some embodiments of the present invention there is provided a method of treating a subject diagnosed with a pathology characterized by immature hepatocytes, the method comprising administering to the subject an effective amount of a fatty acid or a small molecule selected from the group consisting of: an amphipathic carboxylic acid, Thiazolidinedione (TZD), WY-14643 (Pirinixic Acid), GW409544, GW6471, Leukotriene B4, GW 7647, Perfluorooctanesulfonic Acid, PERFLUOROOCTANOIC ACID, CP-775146, CP-865520, UNII-999KY5ZIGB, and Gemfibrozil, thereby increasing the metabolic maturation of the immature hepatocytes and treating the subject.

According to an aspect of some embodiments of the present invention there is provided a method of increasing metabolic maturation of an immature hepatocyte, the method comprising contacting an immature hepatocyte which expresses alpha-fetoprotein (AFP) and albumin with a medium being devoid of an IL6 ligand and which comprises an effective amount of a PXR agonist selected from the group consisting of: a small molecule, a bile acid, and a steroid, thereby increasing the metabolic maturation of the immature hepatocyte, wherein said effective amount of said PXR agonist increases the expression of a PXR target gene selected from the group consisting of: CYP3A4 and CYP2C9 by at least 2-folds.

According to an aspect of some embodiments of the present invention there is provided a method of treating a subject diagnosed with a pathology characterized by immature hepatocytes, the method comprising administering to the subject a pharmaceutical composition comprising an effective amount of a PXR agonist selected from the group consisting of: a small molecule, a bile acid, and a steroid, wherein said pharmaceutical composition is devoid of an IL6 ligand, wherein said effective amount of said PXR agonist increases the expression of a PXR target gene selected from the group consisting of: CYP3A4 and CYP2C9 by at least 2-folds, thereby increasing the metabolic maturation of said immature hepatocytes and treating the subject.

According to an aspect of some embodiments of the present invention there is provided an isolated hepatocyte characterized by a Cytochrome P450 3A4 (CYP3A4) activity which is capable of oxidizing at least 1 pmol of 7-benzyloxy-4-trifluoromethylcoumarin (BFC) per minute per milligram of cellular protein and an alpha feto-protein (AFP) activity of at least 60 µg/day/mg cellular protein as assayed by ELISA when cultured in the presence of a culture medium which comprises Insulin-Transferrin-Selenium (ITS), Glutamax, Dexamethasone, hepatocyte growth factor (HGF), Oleic acid and 9CLA.

According to an aspect of some embodiments of the present invention there is provided an isolated hepatocyte obtainable by the method according to the method of some embodiments of the invention.

According to an aspect of some embodiments of the present invention there is provided an isolated population of cells wherein at least 50% of the cells comprise the isolated hepatocyte of some embodiments of the invention.

According to an aspect of some embodiments of the present invention there is provided a method of screening a compound for liver toxicity, comprising:

(a) incubating the isolated population of cells of some embodiments of the invention with the compound for a pre-determined time period, and;

(b) determining percentage of a parameter indicative of liver toxicity following the pre-determined time period, thereby screening the compound for the liver toxicity.

According to an aspect of some embodiments of the present invention there is provided a kit for screening a compound for liver toxicity comprising the isolated population of cells of some embodiments of the invention and at least one agent capable of detecting a toxicological endpoint selected from the group consisting of: steatosis, cholestasis and apoptosis.

According to an aspect of some embodiments of the present invention there is provided a nutrition formula for an infant comprising 9CLA.

According to some embodiments of the invention, the effective amount of said PXR agonist causes differentiation of said immature hepatocyte into a mature hepatocyte.

According to some embodiments of the invention, the mature hepatocyte is characterized by an albumin$^+$/CY3A4$^+$/E-cadherin$^+$/OCT4$^-$/SOX2$^-$/A1AT$^+$/HNF4$\alpha^+$ expression signature.

According to some embodiments of the invention, the effective amount of said PXR agonist is provided in a concentration of at least half maximal effective concentration ($EC_{50}$) of said PXR agonist.

According to some embodiments of the invention, the PXR agonist is selected from the group consisting of: a small molecule and a bile acid.

According to some embodiments of the invention, the small molecule is selected from the group consisting of: Rifampicin, TO901317, SR12813, mevastatin, rifaximin, hyperforin, meclizine, paclitaxel, atorvastatin, pregnenolone-16alpha-carbonitrile, Butamben and 24(S),25-Epoxycholesterol.

According to some embodiments of the invention, the bile acid is selected from the group consisting of lithocholic acid, cholic acid, chenodeoxycholic acid, deoxycholic acid, and ursodeoxycholic acid, or a derivative thereof.

According to some embodiments of the invention, the steroid is selected from the group consisting of progesterone, 17α-hydroxyprogesterone, 17α-hydroxypregnenolone, 5α-dihydroprogesterone, 53-dihydroprogesterone, allopregnanolone, corticosterone, cyproterone acetate, spironolactone, dexamethasone, and mifepristone.

According to some embodiments of the invention, the contacting or the administering is performed in an absence of an IL6 ligand.

According to some embodiments of the invention, the fatty acid is non-conjugated.

According to some embodiments of the invention, a concentration of the non-conjugated is at least 50 μM.

According to some embodiments of the invention, the immature hepatocyte is characterized by an alpha-feto protein (AFP)+/Albumin+/CYP3A7+/SOX2−/OCT4− expression signature.

According to some embodiments of the invention, the immature hepatocyte does not differentiate into bile duct cells.

According to some embodiments of the invention, the method resulting in a mature hepatocyte characterized by an albumin+/CY3A4+/E-cadherin+/OCT4−/SOX2−/A1AT+/HNF4α+ expression signature.

According to some embodiments of the invention, the IL6 ligand is selected from the group consisting of oncostatin M (OSM), interleukin 6 (IL6), leukemia inhibitory factor (LIF), leptin (OB), Cardiotrophin-1/CT-1, CLC, CNTF, G-CSF, IL-11, IL-31, and Neuropoietin/NP.

According to some embodiments of the invention, the immature hepatocyte is obtained by an in vitro differentiation of a pluripotent stem cell.

According to some embodiments of the invention, the immature hepatocyte is obtained by an in vitro differentiation of a hepatoblast.

According to some embodiments of the invention, the in vitro differentiation of the hepatoblast is performed by culturing the hepatoblast for a pre-determined time period in a culture medium which comprises an IL6 ligand.

According to some embodiments of the invention, prior to formation of the hepatoblast the fatty acid and/or the small molecule are absent from a culture comprising the hepatoblast.

According to some embodiments of the invention, the non-conjugated fatty acid is selected from the group consisting of oleic acid (OA), Palmitic Acid and linoleic acid (LA).

According to some embodiments of the invention, the non-conjugated fatty acid is selected from the group consisting of oleic acid (OA) and linoleic acid (LA).

According to some embodiments of the invention, the non-conjugated fatty acid is oleic acid (OA).

According to some embodiments of the invention, the non-conjugated fatty acid is linoleic acid (LA).

According to some embodiments of the invention, the non-conjugated fatty acid is Palmitic Acid.

According to some embodiments of the invention, the fatty acid is a conjugated fatty acid.

According to some embodiments of the invention, the conjugated fatty acid is provided at a concentration of at least 50 μM.

According to some embodiments of the invention, the conjugated fatty acid is provided at a concentration of 50-200 μM.

According to some embodiments of the invention, the conjugated fatty acid is 9-cis, 11-trans conjugated linoleic acid (9CLA).

According to some embodiments of the invention, the conjugated fatty acid is selected from the group consisting of a conjugated linoleic acid which comprises two conjugated double bonds, a conjugated linoleic acid which comprises three conjugated double bonds, 9E,11Z,15E-octadeca-9,11,15-trienoic acid (Rumelenic acid), 9E,11Z,13Z,15E-octadeca-9,11,13,15-tetraenoic acid (α-Parinaric acid), all trans-octadeca-9,11,13,15-tretraenoic acid (β-Parinaric) acid, and 5Z,8Z,10E,12E,14Z-eicosanoic acid (Bosseopentaenoic acid).

According to some embodiments of the invention, the fatty acid is an omega 3 polyunsaturated fatty acid.

According to some embodiments of the invention, the amphipathic carboxylic acid comprises a fibrate.

According to some embodiments of the invention, the fibrate is selected from the group consisting of Fenofibrate, Bezafibrate, Ciprofibrate, Clofibrate, Gemfibrozil, Fenofibrate, and Clinofibrate.

According to some embodiments of the invention, the Thiazolidinedione is selected from the group consisting of Pioglitazone, Rosiglitazone, Lobeglitazone, Troglitazone, Ciglitazone, Darglitazone, Englitazone, Netoglitazone and Rivoglitazone.

According to some embodiments of the invention, the metabolic maturation comprises an increase in a mitochondrial mass per cell as compared to the mitochondrial mass in a control immature hepatocyte.

According to some embodiments of the invention, the increase in the mitochondrial mass comprises an increase in a proliferation rate of the mitochondria as compared to a proliferation rate of the mitochondria in a control immature hepatocyte.

According to some embodiments of the invention, the metabolic maturation comprises an increase in a maturation state of the mitochondria as compared to a maturation state of a control immature hepatocyte.

According to some embodiments of the invention, the immature hepatocyte is from a newborn human individual.

According to some embodiments of the invention, the hepatoblast is obtainable by a method which comprises:

(a) culturing undifferentiated pluripotent stem cells in a medium which comprises activin A, B27, Wnt3A and hepatocyte growth factor (HGF) to thereby obtain cells characteristics of a definitive endoderm, and subsequently;

(b) culturing the cells characteristics of the definitive endoderm in a culture medium which comprises Dimethyl sulfoxide (DMSO), to thereby obtain the hepatoblast.

According to some embodiments of the invention, wherein step (b) further comprises passaging the cells at least once in the culture medium which comprises the DMSO.

According to some embodiments of the invention, the hepatocyte is characterized by a Cytochrome P450 3A4 (CYP3A4) activity which is capable of oxidizing at least 1 pmol of 7-benzyloxy-4-trifluoromethylcoumarin (BFC) per minute per milligram of cellular protein.

According to some embodiments of the invention, the hepatocyte is characterized by an alpha feto-protein (AFP) production of at least 60 microgram per day per milligram cellular protein as determined by an ELISA.

According to some embodiments of the invention, the hepatocyte is characterized by nuclear expression of PXR.

According to some embodiments of the invention, the liver toxicity comprises steatosis.

According to some embodiments of the invention, the steatosis is assayable using the LipidTox neutral lipid stain.

According to some embodiments of the invention, the liver toxicity comprises cholestasis.

According to some embodiments of the invention, the cholestasis is assayable using the CDFDA staining.

According to some embodiments of the invention, the liver toxicity comprises apoptosis.

According to some embodiments of the invention, the apoptosis is assayable using the TUNEL assay.

According to some embodiments of the invention, the nutrition formula being suitable for infant(s) born by C-section.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 9:
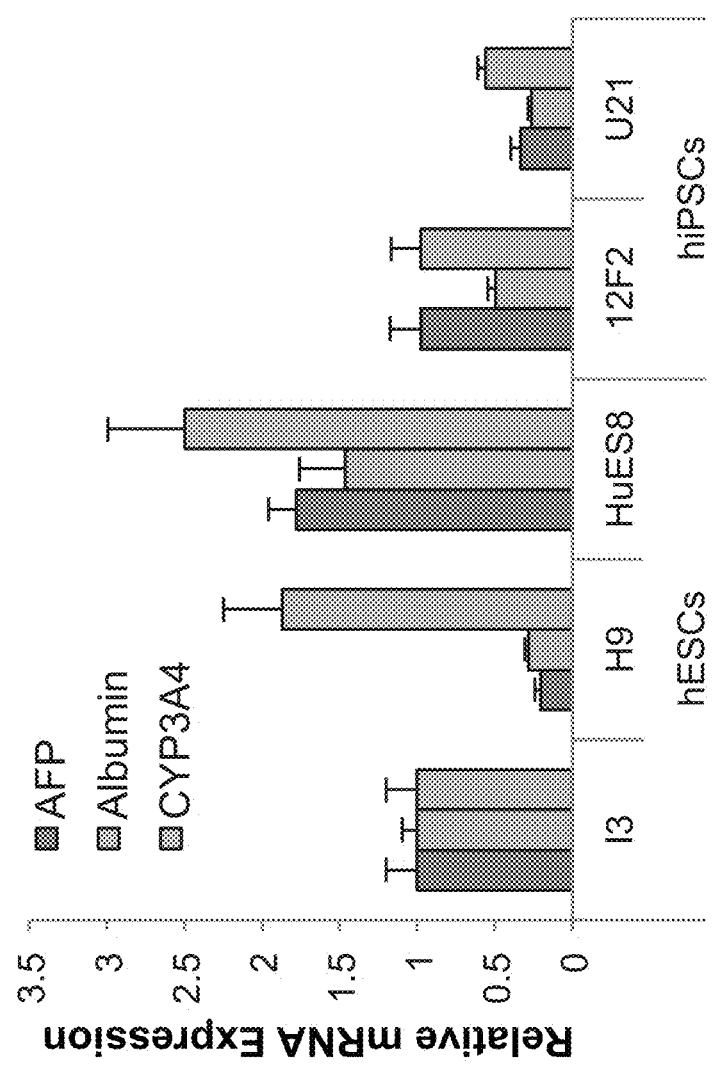

FIGS. 1A-H demonstrate the differentiation of human embryonic stem cell (hESC) derived hepatocytes according to the method of some embodiments of the invention. FIG. 1A—Schematic of a four-stage protocol used to control hepatocyte differentiation. Note that in the last stage (stage 4, days 12-16) the medium is devoid of oncostatin-M (OSM). FIG. 1B—Phase and immunofluorescence micrographs of differentiating 13 human embryonic stem cells. Differentiating cells undergo distinct morphological changes (Phase images, top row) and progress through defined transcriptional states toward hepatocytes. FIGS. 1C-E—qRT-PCR analyses. FIG. 1C—qRT-PCR analysis of transcription factors maintaining pluripotency (OCT4 and SOX2); FIG. 1D—qRT-PCR analysis of transcription factors regulating hepatic differentiation (SOX17, GATA4, FOXA2 and HNF4A); FIG. 1E—qRT-PCR analysis of key liver proteins (AFP, albumin and A1AT).

The results show that the pluripotency factors disappear by day 8 (FIG. 1C), followed by a transient expression of endodermal genes (FIG. 1D) and the gradual appearance of hepatocyte specific proteins (FIG. 1E). FIG. 1F—Flow cytometry of cells at day 3 (endoderm) shows that 41% of the cells express definitive endoderm markers CXCR4 and SOX17. FIG. 1G—Flow cytometry profile of cells at day 7 (hepatoblasts) shows that 83% of the cells express standard hepatoblast markers, HNF4A and FOXA2. FIG. 1H—Flow cytometry of cells after 16 days of differentiation (hepatocytes) shows that 83% of the cells are positive for both albumin and HNF4A. The following abbreviations were used: Wnt3A, Wingless-Type MMTV Integration Site Family, Member 3A; HGF, hepatic growth factor; DMSO, Dimethyl sulfoxide; DEX, Dexamethasone; OSM, oncostatin-M; FGF2, fibroblast growth factor-2; OCT4, octamer-binding transcription factor 4; SOX17, SRY (sex determining region Y)-box 17; GATA4, GATA binding protein 4; FOXA2, forkhead box protein A2; HNF4A, hepatocyte nuclear factor 4-alpha; SOX2, SRY (sex determining region Y)-box 2; AFP, alpha-fetoprotein; A1AT, alpha 1-antitrypsin.

FIGS. 2A-I demonstrate that LCA and MK4 drive PXR dependent hepatic maturation. FIGS. 2A-B—Quantitative reverse-transcriptase polymerase chain reaction (qRT-PCR) analysis of nuclear receptors, drug transporters, and phase I drug metabolism enzymes in hESC-derived hepatocytes (hESC-H D16), adult primary human hepatocytes (PHH), and HepG2 cells. hESC-derived hepatocytes show similar expression of CAR and FXR, when compared to PHHs, while expressing lower levels of PXR, CYP3A4, and CYP2C9 that are still substantially higher than that of HepG2 cells (FIG. 2A). hESC-derived hepatocytes show a higher PPARα expression than PHHs, but comparable expression of albumin and A1AT (FIG. 2B). FIG. 2C—Molecular structures of Lithocholine Acid (LCA) and Vitamin K2 (MK4). FIGS. 2D-E—qRT-PCR analyses of hESC-derived hepatocytes exposed to increasing concentrations of LCA (FIG. 2D) or MK4 (FIG. 2E) during the final maturation step (days 12-16). LCA induced an exponential response, reaching 5- to 73-fold induction in PXR and its CYP2C9 and CYP3A4 target genes. MK4 supplementation had little effect on hESC-derived hepatocyte gene expression. FIG. 2F—qRT-PCR analysis of hESC-derived hepatocytes cultured with 10 µM of LCA, 10 µM of MK4, or 10 µM of both compounds during the final maturation step. Cells show a synergistic effect, with PXR induced by 3.7-fold by the combination of LCA and MK4, compared to 1.3- and 1.9-fold for LCA and MK4, respectively. FIG. 2G—PXR-copGFP reporter activity in hESC-derived hepatocytes. Differentiated cells that were cultured in the presence of LCA and MK4 show a significant increase in PXR activity. FIG. 2H—A histogram depicting quantification of immunofluorescence analysis of PXR showing a 3-fold increase in nuclear localization of PXR in cells cultured with LCA and MK4, compared to standard differentiation. FIG. 2I—Addition of silibinin, a PXR inhibitor, to the final maturation step (days 12-16) of hESC-derived hepatocytes blocks the effect of LCA and MK4 supplementation. *P<0.05; **P<0.01. Abbreviations: MDR1/P-gp, multi-drug resistance protein; MRP3, multidrug resistance-associated protein; PXR, pregnane X receptor; FXR, farnesoid X receptor; CAR, constitutive androstane receptor; MK4, Menatetrenone-4 (Vitamin $K_2$); MDR1, multidrug resistance protein 1; MRP3, multidrug resistance-associated protein 3; OATP2, organic anion-transporting polypeptide-2; PPARA, peroxisome proliferator-activated receptor alpha.

FIGS. 3A-F depict morphology, secretome and RNA-Seq analysis of hepatic maturation in the presence of 10 µM LCA and 10 µM MK4. FIG. 3A—hESC-derived hepatocytes (hESC-H) show a homogenous perinuclear albumin and CYP3A4 staining, clear HNF-4α nuclear localization, and lateral E-cadherin staining. White arrows indicate binuclear cells, a trait of PHHs (top). FIG. 3B—CDFDA staining shows functional bile canaliculi (arrows), whereas some no-polarized cells show diffused green CDF. FIG. 3C—Graph depicting the dynamics of albumin, AFP, and ApoB100 secretion during hepatic differentiation. hESC-derived hepatocyte production of albumin and ApoB100 steadily increased during LCA and MK4 treatment and, by day 16, was not significantly different from PHHs. In contrast, AFP showed 22% decrease during the end of the differentiation period (P<0.05). FIG. 3D—Unsupervised hierarchical clustering using Spearman's rank correlation of 2,925 differentially expressed genes analyzed using RNA-Seq shows that hESC-H treated with LCA and MK4 (LCA/MK4) cluster closer to PHHs than to FHHs than untreated hESC-H controls (control). Representative heat map of 75 differential genes is shown as well. FIG. 3E—RNA abundance of adult liver markers ASGR1, CYP3A4, and GPT1/ALT was higher in treated than untreated hESC-H. FIG. 3F—RNA abundance of fetal liver markers CYP3A7 and RFC3 was higher in untreated than treated hESC-H.

FIGS. 4A-F demonstrate that hESC-derived hepatocytes (hESC-H) exhibit inducible CYP450 and accurate toxicological response. FIG. 4A—Log-scale CYP450 activity of hESC-H treated with LCA and MK4 (LCA/MK4), compared to untreated hESC-H (control), adult primary human hepatocytes (PHHs), and HepG2 cells. hESC-H treated with LCA and MK4 exhibit higher CYP450 activity than HepG2 and untreated cells. Fetal CYP1A activity is higher than PHHs when measuring EROD breakdown. MFC and BFC breakdown in differentiated cells is lower than primary cells, but higher than untreated hESC-H (P<0.05) FIG. 4B—Induction of CYP450 activity in hESC-H treated with LCA and MK4 in response to 72 hours of stimulation with AhR agonist omeprazole (purple bars) or PXR agonist rifampicin (orange bars). Omeprazole preferentially induced CYP1A (P=0.012; n=3), whereas rifampicin shows a clear induction of MFC metabolism (P=0.048; n=3). FIG. 4C—PXR and CYP450 gene expression analysis in hESC-derived hepatocytes after 2% DMSO treatment. Exposure of differentiated cells to DMSO increased expression of all CYP450 enzymes measured. FIG. 4D—Dose-dependent toxicity curves and $TC_{50}$ values of different compounds obtained from 24-hour dose response in hESC-H treated with LCA and MK4 (red circles). Although generally considered safe, melatonin showed clear toxicity in differentiated cells, albeit at high concentrations. FIG. 4E—$TC_{50}$ values of different compounds obtained from 24-hour dose response in PHH and HepG2 cells, compared with the values obtained from LCA- and MK4-treated hESC-H (LCA/MK4) and untreated cells. Normalized $TC_{50}$ toxicity profile generated for hESC-H treated with LCA and MK4 was not significantly different from primary cells (P=0.13; n=3), whereas HepG2 profile was significantly different (P=0.04; n=3). FIG. 4F—Comparison of $TC_{50}$ values between PHHs and hESC-H treated with LCA and MK4 (red circles) and untreated cells (green squares). hESC-H treated with LCA and MK4 showed a striking correlation of $R^2=0.94$ to the perfect 45-degree angle (dotted line), compared to $R^2=0.19$ for untreated cells. Abbreviation: N.A., not appreciable.

FIGS. 5A-I demonstrate that hESC-derived hepatocytes (hESC-H) show accurate prediction of toxicological endpoints. Differentiation of 13 hESC-derived hepatocytes was carried out in the presence of LCA and MK4. FIGS. 5A-F—Fluorescence quantification of toxicological endpoints in hESC-derived hepatocytes exposed to TC20 concentrations. FIGS. 5A-B—Intracellular lipid accumulation (steatosis) in hESC-derived hepatocytes after a 24-hour exposure to steatosis-causing drugs, measured by LipidTOX. Exposure to amiodarone, acetylsalicylic acid (aspirin) or valproic acid caused similar and significant increase in lipid accumulation (P<0.001). FIGS. 5C-D—Loss of cell polarization and bile secretion (cholestasis) after a 24-hour exposure to cholestasis-causing drugs, evaluated by CDFDA. Troglitazone, chlorpromazine (thorazine), and cyclosporine A caused a significant, 14-fold loss of epithelial polarization (P<0.003). FIGS. 5E-F—Apoptosis of hESC-derived hepatocytes after a 24-hour exposure to apoptosis-causing drugs, measured by TUNEL. Diclofenac, acetaminophen, and aflatoxin $B_1$ caused a significant increase in DNA fragmentation, compared to control (P<0.02). FIGS. 5G-I—Exposure to $TC_{20}$ concentration of melatonin caused a significant (P<0.006) increase in intracellular lipid accumulation, while not affecting bile secretion or cell viability. Abbreviation: r.u., relative units.

FIGS. 6A-J demonstrate that oleic acid (OA) and linoleic acid (LA) induce hESC derived hepatocytes maturation. FIG. 6A—images (on the left) and histograms (on the right) depicting GFP based nuclear receptor activity reporters revealing a dose dependent increase in the activation of PPARα, LXRα and PXR and no change in the activation of FXR in response to rising concentrations of oleic acid (OA) and linoleic acid (LA). The images on the left show expression of PPARα, LXRα, PXR and FXR in the absence ("control, 0 μM") or presence of OA and LA ("OA+LA" at 125 μM of OA and LA) fatty acids. The histogram, show the dose dependent increase to 62 μM, 125 μM and 250 μM of the OA and LA fatty acids. FIG. 6B—qRT-PCR analysis of nuclear receptors and their target genes in response to different fatty acid concentrations. These results correlate to those of the activity reporter assay, i.e. a dose dependence expression of the LXR, PPAR and PXR nuclear receptor and their target genes is observed. *p<0.05, **p<0.01. FIG. 6C—Albumin and AFP immunostaining after differentiation following a four day treatment with OA and LA. Albumin (green label), AFP (red label) and Hoechst (nuclear staining, blue label). FIG. 6D—Microscopic quantification of albumin and AFP positive cells. OA and LA induced a dose-dependent increase in albumin and decrease in AFP up to 125 μM. FIG. 6E—Apoptosis increased at fatty acid concentrations above 125 μM, suggesting an optimal concentration of about 100 μM OA and LA. FIG. 6F—qRT-PCR analysis of hESC-derived cells cultured with 100 μM OA and 100 μM LA or OA+LA and PPAR antagonist GW9662 during the final maturation step. Cells show a significant PPAR dependent expression of lipid metabolism genes and albumin. FIG. 6G—hESC derived hepatocytes (hESC-H) showed 2-fold increase in albumin secretion following treatment with 100 μM OA and LA, an that was blocked by PPAR inhibitor GW9662. FIG. 6H Histogram (FIG. 6I) a 7% increase in nuclear localization in cells cultured with OA and LA, and a 50% increase in nuclear localization when 100 μM LA was replaced with 100 μM 9CLA, compared to un treated cells. GW9662 treatment leads to a significant decrease in nuclear localization reversing fatty acids effect. FIG. 6I—qRT-PCR analysis of PXR and its CYP450 target genes. Supporting PPAR-dependent PXR activation, CYP3A4 and CYP2C9 gene expression increased significantly in response to 9CLA and were down-regulated after GW9662 treatment. FIG. 6J—CYP450 activity of hESC-H treated with 100 μM OA and LA, or 100 μM OA and 9CLA, compared to untreated hESC-H (control), adult human hepatocytes (hepatocytes), and HepG2 cells. hESC-H treated with OA and 9CLA exhibit higher CYP450 activity than HepG2 and untreated cells. MFC and BFC breakdown in differentiated cells is lower than primary cells, but higher than control.

FIGS. 7A-J demonstrate that hESC-derived hepatocytes exhibit PPAR-dependent increase in mitochondrial mass in response to fatty acids. FIG. 7A—TEM representative pictures of hESC-derived control cells, OA+LA treated and OA+9CLA treated cells. All cells were metabolically active with large amounts of stored glycogen (dark dotes), rough and smooth ER and mitochondria. Treated cells had more lipid droplets and their mitochondria had a narrower morphology compared to control (black arrows). Bar=2000 nm. FIGS. 7B-C—TEM based measurements of average mitochondria diameter (FIG. 7B) and cellular and nuclear area (FIG. 7C). Similar to postnatal mitochondria development, treated cells were bigger and the average mitochondria diameter was reduced. FIG. 7D—HSP60/Actin/Hoechst immunofluorescence (IF) staining, and CellProfiler analysis (black and white) of mitochondrial network. FIGS. 7E-H—Quantification of minor (FIG. 7E) and major (FIG. 7F) mitochondria axis length, eccentricity (FIG. 7G) and HSP60 relative expression (FIG. 7H), according to IF analyses. Treated cells exhibit a more elongated and less fragmented morphology indicating the development of a mature mitochondrial network. Treatment with GW9662 reversed the effect. Mitochondria mass increased by 20% ($p<0.001$). FIG. 7I—Apoptosis remained unchanged in all treatments indicating that the morphological alteration were not a result of cell death. FIG. 7J—qRT-PCR of key genes in mitochondria biogenesis, fusion and fission supporting molecular mechanism underlie morphological changes. Selected key regulatory genes in mitochondrial function and morphology were all up-regulated in a PPAR dependent manner, with MFN2 increasing more significantly increasing the fusion/fission ratio.

FIGS. 8A-B demonstrate that fatty acids dramatically increase mitochondrial activity of hESC-derived hepatocytes. FIGS. 8A-B—Dynamic OCR measurements during mitochondrial stress test (Seahorse Biosciences) (FIG. 8A) and histogram summary of fluxes (FIG. 8B). Treatment with 100 µM OA and LA increased basal respiration, ATP production and maximal respiration of hESC-H. Replacing LA with 9CLA showed further increase, reaching 60% of primary human hepatocytes. Results are presented as mean±s.d *$p<0.05$, **$p<0.01$.

FIG. 9 is a histogram depicting the generalization of the hPSC-H protocol across multiple cell lines. qRT-PCR analysis of hepatocyte differentiation protocol on Day 16, using hESC lines 13 (Technion), H9 (WiCell), and HuES8 (Harvard) as well as hiPSC lines 12F2 (HUJI) and U21 (KUL). Results are normalized to the hESC 13 line reported (FIGS. 1A-H-3A-F).

Figure 10:
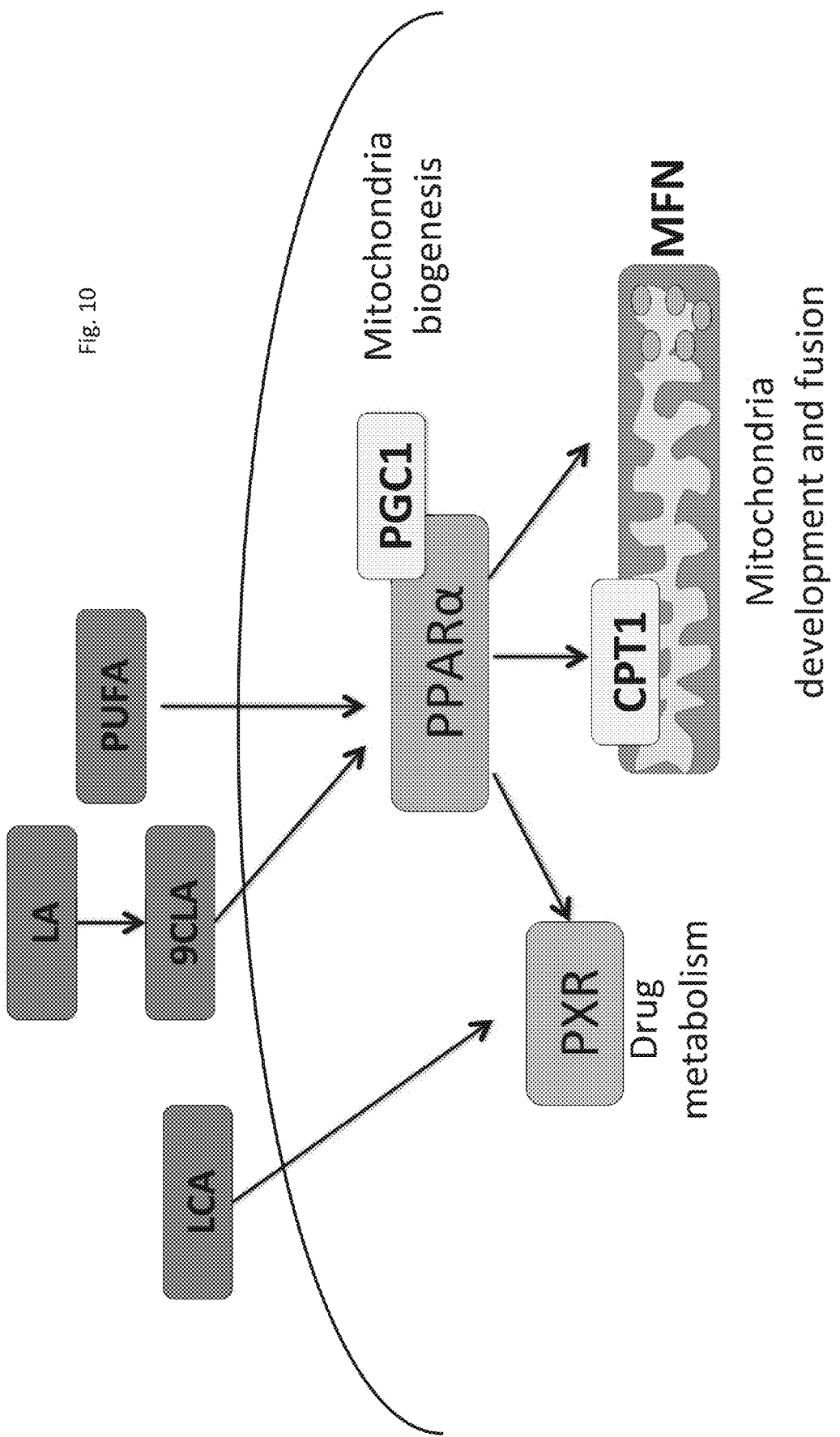

FIG. 10 is a schematic model for proposed mechanism demonstrating that microbial-derived bile acid LCA and 9CLA affect hepatocyte maturation through parallel pathways controlled by nuclear receptors PXR and PPARA, respectively.

Figure 11A:
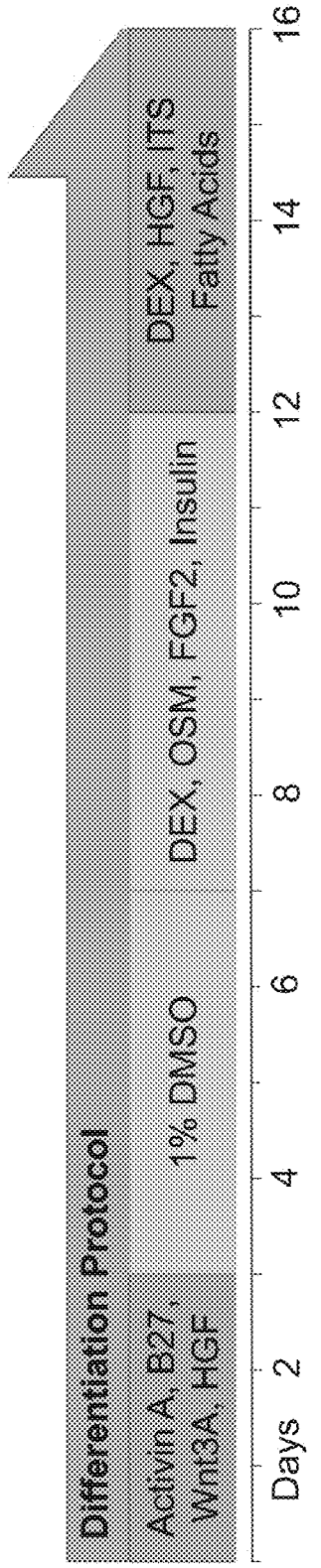
Figure 11B:
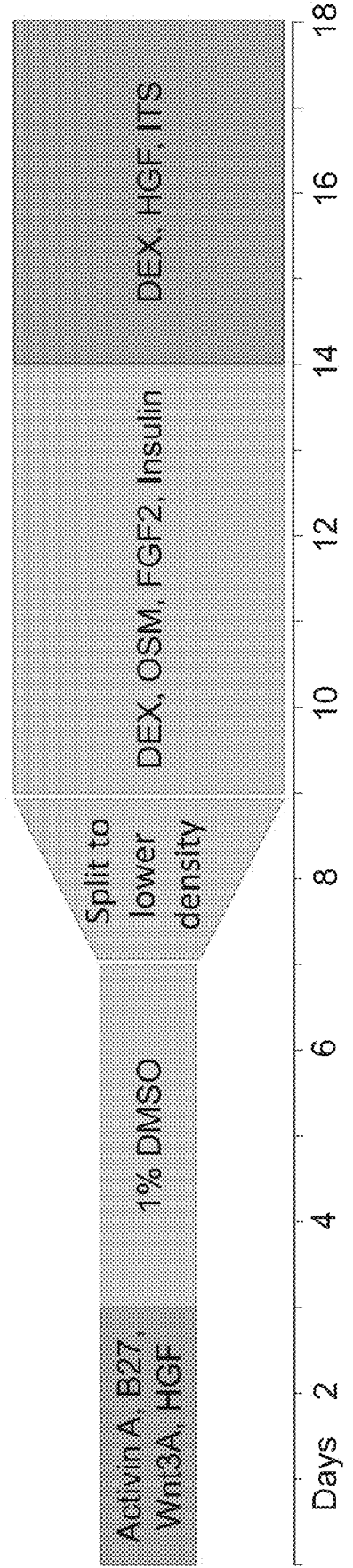

FIGS. 11A-B depict schematic illustrations of the differentiation method according to some embodiments of the invention.

DESCRIPTION OF SPECIFIC EMBODIMENTS OF THE INVENTION

The present invention, in some embodiments thereof, relates to methods of increasing metabolic maturation of immature hepatocytes and isolated hepatocytes resulting thereof.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Due to recent developments in Pluripotent Stem Cell (PSC) hepatic differentiation and maturation, PSC-derived hepatocytes are now considered a reliable cellular alternative for drug development and clinical applications. The present inventors have previously shown that post-partum microbial-derived cues, litocholic acid and vitamin $K_2$, can drive the metabolic maturation of hESC-derived and fetal hepatocytes by activating PXR (Avior, 2015).

The present inventors report a four-step 16 to 18 day differentiation protocol to produce a homogenous culture of hPSC-derived hepatocytes. The present inventors have uncovered that the addition of oleic acid (OA) and LA to the last stage of PSC differentiation induces a dose-dependent activation of key hepatic nuclear receptors, PPAR, PXR and LXR, essential for the metabolic functionality of the mature hepatocyte. Further supporting the fatty acid-induced maturation, albumin expression increased in a PPAR dependent manner concurrently with a decrease in alpha-fetoprotein (AFP) expression. Replacing LA with microbial derived 9CLA promoted an additional PPAR-dependent PXR activation, increasing nuclear localization by 30% and up-regulating CYP450 gene expression and activity. Functional and morphological analyses performed to evaluate the influence of fatty acids, showed a PPAR dependent increase in mitochondrial function, biogenesis and fusion, resulting in a significant increase in mitochondrial mass and the relevant metabolic fluxes, which are critical for proper hepatocyte function. This work provides fresh insights into the role of postnatal nutritional cues in hepatic maturation and mitochondrial development via the activation of lipid regulated PPAR. This work sheds light on the tight link between nutrition, gut colonization and cellular developmental processes that underlie haptic maturation.

According to an aspect of some embodiments of the invention there is provided a method of increasing metabolic maturation of an immature hepatocyte, the method comprising contacting an immature hepatocyte which expresses alpha-fetoprotein (AFP) and albumin with an effective amount of a fatty acid or a small molecule selected from the group consisting of: an amphipathic carboxylic acid, Thiazolidinedione (TZD), WY-14643 (Pirinixic Acid), GW409544, GW6471, Leukotriene B4, GW 7647, Perfluorooctanesulfonic Acid, PERFLUOROOCTANOIC ACID, CP-775146, CP-865520, UNII-999KY5ZIGB, and Gemfibrozil, thereby increasing the metabolic maturation of the immature hepatocyte.

It should be noted that the fatty acid or a small molecule selected from the group consisting of: an amphipathic carboxylic acid, Thiazolidinedione (TZD), WY-14643 (Pirinixic Acid), GW409544, GW6471, Leukotriene B4, GW 7647, Perfluorooctanesulfonic Acid, PERFLUOROOCTANOIC ACID, CP-775146, CP-865520, UNII-999KY5ZIGB, and Gemfibrozil are capable of activating the PPARα (peroxisome proliferator-activated receptor alpha) and optionally the PPARγ (peroxisome proliferator-activated receptor gamma).

PPAR is subfamily of the nuclear receptor superfamily of transcription factors, plays important roles in lipid and glucose metabolism, and has been implicated in obesity-related metabolic diseases such as hyperlipidemia, insulin resistance, and coronary artery disease.

PPARα (peroxisome proliferator-activated receptor alpha) is a fatty acid-activated member of the PPAR subfamily. It is expressed primarily in metabolic tissues (brown adipose tissue, liver, kidney) but elevated levels are also present in the digestive (jejunum, ileum, colon, gall bladder) and cardiopulmonary (aorta, heart) systems (Sher T, et al.

1993; "cDNA cloning, chromosomal mapping, and functional characterization of the human peroxisome proliferator activated receptor". Biochemistry 32 5598-604).

PPARγ (peroxisome proliferator-activated receptor gamma) is a fatty acid-activated member of the PPAR subfamily. It is expressed at low levels in most physiological systems, including the central nervous system (CNS), endocrine system, gastrointestinal system, reproductive system, cardiopulmonary system and metabolic tissues, but is most highly expressed in brown and white adipose tissue (Elbrecht A, et al. 1996; "Molecular cloning, expression and characterization of human peroxisome proliferator activated receptors gamma 1 and gamma 2". Biochem. Biophys. Res. Commun. 224 431-7 V).

The phrase "immature hepatocyte" refers to a hepatocyte cell which expresses alpha-fetoprotein and produces albumin. It should be noted that an immature hepatocyte is also characterized by the expression of cytochrome 3A7 (CYP3A7).

According to some embodiments of the invention, the immature hepatocyte is characterized by an alpha-fetoprotein $(AFP)^+/Albumin^+/CYP3A7^+/SOX2^-/OCT4^-$ expression signature.

According to some embodiments of the invention, the immature hepatocyte is characterized by production of at least 1 μg Albumin/ml/mg cellular protein (e.g., 1.5 μg albumin per ml per mg cellular protein).

According to some embodiments of the invention, the immature hepatocyte is characterized by production of at least 25 μg AFP/ml/mg cellular protein (e.g., 37 μg AFP/ml/mg cellular protein).

According to some embodiments of the invention, the immature hepatocyte does not differentiate into bile duct cells.

According to some embodiments of the invention, the metabolic maturation comprises an increase in a mitochondrial mass per cell as compared to the mitochondrial mass in a control immature hepatocyte.

As used herein the phrase "mitochondria mass" refers to number of mature mitochondria per cell.

According to some embodiments of the invention, the increase in the mitochondrial mass comprises an increase in a proliferation rate of the mitochondria as compared to a proliferation rate of the mitochondria in a control immature hepatocyte.

According to some embodiments of the invention, the proliferation of the mitochondria comprises biogenesis, fission and/or fusion of the mitochondria.

According to some embodiments of the invention, the metabolic maturation comprises an increase in a maturation state of the mitochondria as compared to a maturation state of a control immature hepatocyte.

It should be that a mature mitochondria refers to elongated, cristae-rich mitochondria organelle connected in network, which express mitochondrial proteins such as HSP60.

According to some embodiments of the invention, the immature hepatocyte is from a newborn human individual.

According to some embodiments of the invention, the immature hepatocyte is obtained by an in vitro differentiation of a pluripotent stem cell.

As used herein the term "fatty acid" refers to a carboxylic acid with an aliphatic chain.

According to some embodiments of the invention, the aliphatic chain comprises an even number of carbon atoms. For example, the aliphatic chain of the fatty acid can include between 4 to 28 carbon atoms.

The aliphatic compounds can be saturated (saturated fatty acid) joined by single bonds (alkanes), or an unsaturated (unsaturated fatty acid), with double bonds (alkenes) or triple bonds (alkynes). Besides hydrogen, other elements can be bound to the carbon chain, the most common being oxygen, nitrogen, sulfur, and chlorine.

It should be noted that a fatty acid is not a steroid based molecule. Thus, fatty acid with an aliphatic chain is entirely different from a bile acid such as lithocholic acid, which includes aromatic rings in the backbone.

According to some embodiments of the invention, the derivative of the fatty acid is a prostaglandin molecule. Prostaglandins are lipids derived from fatty acids (they have one 5-carbon ring). Each prostaglandin contains 20 carbon atoms, including a 5-carbon ring.

According to some embodiments of the invention, the fatty acid is non-conjugated.

According to some embodiments of the invention, the concentration of the non-conjugated fatty acid is at least 50 μM, e.g., at least 55 μM, e.g., at least 60 μM, e.g., at least 65 μM, e.g., at least 70 μM, e.g., at least 75 μM, e.g., at least 80 μM, e.g., at least 85 μM, e.g., at least 90 μM, e.g., at least 95 μM, e.g., at least 100 μM, e.g., at least 105 μM, e.g., between 80-150 μM, e.g., between 80-120 μM, e.g., 90-110 μM. e.g., about 100 μM.

According to some embodiments of the invention, the concentration of the non-conjugated fatty acid does not exceed 240 μM.

According to some embodiments of the invention, the non-conjugated fatty acid is selected from the group consisting of oleic acid (OA), Palmitic Acid and linoleic acid (LA).

According to some embodiments of the invention, the fatty acid is a conjugated fatty acid.

According to some embodiments of the invention, the conjugated fatty acid is provided at a concentration of at least 50 μM, e.g., at least 55 μM, e.g., at least 60 μM, e.g., at least 65 μM, e.g., at least 70 μM, e.g., at least 75 μM, e.g., at least 80 μM, e.g., at least 85 μM, e.g., at least 90 μM, e.g., at least 95 μM, e.g., at least 100 μM, e.g., at least 105 μM, e.g., at least 110 μM, e.g., at least 115 μM, e.g., at least 120 μM, e.g., at least 125 μM, e.g., at least 130 μM, e.g., at least 135 μM, e.g., at least 140 μM, e.g., at least 145 μM, e.g., at least 150 μM, e.g., at least 155 μM, e.g., at least 160 μM, e.g., at least 165 μM, e.g., at least 170 μM, e.g., at least 175 μM, e.g., at least 180 μM, e.g., at least 185 μM, e.g., at least 190 μM, e.g., at least 200 μM, e.g., between 80-150 μM, e.g., between 80-120 μM, e.g., 90-110 μM. e.g., about 100 μM.

According to some embodiments of the invention, the concentration of the conjugated fatty acid does not exceed 240 μM.

According to some embodiments of the invention, the conjugated fatty acid is provided at a concentration of 50-200 μM.

According to some embodiments of the invention, the conjugated fatty acid is 9-cis, 11-trans conjugated linoleic acid (9CLA).

According to some embodiments of the invention, the conjugated fatty acid is selected from the group consisting of a conjugated linoleic acid which comprises two conjugated double bonds, a conjugated linoleic acid which comprises three conjugated double bonds, 9E,11Z,15E-octadeca-9,11,15-trienoic acid (Rumelenic acid), 9E,11Z,13Z,15E-octadeca-9,11,13,15-tetraenoic acid (α-Parinaric acid), all trans-octadeca-9,11,13,15-tretraenoic acid (β-Parinaric) acid, and 5Z,8Z,10E,12E,14Z-eicosanoic acid (Bosseopentaenoic acid).

According to some embodiments of the invention, the conjugated linoleic acid which comprises two conjugated double bonds is selected from the group consisting of 9Z,11E-octadeca-9,11-dienoic acid (Rumenic acid or Bovinic acid) and 10E,12Z-octadeca-10,12-dienoic acid (10CLA).

According to some embodiments of the invention, the conjugated linoleic acid which comprises three conjugated double bonds is selected from the group consisting of 8E,10E,12Z-octadecatrienoic acid (α-Calendic acid), 8E,10E,12E-octadecatrienoic acid (β-Calendic acid), 8Z,10E,12Z-octadecatrienoic acid (Jacaric acid), 9Z,11E, 13E-octadeca-9,11,13-trienoic acid (α-Eleostearic acid), 9E,11E,13E-octadeca-9,11,13-trienoic acid (β-Eleostearic acid), 9Z,11Z,13E-octadeca-9,11,13-trienoic (Catalpic acid), and 9Z,11E,13Z-octadeca-9,11,13-trienoic acid (Punicic acid).

According to some embodiments of the invention, the fatty acid is an omega 3 polyunsaturated fatty acid.

According to some embodiments of the invention, the omega 3 polyunsaturated fatty acid is selected from the group consisting of all-cis 7,10,13-hexadecatrienoic acid (Hexadecatrienoic acid (HTA)), all-cis-9,12,15-octadecatrienoic acid (Alpha-linolenic acid (ALA)), all-cis-6,9,12, 15,-octadecatetraenoic acid (Stearidonic acid (SDA)), all-cis-11,14,17-eicosatrienoic acid (Eicosatrienoic acid (ETE)), all-cis-8,11,14,17-eicosatetraenoic acid (Eicosatetraenoic acid (ETA)), all-cis-5,8,11,14,17-eicosapentaenoic acid (Eicosapentaenoic acid (EPA, Timnodonic acid)), all-cis-6,9,12,15,18-heneicosapentaenoic acid (Heneicosapentaenoic acid (HPA)), all-cis-7,10,13,16,19-docosapentaenoic acid (Docosapentaenoic acid (DPA, Clupanodonic acid)), all-cis-4,7,10,13,16,19-docosahexaenoic acid (Docosahexaenoic acid (DHA, Cervonic acid)), all-cis-9,12,15,18, 21-tetracosapentaenoic acid (Tetracosapentaenoic acid), and all-cis-6,9,12,15,18,21-tetracosahexaenoic acid (Tetracosahexaenoic acid (Nisinic acid)).

According to some embodiments of the invention, the amphipathic carboxylic acid comprises a fibrate.

Fibrates are amphipathic carboxylic acids, which are metabolized by CYP3A4. In addition, fibrates are known for their ability to activate PPAR (peroxisome proliferator-activated receptors), a group of nuclear receptors, especially PPARα.

According to some embodiments of the invention, the fibrate is provided at a concentration in the range of 5 nM to 120 μM, e.g., from 50 nM to 100 μM, e.g., from 100 nM to 50 μM, e.g., from 1 μM to 50 μM, e.g., in the range of 5-30 μM, e.g., in the range of 5-25 μM, e.g., about 5 μM, about 10 μM, about 15 μM, about 20 μM.

According to some embodiments of the invention, the fibrate is selected from the group consisting of Fenofibrate (e.g. TriCor), Bezafibrate (e.g. Bezalip), Ciprofibrate (e.g. Modalim), Clofibrate, Gemfibrozil (e.g. Lopid), and Clinofibrate (e.g. Lipoclin).

According to some embodiments of the invention, the concentration of fenofibrate is between 10-30 μM, e.g., about 20 μM.

According to some embodiments of the invention, the concentration of WY14643 is between 5-20 μM, e.g., about 10 μM.

According to some embodiments of the invention, the concentration of GW7647 is between 5-20 μM, e.g., about 10 μM.

Thiazolidinediones (also known as "Glitazones") are a class of medications that act by activating PPARs (peroxisome proliferator-activated receptors), with greatest specificity for PPARγ (PPAR-gamma, PPARG). The endogenous ligands for these receptors are free fatty acids (FFAs) and eicosanoids.

According to some embodiments of the invention, the Thiazolidinedione is provided at a concentration in the range of about 20 nM to about 120 μM, e.g., from 50 nM to 100 μM, e.g., from 100 nM to 50 μM, e.g., from 1 μM to 50 μM, e.g., in the range of 0.5-30 μM, e.g., in the range of 0.5-25 μM, e.g., about 0.5 μM, about 1 μM, about 5 μM, about 10 μM, about 15 μM.

According to some embodiments of the invention, the Thiazolidinedione is selected from the group consisting of Pioglitazone (Actos), Rosiglitazone (Avandia), Lobeglitazone (Dulie), Troglitazone (Rezulin), Ciglitazone, Darglitazone, Englitazone, Netoglitazone, and Rivoglitazone.

According to some embodiments of the invention, the concentration of rosiglitazone is between 1-10 μM, e.g., about 5 μM.

According to some embodiments of the invention, the concentration of troglitazone is between 0.5-10 μM, e.g., about 0.5-5 μM, e.g., about 1 μM.

According to some embodiments of the invention, the method further comprising contacting the immature hepatocyte with insulin and/or dexamethasone. As used herein the term "insulin" refers to the mature insulin polypeptide having A chain and B chain, which are covalently linked via two disulfide bonds. Also known as CAS Number 11061-68-0; EC Number 234-279-7; MDL number MFCD00131380. The precursor polypeptide preproinsulin is cleaved to remove the precursor signal peptide, and then the proinsulin is post-translationally cleaved into three peptides: the B chain and A chain peptides, which are covalently linked via two disulfide bonds to form insulin, and C-peptide. Binding of insulin to the insulin receptor (INSR) stimulates glucose uptake. There are 4 polypeptide variants, encoding the same protein: variant 1 [GenBank Accession No. NM_000207.2 (SEQ ID NO: 81), GenBank Accession No. NP_000198.1 (SEQ ID NO: 82)], variant 2 [GenBank Accession No. NM_001185097.1 (SEQ ID NO: 83), GenBank Accession No. NP_001172026.1 (SEQ ID NO: 84)]; variant 3 [GenBank Accession No. NM_001185098.1 (SEQ ID NO: 85), GenBank Accession No. NP_001172027.1 (SEQ ID NO: 86)]; and variant 4 [GenBank Accession No. NM_001291897.1 (SEQ ID NO: 87), GenBank Accession No. NP_001278826.1 (SEQ ID NO: 88)]. Insulin can be provided from various suppliers such as Sigma-Aldrich (e.g., recombinant human insulin Catalogue Number 91077C).

According to some embodiments of the invention, the insulin is provided at a concentration of $2.5 \times 10^{-5}$ IU/mL to 1 IU/mL, e.g., between 0.1 IU/mL to about 0.5 IU/mL, e.g., about 0.24 IU/mL. It should be noted that IU/mL is an abbreviation of "International Units Per Millilitre (milliliter)".

Dexamethasone is a corticosteroid medication which can be obtained from various suppliers such as Ark Pharm, Inc., Sigma-Aldrich, Parchem, and AvaChem Scientific.

According to some embodiments of the invention, the dexamethasone is provided at a concentration of about 4 nM to about 100 μM, e.g., between 4 nM to about 200 nM, e.g., between 50-150 nM, e.g., between 70-120 nM, e.g., about 100 nM.

According to some embodiments of the invention, the method further comprising contacting the immature hepatocyte with basic fibroblast growth factor.

Basic fibroblast growth factor (also known as bFGF, FGF2 or FGF-β) is a member of the fibroblast growth factor family. BFGF [(e.g., human bFGF polypeptide GenBank Accession No. NP_001997.5 (SEQ ID NO:69); human bFGF polynucleotide GenBank Accession No. NM_002006.4 (SEQ ID NO:70)] can be obtained from various commercial sources such as Cell Sciences®, Canton, Mass., USA (e.g., Catalogue numbers CRF001A and CRF001B), Invitrogen Corporation products, Grand Island N.Y., USA (e.g., Catalogue numbers: PHG0261, PHG0263, PHG0266 and PHG0264), ProSpec-Tany TechnoGene Ltd. Rehovot, Israel (e.g., Catalogue number: CYT-218), and Sigma, St Louis, Mo., USA (e.g., catalogue number: F0291).

According to some embodiments of the invention, the BFGF is provided at a concentration of 0.1-100 ng/ml, e.g., about 0.2-80 ng/ml, e.g., about 0.4-70 ng/ml. e.g., about 0.5-60 ng/ml, e.g., about 0.8-50 ng/ml, e.g., between about 1 ng/ml to about 40 ng/ml, e.g., about 1-10 ng/ml, e.g., about 2-8 ng/ml. e.g., about 3-6 ng/ml, e.g., about 4-5 ng/ml. e.g., about 4 ng/ml.

According to some embodiments of the invention, the method further comprising contacting the immature hepatocyte with hepatocyte growth factor (HGF).

Hepatocyte growth factor (HGF) is a protein that binds to the hepatocyte growth factor receptor to regulate cell growth, cell motility and morphogenesis in numerous cell and tissue types. Alternative splicing results in multiple transcript variants, at least one of which encodes a preproprotein that is proteolytically processed to generate alpha and beta chains, which form the mature heterodimer. HGF is secreted by mesenchymal cells and acts as a multi-functional cytokine on cells of mainly epithelial origin. Transcription of the HGF gene (Gene ID: 3082) results in 5 isoforms: HGF isoform 1 preproprotein [mRNA GenBank Accession No. NM_000601.5 (SEQ ID NO: 71), polypeptide GenBank Accession No. NP_000592.3 (SEQ ID NO:72); HGF isoform 2 precursor [mRNA GenBank Accession No. NM_001010931.2 (SEQ ID NO: 73), polypeptide GenBank Accession No. NP_001010931.1 (SEQ ID NO: 74)], HGF isoform 3 preproprotein [mRNA GenBank Accession No. NM_001010932.2 (SEQ ID NO: 75), polypeptide GenBank Accession No. NP_001010932.1 (SEQ ID NO:76)], HGF isoform 4 precursor [mRNA GenBank Accession No. NM_001010933.2 (SEQ ID NO: 77), polypeptide GenBank Accession No. NP_001010933.1 (SEQ ID NO: 78)], HGF isoform 5 precursor [mRNA GenBank Accession No. NM_001010934.2 (SEQ ID NO: 79), polypeptide GenBank Accession No. NP_001010934.1 (SEQ ID NO: 80)]. Known suppliers of HGF include PeproTech® Rocky Hill, N.J. USA [e.g., recombinant human HGF (HEK293 derived), Catalogue Number 100-39H], LSBio LifSpan BioSciences, Inc. [e.g., recombinant human HGF Catalogue Number LS-G27264] and ThermoFisher SCIENTIFIC [e.g., HGF Recombinant Human Protein Catalogue Number PHG0254].

According to some embodiments of the invention, the HGF is provided at a concentration of 0.1 ng/mL to 100 ng/mL, e.g., about 0.2-80 ng/ml, e.g., about 0.4-70 ng/ml. e.g., about 0.5-60 ng/ml, e.g., about 0.8-50 ng/ml, e.g., between about 1 ng/ml to about 40 ng/ml, e.g., about 1-30 ng/ml, e.g., about 2-20 ng/ml. e.g., about 3-15 ng/ml, e.g., about 4-15 ng/ml. e.g., about 10 ng/ml.

Any of the proteinaceous factors used by the method of some embodiments of the invention (e.g., the insulin, bFGF, HGF) can be recombinantly expressed or biochemically synthesized. In addition, naturally occurring proteinaceous factors such as bFGF can be purified from biological samples (e.g., from human serum, cell cultures) using methods well known in the art. It should be noted that for the preparation of an animal contaminant-free culture medium the proteinaceous factor is preferably purified from a human source or is recombinantly expressed.

Biochemical synthesis of the proteinaceous factors of the present invention (e.g., the insulin, bFGF, HGF) can be performed using standard solid phase techniques. These methods include exclusive solid phase synthesis, partial solid phase synthesis methods, fragment condensation and classical solution synthesis.

Recombinant expression of the proteinaceous factors of the present invention can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463. Specifically, the IL6RIL6 chimera can be generated as described in PCT publication WO 99/02552 to Revel M., et al. and Chebath J, et al., 1997, which are fully incorporated herein by reference.

Methods of synthesizing the fatty acids, bile acids, steroids, amphipathic carboxylic acids, Thiazolidinediones (TZD), WY-14643 (Pirinixic Acids), GW409544, GW6471, Leukotriene B4, GW 7647, Perfluorooctanesulfonic Acid, PERFLUOROOCTANOIC ACID, CP-775146, CP-865520, UNII-999KY5ZIGB, and Gemfibrozil are known in the art.

According to some embodiments of the invention, the method is performed in-vitro.

According to some embodiments of the invention, contacting or administering the effective amount of the fatty acid or the small molecule selected from the group consisting of: an amphipathic carboxylic acid, Thiazolidinedione (TZD), WY-14643 (Pirinixic Acid), GW409544, GW6471, Leukotriene B4, GW 7647, Perfluorooctanesulfonic Acid, PERFLUOROOCTANOIC ACID, CP-775146, CP-865520, UNII-999KY5ZIGB, and Gemfibrozil is performed in the absence of an IL6 ligand.

It should be noted that the phrase "absence of the IL6 ligand" does not exclude presence of trace concentrations of the IL6 ligand, i.e., below 5 ng/ml. Thus, for example, the method of increasing the metabolic maturation of an immature hepatocyte or the method of treating the subject diagnosed with the pathology characterized by immature hepatocytes can be performed by contacting or administering an effective amount of the fatty acid or the small molecule selected from the group consisting of: an amphipathic carboxylic acid, Thiazolidinedione (TZD), WY-14643 (Pirinixic Acid), GW409544, GW6471, Leukotriene B4, GW 7647, Perfluorooctanesulfonic Acid, PERFLUOROOCTANOIC ACID, CP-775146, CP-865520, UNII-999KY5ZIGB, and Gemfibrozil in the presence of a trace concentration of an IL6 ligand.

According to some embodiments of the invention, the trace concentration of the IL6 ligand does not exceed 5 ng/ml of the IL6 ligand, e.g., does not exceed 4 ng/ml of the IL6 ligand, e.g., does not exceed 3 ng/ml of the IL6 ligand, e.g., does not exceed 2 ng/ml of the IL6 ligand, e.g., does not exceed 1 ng/ml of the IL6 ligand, e.g., does not exceed 0.1 ng/ml of the IL6 ligand, e.g., does not exceed 0.05 ng/ml of the IL6 ligand, e.g., does not exceed 0.01 ng/ml of the IL6 ligand.

According to some embodiments of the invention, the IL6 ligand is selected from the group consisting of oncostatin M (OSM) or a functional equivalent thereof, interleukin 6 (IL6)

or a functional equivalent thereof, leukemia inhibitory factor (LIF) or a functional equivalent thereof, leptin (OB) or a functional equivalent thereof, Cardiotrophin-1/CT-1 or a functional equivalent thereof, CLC or a functional equivalent thereof, CNTF or a functional equivalent thereof, G-CSF or a functional equivalent thereof, IL-11 or a functional equivalent thereof, IL-31 or a functional equivalent thereof, and Neuropoietin/NP or a functional equivalent thereof.

According to some embodiments of the invention, the IL6 ligand is selected from the group consisting of oncostatin M (OSM), interleukin 6 (IL6), leukemia inhibitory factor (LIF), leptin (OB), Cardiotrophin-1/CT-1, CLC, CNTF, G-CSF, IL-11, IL-31, and Neuropoietin/NP.

According to some embodiments of the invention, the IL6 ligand is oncostatin M (OSM).

According to some embodiments of the invention, the immature hepatocyte is obtained by an in vitro differentiation of an hepatoblast.

The phrase "hepatoblast" refers to an hepatocyte-like cell which expresses alpha-fetoprotein but not albumin.

According to some embodiments of the invention, the in vitro differentiation of the hepatoblast is performed by culturing the hepatoblast for a pre-determined time period in a culture medium which comprises an IL6 ligand.

According to some embodiments of the invention, prior to formation of the hepatoblast the fatty acid and/or the small molecule are absent from a culture comprising the hepatoblast.

According to some embodiments of the invention, the culture medium which comprises the IL6 ligand further comprises dexamethasone, basic fibroblast growth factor (FGF2) and insulin.

Thus, the method of some embodiments of the invention can be used to generate mature hepatocytes, which can be used in various therapeutic applications.

According to an aspect of some embodiments of the invention there is provided a method of treating a subject diagnosed with a pathology characterized by immature hepatocytes, the method comprising administering to the subject an effective amount of a fatty acid or a small molecule selected from the group consisting of: an amphipathic carboxylic acid, Thiazolidinedione (TZD), WY-14643 (Pirinixic Acid), GW409544, GW6471, Leukotriene B4, GW 7647, Perfluorooctanesulfonic Acid, Perfluorooctanoic Acid, CP-775146, CP-865520, UNII-999KY5ZIGB, and Gemfibrozil, thereby increasing the metabolic maturation of the immature hepatocytes and treating the subject.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, preferably human beings at any age which suffer from the pathology. Preferably, this term encompasses individuals who are at risk to develop the pathology.

Non-limiting examples of pathologies characterized by an immature hepatocyte include, hyperbilirubinemia (newborn jaundice), as well as pre-term infants, infants born by C-section and the like.

As described in the Examples section which follows, the present inventors have uncovered that the metabolic maturation of the immature hepatocyte can be also increased using PXR agonist under conditions devoid of an IL6 ligand.

According to an aspect of some embodiments of the invention there is provided a method of increasing metabolic maturation of an immature hepatocyte, the method comprising contacting an immature hepatocyte which expresses alpha-fetoprotein (AFP) and albumin with a medium which is devoid of an IL6 ligand and which comprises an effective amount of a PXR agonist selected from the group consisting of: a small molecule, a bile acid, and a steroid, thereby increasing the metabolic maturation of the immature hepatocyte, wherein the effective amount of the PXR agonist increases the expression of a PXR target gene selected from the group consisting of: CYP3A4 and CYP2C9 by at least 2-folds.

As used herein the term "PXR" refers to the pregnane X receptor (PXR) (also known as NR1/2), a nuclear receptor controlling the expression of CYP450 enzymes such as CYP2C9 and CYP3A4.

The primary function of the PXR nuclear receptor is to sense the presence of foreign toxic substances and in response up regulate the expression of proteins involved in the detoxification and clearance of these substances from the body. PXR is a transcriptional regulator of the cytochrome P450 gene CYP3A4, binding to the response element of the CYP3A4 promoter as a heterodimer with the 9-cis retinoic acid receptor RXR.

PXR is activated by a large number of endogenous and exogenous chemicals including steroids (e.g., progesterone, 17α-hydroxyprogesterone, 17α-hydroxypregnenolone, 5α-dihydroprogesterone, 5β-dihydroprogesterone, allopregnanolone, corticosterone, cyproterone acetate, spironolactone, dexamethasone, mifepristone), antibiotics (e.g., rifampicin, rifaximin), antimycotics, bile acids, hyperforin (a constituent of the herbal antidepressant St. John's Wort), and many herbal and other compounds (e.g., meclizine, paclitaxel).

As used herein the phrase "bile acid" refers to a steroid acid found predominantly in the bile of mammals and other vertebrates.

A steroid is an organic compound with four rings arranged in a specific configuration. The steroid core structure is composed of seventeen carbon atoms, bonded in four "fused" rings: three six-member cyclohexane rings and one five-member cyclopentane ring. Steroids vary by the functional groups attached to this four-ring core and by the oxidation state of the rings. Sterols are forms of steroids with a hydroxyl group at position three and a skeleton derived from cholestane. They can also vary more markedly by changes to the ring structure (for example, ring scissions which produce secosteroids such as vitamin D3).

Examples of steroids include, but are not limited to the dietary lipid cholesterol, the sex hormones estradiol and testosterone and the anti-inflammatory drug dexamethasone. Steroids have two principal biological functions: certain steroids (such as cholesterol) are important components of cell membranes which alter membrane fluidity, and many steroids are signaling molecules which activate steroid hormone receptors. Hundreds of steroids are found in plants, animals and fungi. All steroids are manufactured in cells from the sterols lanosterol (animals and fungi) or cycloartenol (plants). Lanosterol and cycloartenol are derived from the cyclization of the triterpene squalene.

Non-limiting examples of bile acids which can be used according to the method of some embodiments of the invention include, lithocolic acid (LCA), Chenodeoxycholic acid (CDCA), cholic acid, deoxycholic acid, ursodeoxycholic acid, or their derivatives.

According to some embodiments of the invention, the bile acid is lithocolic acid (LCA).

According to some embodiments of the invention, the bile acid is Chenodeoxycholic acid (CDCA).

According to some embodiments of the invention, the bile acid is provided at a concentration range of 1 µM to about 250 µM, e.g., between about 1 µM to about 200 µM, e.g., in the range of 2-20 µM, e.g., 5-15 µM, e.g., 7-12 µM, e.g., about 10 µM; additionally or alternatively in the range of 50-200 µM, e.g., 70-150 µM, e.g., 80-120 µM, e.g., about 100 µM.

According to some embodiments of the invention, the concentration of lithocolic acid (LCA) is between 1-20 µM, e.g., about 5-15 µM, e.g., about 10 µM.

According to some embodiments of the invention, the concentration of Chenodeoxycholic acid (CDCA) is between 50-200 µM, e.g., 70-150 µM, e.g., 80-120 µM, e.g., about 100 µM.

According to some embodiments of the invention, the PXR agonist small molecule is selected from the group consisting of: Rifampicin, TO901317, SR12813, mevastatin, rifaximin, hyperforin, meclizine, paclitaxel, atorvastatin, pregnenolone-16alpha-carbonitrile, Butamben and 24(S), 25-Epoxycholesterol.

According to some embodiments of the invention, the concentration of the small molecule PXR agonist is from about 50 nM to about 100 µM, e.g., from about 100 nM to about 80 µM, e.g., from 500 nM to about 80 µM, e.g., from about 700 nM to about 70 µM, e.g., from about 1 µM to about 50 µM, e.g., about 1-5 µM, e.g., about 10-60 µM, e.g., about 1 µM, e.g., about 50 µM.

According to some embodiments of the invention, the concentration of SR12813 is about 0.5-5 µM, e.g., about 0.8-4 µM, e.g., about 0.8-2 µM, e.g., about 1 µm.

According to some embodiments of the invention, the concentration of rifampicin is about 1-60 µM, e.g., about 5-50 µM, e.g., about 10-30 µM, e.g., about 20-30 µM, e.g., about 25 µM.

According to some embodiments of the invention, the PXR agonist steroid is selected from the group consisting of progesterone, 17α-hydroxyprogesterone, 17α-hydroxypregnenolone, 5α-dihydroprogesterone, 5β-dihydroprogesterone, allopregnanolone, corticosterone, cyproterone acetate, spironolactone, dexamethasone, and mifepristone.

According to some embodiments of the invention, the concentration of the steroid PXR agonist is in the range of about 1 µM to about 100 µM, e.g., about 1-50 µM, e.g., about 1-30 µM, e.g., about 1-20 µM, e.g., about 1-10 µM, e.g., about 5 µM, e.g., about 7 µM.

According to some embodiments of the invention, the effective amount of the PXR agonist causes differentiation of said immature hepatocyte into a mature hepatocyte.

Methods of monitoring the differentiation state of an hepatocyte are known in the art, and include for example RNA detection methods (e.g., RT-PCR, quantitative RT-PCR, in situ hybridization, in-situ RT-PCR), proteins detection methods [e.g., Enzyme linked immunosorbent assay (ELISA); Western blot; Radio-immunoassay (RIA); Fluorescence activated cell sorting (FACS); Immunohistochemical analysis; Immuno-fluorescence analysis; in situ activity assay; in vitro activity assays] and morphological evaluations.

According to some embodiments of the invention, the mature hepatocyte is characterized by an albumin$^+$/CY3A4$^+$/E-cadherin$^-$/OCT4$^-$/SOX2$^-$/A1AT$^+$/HNF4α$^+$ expression signature.

According to some embodiments of the invention, the effective amount of the PXR agonist is provided in a concentration of at least half maximal effective concentration ($EC_{50}$) of the PXR agonist.

According to some embodiments of the invention, the PXR agonist is selected from the group consisting of: a small molecule and a bile acid.

It should be noted that the increase in the level of expression of the PXR target genes is compared to the level of expression of the PXR target genes in a control immature hepatocyte before being treated by the method of some embodiments of the invention using identical assay conditions.

According to some embodiments of the invention the increase in the level of expression of the PXR target gene is by at least 2-folds, e.g., at least 3-folds, e.g., at least 4-folds, e.g., at least 5-folds, e.g., at least 6-folds, e.g., at least 7-folds, e.g., at least 8-folds, e.g., at least 9-folds, e.g., at least 10-folds, e.g., at least 11-folds, e.g., at least 12-folds, e.g., at least 13-folds, e.g., at least 14-folds, e.g., at least 15-folds, e.g., at least 16-folds or more as compared to the level of expression of the PXR target gene before being subjected to the conditions of the method of some embodiments of the invention using identical assay conditions.

Methods of detecting the level of expression of the PXR target gene CYP3A4 and CYP2C9 in a cell are known in the art and include for example, RNA and/or protein detection methods, using for example, an antibody specifically bindable to the CYP3A4 or CYP2C9 protein, or with a probe specifically hybridizable with the CYP3A4 or CYP2C9 RNA sequence.

For example, the level of CYP3A4 can be detected using any of the following antibodies: Anti-CYP3A4/Cytochrome P450 3A4 Antibody (clone 3H8) LS-C169171 (LSBio, LifeSpan BioSciences, Inc); Anti-CYP3A4/Cytochrome P450 3A4 Antibody (Biotin) LS-C36104 (LSBio); Anti-CYP3A4/Cytochrome P450 3A4 Antibody IHC-Plus™ LS-B12328 (LSBio).

For example, the level of CYP2C9 can be detected using any of the following antibodies: CYP2C9 polyclonal antibody (ThermoFisher Scientific, Catalogue numbers PA5-15037; PA5-15046; or PA1-84219), or anti-CYP2C9 antibody (Cytochrome P450, Family 2, Subfamily C, Polypeptide 9) (Middle Region) (Antibodies-online(dot)com, Cat. No. ABIN360247).

According to an aspect of some embodiments of the invention, there is provided a method of treating a subject diagnosed with a pathology characterized by immature hepatocytes, the method comprising administering to the subject a pharmaceutical composition comprising an effective amount of a PXR agonist selected from the group consisting of: a small molecule, a bile acid, and a steroid, wherein said pharmaceutical composition is devoid of an IL6 ligand, wherein said effective amount of said PXR agonist increases the expression of a PXR target gene selected from the group consisting of: CYP3A4 and CYP2C9 by at least 2-folds, thereby increasing the metabolic maturation of said immature hepatocytes and treating the subject.

According to an aspect of some embodiments of the invention, there is provided an isolated immature hepatocyte obtainable by the in vitro method of some embodiments of the invention and being characterized by an alpha-fetoprotein (AFP)⁺/Albumin⁺/CYP3A7⁺/SOX2⁻/OCT4⁻ expression signature, production of at least 1 µg Albumin/ml/mg cellular protein and production of at least 25 µg AFP/ml/mg cellular protein.

Methods of determining the level of expression of AFP, albumin, CYP3A7, SOX2 or OCT4 are well known in the art and include RNA and/or protein detection methods. Suitable antibodies include, but are not limited to, Anti-alpha 1 Fetoprotein antibody [AFP-01] (ab3980; abcam); Anti-Albumin antibody [EPSISR1] (ab137885; abcam); CYP3A7 Monoclonal Antibody (F19 P2 H2) (ThermoFisher Scientific Catalogue number MA3-034); Anti-Sox2 Antibody (Chemicon, AB5603); or Anti-POU5F1/OCT4 Antibody IHC-Plus™ LS-B4194 (LSBio LifeSpan BioScience, Inc.).

According to some embodiments of the invention, the hepatoblast is obtainable by a method which comprises:

(a) culturing undifferentiated pluripotent stem cells in a medium which comprises activin A, B27, Wnt3A and hepatocyte growth factor (HGF) to thereby obtain cells characteristics of a definitive endoderm, and subsequently;

(b) culturing the cells characteristics of the definitive endoderm in a culture medium which comprises Dimethyl sulfoxide (DMSO), to thereby obtain the hepatoblasts.

According to some embodiments of the invention, step (b) of the method of obtaining the hepatoblast further comprises passaging the cells at least once in the culture medium which comprises the DMSO.

According to an aspect of some embodiments of the invention there is provided an isolated hepatoblast obtainable by the method of some embodiments of the invention.

According to some embodiments of the invention, the method of increasing metabolic maturation of the immature hepatocyte results in a mature hepatocyte characterized by an albumin⁺/CY3A4⁺/E-cadherin⁺/OCT4⁻/SOX2⁻/A1AT⁺/HNF4α⁺ expression signature.

Methods of determining the level of expression of albumin, CY3A4, E-cadherin, SOX2, OCT4, A1AT, or HNF4α are well known in the art and include RNA and/or protein detection methods. Suitable antibodies include, but are not limited to, Anti-Albumin antibody [EPSISR1] (ab137885; abcam); Anti-Cytochrome P450 3A4 (CYP3A4) antibody (ab135813, abcam); Anti-E Cadherin antibody (ab15148, abcam); Anti-Sox2 Antibody (Chemicon, AB5603); Anti-POU5F1/OCT4 Antibody IHC-Plus™ LS-B4194 (LSBio LifeSpan BioScience, Inc.); Anti-alpha 1 Antitrypsin (A1AT) antibody [G11] (ab9400, abcam); Anti-HNF-4-alpha (HNF4α) antibody [K9218]—ChIP Grade (ab41898, abcam); or HNF-4α Antibody (H-171) (Santa Cruz catalogue number: sc-8987).

According to some embodiments of the invention, the mature hepatocyte is capable of producing at least 10 µg albumin per milliliter per milligram of cellular protein, e.g., at least 15 µg albumin/ml/mg cellular protein.

According to an aspect of some embodiments of the invention there is provided an isolated hepatocyte obtainable by the method according to the method of some embodiments of the invention.

According to an aspect of some embodiments of the invention, there is provided an isolated hepatocyte characterized by a Cytochrome P450 3A4 (CYP3A4) activity which is capable of oxidizing at least 1 pmol of 7-benzyloxy-4-trifluoromethylcoumarin (BFC) per minute per milligram of cellular protein and an alpha feto-protein (AFP) activity of at least 60 µg/day/mg cellular protein as assayed by ELISA when cultured in the presence of a culture medium which comprises Insulin-Transferrin-Selenium (ITS), Glutamax, Dexamethasone, hepatocyte growth factor (HGF), Oleic acid and 9CLA.

According to some embodiments of the invention, the isolated hepatocyte of some embodiments of the invention is characterized by a Cytochrome P450 3A4 (CYP3A4) activity which is capable of oxidizing at least 1 pmol of 7-benzyloxy-4-trifluoromethylcoumarin (BFC) per minute per milligram of cellular protein.

According to some embodiments of the invention, the isolated hepatocyte of some embodiments of the invention is characterized by an alpha-fetoprotein (AFP) production of at least 60 microgram per day per milligram cellular protein as determined by an ELISA.

According to some embodiments of the invention, the isolated hepatocyte of some embodiments of the invention is characterized by nuclear expression of PXR.

It should be noted that the isolated hepatocyte of some embodiments of the invention is distinguishable from an adult hepatocyte by at least the expression of AFP.

The phrase "adult hepatocyte" refers to an hepatocyte cell which produces albumin and which does not express alpha-fetoprotein (AFP). It should be noted that an adult hepatocyte is also characterized by the expression of cytochrome 3A4 (CYP3A4).

According to an aspect of some embodiments of the invention, there is provided an isolated population of cells wherein at least about 50% of the cells comprise the isolated hepatocyte of some embodiments of the invention.

According to some embodiments of the invention, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, e.g., at least 71%, 72%, 73%, 74%, 75%, 76%, 77%, 78%, 79%, 80%, 81%, 82%, 83%, 84%, 85% of the cells in the population are the isolated hepatocytes of some embodiments of the invention.

According to an aspect of some embodiments of the invention there is provided a method of screening a compound for liver toxicity, comprising:

(a) incubating the isolated population of cells of some embodiments of the invention with the compound for a pre-determined time period;

(b) determining percentage of a parameter indicative of liver toxicity following the pre-determined time period, thereby screening the compound for the liver toxicity.

According to some embodiments of the invention, the liver toxicity comprises steatosis.

According to some embodiments of the invention, the steatosis is assayable using the LipidTox neutral lipid stain.

According to some embodiments of the invention, the liver toxicity comprises cholestasis.

According to some embodiments of the invention, the cholestasis is assayable using the CDFDA (5(6)-carboxy-2', 7'-dichlorofluorescein diacetate) staining.

According to some embodiments of the invention, the liver toxicity comprises apoptosis.

According to some embodiments of the invention, the apoptosis is assayable using the Terminal deoxynucleotidyl transferase dUTP nick end labeling TUNEL assay.

According to an aspect of some embodiments of the invention there is provided a kit for screening a compound for liver toxicity comprising the isolated population of cells of some embodiments of the invention and at least one agent capable of detecting a toxicological end-point selected from the group consisting of: steatosis, cholestasis and apoptosis.

According to an aspect of some embodiments of the invention there is provided a nutrition formula for an infant comprising 9CLA.

According to some embodiments of the invention the nutrition formula is an infant formula.

According to some embodiments of the invention, the concentration of the 9CLA in the nutrition formula is between about 70 mg/100 kJ to about 330 mg/100 kJ of formula.

According to some embodiments of the invention, the concentration of the 9CLA in the nutrition formula is between about 400-800 mg 9CLA per 100 ml of ready-to-use nutrition formula, e.g., between about 500-700 mg 9CLA per 100 ml of ready-to-use nutrition formula, e.g., about 500-650 mg 9CLA per 100 ml of ready-to-use nutrition formula.

According to some embodiments of the invention, the concentration of the 9CLA in the nutrition formula is between about 3-5 grams 9CLA per 100 grams of powder of the nutrition formula, e.g., between about 3.5-4.5 grams 9CLA per 100 grams of powder of the nutrition formula, e.g., between about 3.8-4.2 grams 9CLA per 100 grams of powder of the nutrition formula.

According to some embodiments of the invention, the nutrition formula is for use in a subject having a pathology characterized by immature hepatocytes, such as hyperbilirubinemia (newborn jaundice), pre-term infants, infants born by C-section and the like.

According to some embodiments of the invention, the nutrition formula of some embodiments of the invention is suitable for infants born by C-section (Caesarean section).

According to some embodiments of the invention, the nutrition formula of some embodiments of the invention is suitable for a non-breast fed infant.

According to some embodiments of the invention, the nutrition formula of some embodiments of the invention is suitable for at least the first week(s) of life, e.g., for at least one week of life, e.g., for at least two, at least three, for at least four, for at least five weeks of life.

The nutrition formula can be in a form of a powder that comprises 9CLA and can be combined with a liquid, such as water, to produce a milk-like beverage to be used by a subject in need thereof, or it can be in a liquid form (e.g., ready to use solution or suspension), e.g., for use by a subject diagnosed by or having a pathology characterized by immature hepatocytes.

According to some embodiments of the invention, the powder and resulting beverage have a balanced amino acid profile suitable for dietary management of individuals diagnosed by or having a pathology characterized by immature hepatocytes.

The nutrition formula of some embodiments of the invention may also include (a) complementary essential amino acids which are a mixture of tyrosine, arginine, tryptophan, leucine and histidine and, in combination, provide a balanced amino acid profile and (b) a carbohydrate source, which typically includes non-reducing sugars to minimize/reduce browning potential.

The nutrition formula of some embodiments of the invention may also include (a) complementary essential amino acids which are a mixture of tyrosine, arginine, tryptophan, leucine and histidine and, in combination, provide a balanced amino acid profile; (b) a carbohydrate source, which typically includes non-reducing sugars to minimize/reduce browning potential; and (c) a fat (lipid/oil) source.

The nutrition formula of some embodiments of the invention can further comprise vitamins and minerals, such as vitamins and minerals in sufficient quantities to meet the daily requirement for each.

The nutrition formula of some embodiments of the invention may also include (a) complementary essential amino acids which are a mixture of tyrosine, arginine, tryptophan, leucine and histidine and, in combination, provide a balanced amino acid profile; (b) a carbohydrate source, which typically includes non-reducing sugars to minimize/reduce browning potential; (c) a fat (lipid/oil) source [e.g., PUFA (Polyunsaturated fatty acids) such as DHA (Docosahexaenoic acid) and ARA (Arachidonic Acid)]; and typically, but optionally, (d) vitamins and minerals, such as vitamins and minerals in sufficient quantities to meet the daily requirements for each.

In addition, the nutrition formula typically, but optionally, includes flavors, which can be natural or artificial or a combination of both; coloring agents, which can be natural or artificial or a combination of both; sweetener, which can be natural or artificial or a combination of both; gelling agents, thickening agents, stabilizing agents, sequestrants, emulsifiers or a combination of two or more of gelling agents, thickening agents, stabilizing agents, sequestrants, emulsifiers, each of which can be natural or artificial or a combination of both.

Table 1, herein below, provides sequence information of the polypeptides/polynucleotides used in the methods of some embodiments of the invention.

TABLE 1

| Protein name | Representative GenBank Accession No. of protein | SEQ ID NO: of the protein | Representative GenBank Accession No. of the mRNA encoding the protein | SEQ ID NO: of the mRNA |
| --- | --- | --- | --- | --- |
| Alpha-fetoprotein (AFP) | NP_001125.1 | 1 | NM_001134.2 | 12 |
| cytochrome 3A7 (CYP3A7) cytochrome P450 family 3 subfamily A member 7 | NP_000756.3 | 2 | NM_000765.4 | 13 |
| cytochrome 3A4 (CYP3A4) cytochrome P450 family 3 subfamily A | NP_001189784.1 | 3 | NM_001202855.2 | 14 |

TABLE 1-continued

| Protein name | Representative GenBank Accession No. of protein | SEQ ID NO: of the protein | Representative GenBank Accession No. of the mRNA encoding the protein | SEQ ID NO: of the mRNA |
|---|---|---|---|---|
| member 4 isoform 2 | | | | |
| cytochrome 3A4 (CYP3A4) cytochrome P450 family 3 subfamily A member 4 isoform 1 | NP_059488.2 | 4 | NM_017460.5 | 15 |
| insulin | NP_000198.1 | 65 | NM_000207.2 | 66 |
| basic fibroblast growth factor | NP_001997.5 | 67 | NM_002006.4 | 68 |
| hepatocyte growth factor (HGF) isoform 1 | NP_000592.3 | 5 | NM_000601.5 | 16 |
| hepatocyte growth factor (HGF) isoform 2 | NP_001010931.1 | 6 | NM_001010931.2 | 17 |
| hepatocyte growth factor (HGF) isoform 3 | NP_001010932.1 | 7 | NM_001010932.2 | 18 |
| hepatocyte growth factor (HGF) isoform 4 | NP_001010933.1 | 8 | NM_001010933.2 | 19 |
| hepatocyte growth factor (HGF) isoform 5 | NP_001010934.1 | 9 | NM_001010934.2 | 20 |
| HSP60 (heat shock protein family D (Hsp60) member 1) variant 1 | NP_002147.2 | 10 | NM_002156.4 | 21 |
| HSP60 (heat shock protein family D (Hsp60) member 1) variant 2 | NP_955472.1 | 11 | NM_199440.1 | 22 |

Table 2 hereinbelow provides a non-limiting list of conjugated fatty acids which can be used according to some embodiments of the invention.

TABLE 2

Conjugated Fatty acids

| Common name | Lipid name | Chemical name |
|---|---|---|
| Conjugated Linoleic Acids (two conjugated double bonds) | | |
| Rumenic acid | 18:2 (n-7) | 9Z,11E-octadeca-9,11-dienoic acid |
| | 18:2 (n-6) | 10E,12Z-octadeca-9,11-dienoic acid |
| Conjugated Linolenic Acids (three conjugated double bonds) | | |
| α-Calendic acid | 18:3 (n-6) | 8E,10E,12Z-octadecatrienoic acid |
| β-Calendic acid | 18:3 (n-6) | 8E,10E,12E-octadecatrienoic acid |
| Jacaric acid | 18:3 (n-6) | 8Z,10E,12Z-octadecatrienoic acid |
| α-Eleostearic acid | 18:3 (n-5) | 9Z,11E,13E-octadeca-9,11,13-trienoic acid |
| β-Eleostearic acid | 18:3 (n-5) | 9E,11E,13E-octadeca-9,11,13-trienoic acid |
| Catalpic acid | 18:3 (n-5) | 9Z,11Z,13E-octadeca-9,11,13-trienoic acid |
| Punicic acid | 18:3 (n-5) | 9Z,11E,13Z-octadeca-9,11,13-trienoic acid |
| Other | | |
| Rumelenic acid | 18:3 (n-3) | 9E,11Z,15E-octadeca-9,11,15-trienoic acid |
| α-Parinaric acid | 18:4 (n-3) | 9E,11Z,13Z,15E-octadeca-9,11,13,15-tetraenoic acid |
| β-Parinaric acid | 18:4 (n-3) | all trans-octadeca-9,11,13,15-tretraenoic acid |
| Bosseopentaenoic acid | 20:5 (n-6) | 5Z,8Z,10E,12E,14Z-eicosanoic acid |

Table 2: List of conjugated fatty acids

Table 3 hereinbelow, provides a non-limiting list of omega 3 polyunsaturated fatty acids which can be used according to some embodiments of the invention.

TABLE 3

List of omega 3 polyunsaturated fatty acids

| Common name | Lipid name | Chemical name |
|---|---|---|
| Hexadecatrienoic acid (HTA) | 16:3 (n-3) | all-cis 7,10,13-hexadecatrienoic acid |
| Alpha-linolenic acid (ALA) | 18:3 (n-3) | all-cis-9,12,15-octadecatrienoic acid |
| Stearidonic acid (SDA) | 18:4 (n-3) | all-cis-6,9,12,15,-octadecatetraenoic acid |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic | 20:5 (n-3) | all-cis-5,8,11,14,17- |

TABLE 3-continued

List of omega 3 polyunsaturated fatty acids

| Common name | Lipid name | Chemical name |
|---|---|---|
| acid (EPA, Timnodonic acid) | | eicosapentaenoic acid |
| Heneicosapentaenoic acid (HPA) | 21:5 (n-3) | all-cis-6,9,12,15,18-heneicosapentaenoic acid |
| Docosapentaenoic acid (DPA, Clupanodonic acid) | 22:5 (n-3) | all-cis-7,10,13,16,19-docosapentaenoic acid |
| Docosahexaenoic acid (DHA, Cervonic acid) | 22:6 (n-3) | all-cis-4,7,10,13,16,19-docosahexaenoic acid |
| Tetracosapentaenoic acid | 24:5 (n-3) | all-cis-9,12,15,18,21-tetracosapentaenoic acid |
| Tetracosahexaenoic acid (Nisinic acid) | 24:6 (n-3) | all-cis-6,9,12,15,18,21-tetracosahexaenoic acid |

Table 3

Table 4 hereinbelow, provides a non-limiting list of small molecules which are ligands or agonist of PPARA.

TABLE 4

Small molecules which are ligands or agonist of PPARA

| Name | Description | CAS Registry ID |
|---|---|---|
| GW409544 | L-tyrosine analog (Synonyms GW 9544) | |
| GW6471 | An extended amide analog | 436159-64-7 |
| Pirinixic acid | Hypolipidemic drug (Synonyms WY-14643) | 50892-23-4 |
| Leukotriene B4 | biologically active lipid mediator | 71160-24-2 |
| GW 7647 | Selective PPARA agonist | 265129-71-3 |
| Perfluorooctanesulfonic Acid | Fluorosurfactant (Synonyms PFOS) | 1763-23-1 |
| PERFLUOROOCTANOIC ACID | Fluorosurfactant (Synonyms PFOA) | 335-67-1 |
| CP-775146 | Not Available | PubChem ID 10410059 |
| CP-865520 | Not Available | PubChem ID 10050146 |
| UNII-999KY5ZIGB | Not Available | 702681-67-2 |
| Gemfibrozil | fibric acid derivative (Synonyms Decrelip; Jezil; Lipur; Lopid) | 25812-30-0 |

Table 4.

The agents described hereinabove for increasing metabolic maturation of an immature hepatocyte can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agents accountable for the biological effect [e.g., a fatty acid; a small molecule selected from the group consisting of: an amphipathic carboxylic acid, Thiazolidinedione (TZD), WY-14643 (Pirinixic Acid), GW409544, GW6471, Leukotriene B4, GW 7647, Perfluorooctanesulfonic Acid, PER-FLUOROOCTANOIC ACID, CP-775146, CP-865520, UNIT-999KY5ZIGB, and Gemfibrozil; a PXR agonist selected from the group consisting of: a small molecule, a bile acid, and a steroid].

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients [e.g., a fatty acid; a small molecule selected from the group consisting of: an amphipathic carboxylic acid, Thiazolidinedione (TZD), WY-14643 (Pirinixic Acid), GW409544, GW6471, Leukotriene B4, GW 7647, Perfluorooctanesulfonic Acid, PERFLUOROOCTANOIC ACID, CP-775146, CP-865520, UNII-999KY5ZIGB, and Gemfibrozil; a PXR agonist selected from the group consisting of: a small molecule, a bile acid, and a steroid] effective to prevent, alleviate or ameliorate symptoms of a disorder (e.g., a pathology characterized by an immature hepatocyte) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide tissue levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Compositions of some embodiments of the invention, including the agents, the pharmaceutical compositions, and/or the nutrition formula of some embodiments of the invention may be included in an article of manufacture preferably along with appropriate instructions for use and labels indicating FDA approval, Food and Agriculture Organization of the United Nations approval, and/or the World Health Organization approval for use in treating a subject having immature hepatocytes.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 12 is expressed in a DNA sequence format (e.g., reciting T for thymine), but it can refer to either a DNA sequence that corresponds to an alpha-fetoprotein nucleic acid sequence, or the RNA sequence of an alpha-fetoprotein RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Cells and Cell Cultures—

13 hESCs (Amit M, et al. Clonally derived human embryonic stem cell lines maintain pluripotency and proliferative potential for prolonged periods of culture. Dev Biol 2000; 227:271-278) or HUES8 hESC were grown in a feeder-independent system (i.e., in suspension cultures) as previously described (Amit M, et al. Suspension culture of undifferentiated human embryonic and induced pluripotent stem cells. Stem Cell Rev 2010; 6:248-259). In brief, cells were removed from culture dishes using collagenase type IV, separated into small clumps using 200 µl tips, and cultured in suspension in 58 mm Petri dishes at a cell density of 1-5×10$^6$ cells/ml. The Petri dishes were kept static in an incubator at 37° C. in 5% $CO_2$. After 3 passages of adaptation to suspension, cells were transferred to spinner flasks, with a speed of 75 RPM. Culture medium was changed every other day, and the cells were diluted in a ratio of 1:4 every 5-7 days. The cells were kept in culture medium (Y10F) consisting of 85% DMEM/F12 (Biological Industries, Beit Haemek, Israel), 15% knockout serum replacement, 2 mM L-glutamine, 0.1 mM β-mercaptoethanol, 1% non-essential amino acid stock, 500 U/mL penicillin and 1 mg/mL streptomycin (Sigma-Aldrich, St. Louis, Mo.), 10 ng/ml bFGF (R&D systems, Minneapolis, Minn.) and supplemented with 100 pg/ml IL6-IL6 receptor chimera.

Prior to differentiation, 13 hESC or HUES8 hESC were cultured on growth factor reduced Matrigel™ (BD Biosceinces, San Jose, Calif.) in mTeSR-1 media (Stemcell technologies, Vancouver, Canada) supplemented with 500 U/mL penicillin and 1 mg/mL streptomycin (Biological Industries, Beit Haemek, Israel). Cells were passaged using Accutase™ (Sigma Aldrich, St Louis, Mo.).

Cryopreserved human hepatocytes (Gibco, Lot number Hu8132) were thawed and plated on growth factor reduced Matrigel™ in Hepatocyte Maintenance Medium (HMM) per manufacturer instructions (Lonza, Cologne, Germany).

Human Subjects—

All protocols involving human tissue were reviewed and exempted by the Hebrew University of Jerusalem and Weill Cornell Medical College Institutional Review Boards.

hESC Hepatic Differentiation—

The first steps of the differentiation protocol are similar to those previously reported by Hay et al. (Hay D C, et al. Highly efficient differentiation of hESCs to functional hepatic endoderm requires ActivinA and Wnt3a signaling. Proc Natl Acad Sci USA 2008; 105:12301-12306) and Chen et al. (Chen Y F, et al. Rapid generation of mature hepatocyte-like cells from human induced pluripotent stem cells by an efficient three-step protocol. Hepatology 2012; 55:1193-1203), each of which is fully incorporated herein by reference in its entirety.

In brief, cells were seeded on Matrigel™-coated plates in mTeSR-1 medium and allowed to reach 50% confluence.

Stage 1:

In the first three days, cells were cultured in RPMI-1640, supplemented with B27 supplement (Gibco, Grand Island, N.Y.), 100 ng/ml activin A (R&D Systems, Minneapolis, Minn.), 50 ng/ml Wnt3A (R&D Systems) and 10 ng/ml HGF (hepatocyte growth factor) (PeproTech, London, UK).

Stage 2:

In the following four days, cells were cultured in Knock-Out DMEM (Gibco) supplemented with 20% KnockOut serum replacement (Gibco), 1% non-essential amino acids (Biological Industries, Beit Haemek, Israel), 1 mM L-glutamine (Biological Industries), 0.1 mM 2-mercaptoethanol (Sigma Aldrich) and 1% DMSO (Sigma Aldrich).

Stage 3:

In the subsequent five days, cells were cultured in Iscove's modified Dulbecco's medium (IMDM) (Biological Industries) supplemented with 20 ng/ml oncostatin M (R&D Systems), 4 ng/ml FGF2 (PeproTech), Insulin-Transferrin-Selenium (ITS) supplement (Sigma Aldrich) and 0.5 µM Dexamethasone (Sigma Aldrich).

The last stage of differentiation (stage 4) was performed according to the method published in Avior Y., et al., 2015 ("Microbial-derived lithocholic acid and vitamin K2 drive the metabolic maturation of pluripotent stem cells-derived and fetal hepatocytes". Hepatology. 2015 July; 62(1):265-78. Epub 2015 Apr. 22, which is fully incorporated herein by its entirety) as follows: In the last differentiation step, cells were cultured in RPMI-1640 supplemented with 0.5 µM Dexamethasone, 10 ng/ml HGF and ITS+3 supplement (which includes 16.7 µM of LA and OA) (Sigma Aldrich). Final differentiation step was also carried out with 10 µM LCA (Sigma Aldrich) and 10 µM Vitamin $K_2$ (MK4) as described in the text (Sigma Aldrich).

Alternatively, the last stage of differentiation (stage 4) was performed as follows: In the last step, cells were cultured in Williams' medium E (Sigma Aldrich) supplemented with 0.5 µM Dexamethasone, 10 ng/ml HGF (hepatocyte growth factor) and ITS supplement (Sigma Aldrich). Final differentiation step (days 12 to 16) was also carried out with different concentrations of Oleic acid-Albumin from bovine serum (Sigma Aldrich) and linoleic acid-Albumin from bovine serum (Sigma Aldrich). As indicated in the experimental results below, in some experiments linoleic acid was replaced with 9-cis, 11-trans Conjugated linoleic acid (9CLA, Sigma) and 50 µM BSA (bovine serum albumin) was added. Additional details are provided in Tables 5 and 6 herein below.

It should be noted that the optimal concentrations of OA was 100 µM; the optimal concentration of 9CLA was 100 µM; and the optimal concentration of LA was 100 µM.

TABLE 5

Materials for hPSCs differentiation

| Materials for hPSC differentiation | Company | Catalog number |
|---|---|---|
| PBS | Sigma | D8537 |
| RPMI-1640 | Gibco | 21875-034 |
| Penicillin Streptomycin (Pen Strep) | Biological Industries | 03-031-1C |
| B27 supplement | Gibco | 17504044 |
| Activin-A | R&D | 338-AC |
| Wnt-3A | R&D | 5036-WN-010 |
| HGF | Peprotech | 100-39 |
| K/O DMEM | Gibco | 10829018 |
| K/O Serum | Gibco | 10828-028 |
| L-Alanyl-L-Glutamin (Glutamax) | Biological Industries | 030221B |
| Non Essential Amino Acids (NEAA) | Biological Industries | 01-340-1B |
| DMSO (Dimethyl sulfoxide) | Sigma | D4540 |
| β-Mercaptoethanol | Sigma | M6250 |
| Iscove's Modified Dulbecco's Media (IMDM) | Biological Industries | 01-058-1A |
| ITS | Sigma | I3146 |
| Dexamethasone | Sigma | D4902 |
| Oncostatin-M (OSM) | R&D | 295-OM |
| basic-FGF (FGF2) | Peprotech | 100-18B |
| Williams Medium E | Sigma | W1878 |
| Oleic acid - albumin | Sigma | O3008 |
| Linoleic acid - albumin | Sigma | L9530 |
| 9-cis,11-trans, conjugated linoleic acid (9CLA) | Sigma | 16413 |

Table 5. List of materials for hESC differentiation

TABLE 6

Exemplary culture media for specific differentiation stages of human pluripotent stem cells towards hepatocytes

| Stage | | Days | # Media Changes | Media Components |
|---|---|---|---|---|
| S1 | Endodermal Induction | 1-3 | 3 | RPMI 1640 medium, Pen/Strep (100 U), B27 (1X), Act-A (100 ng/ml), Wnt-3a (50 ng/ml), HGF (10 ng/ml) |
| S2 | Hepatic Specification | 4-7 | 4 | K/O DMEM medium, Pen/Strep (100 U), K/O Serum (20%), Glutamax (2 mM), NEAA (1%), DMSO (1%), β-Mercaptoethanol (0.1 mM) |
| S3 | Hepatic Differentiation | 8-12 | 5 | IMDM medium, Pen/Strep (100 U), ITS (1X), Dexamethasone (0.5 µM), Oncostatin M (20 ng/ml), bFGF (4 ng/ml) |
| S4 | Hepatic Maturation | 13-16 | 4 | Williams Medium E or RPMI 1640 medium, Pen/Strep (100 U), ITS (1X), Glutamax (2 mM), Dexamethasone (0.5 µM), HGF (10 ng/ml), Oleic acid (100 µM), 9CLA (100 µM). |

Table 6. hESC differentiation protocol.

Sub-Culturing of the Cells Between Day 5 to 10—

The present inventors have incorporated a sub-culture step on Day 8 of the differentiation method in order to increase proliferation growth and increase differentiation by minimizing contact inhibition. The hESC-H can only be sub-cultured between days 5 to 10 without loss of function such as AFP expression. Cells were washed with PBS and trypsinized off the surface following 2-5 minutes incubation at 37° C. in 5% $CO_2$. Cell suspension was diluted in DMEM containing 10% FBS and centrifuged at 300 g for 5 minutes. Cell pellet was resuspended in $2^{nd}$ stage medium and cells were seeded at 50% confluence on Matrigel coated dished.

Hepatic Differentiation Protocol which Includes the Sub-culturing Step:

Table 7 hereinbelow, summarizes the reagents used in the differentiation protocol

TABLE 7

| Reagent | Supplier | Catalogue number |
|---|---|---|
| PBS | Sigma | D8537 |
| RPMI-1640 | Gibco | 21875-034 |
| Penicillin Streptomycin (Pen Strep) | Biological Industries | 03-031-1C |
| B27 supplement | Gibco | 17504044 |
| Activin-A | R&D | 338-AC |
| Wnt-3A | R&D | 5036-WN-010 |
| HGF | Peprotech | 100-39 |
| K/O DMEM | Gibco | 10829018 |
| K/O Serum | Gibco | 10828-028 |
| L-Alanyl-L-Glutamin (Glutamax) | Biological Industries | 030221B |
| Non Essential Amino Acids (NEAA) | Biological Industries | 01-340-1B |
| DMSO | Sigma | D4540 |
| β-Mercaptoethanol | Sigma | M6250 |
| Growth Factor Reduced Matrigel | BD Biosciences | 356230 |
| DMEM | Gibco | 11965092 |
| Fetal Bovine Serum (FBS) | Biological Industries | |
| Iscove's Modified Dulbecco's Media (IMDM) | Biological Industries | 01-058-1A |
| ITS | Sigma | I3146 |
| Dexamethasone | Sigma | D4902 |
| Oncostatin-M (OSM) | R&D | 295-OM |
| basic-FGF (FGF2) | Peprotech | 100-18B |
| Williams Medium E | Sigma | W1878 |
| Oleic acid - albumin | Sigma | O3008 |
| Linoleic acid - albumin | Sigma | L9530 |
| 9-cis,11-trans, conjugated linoleic acid (9CLA) | Sigma | 16413 |

Table 7.

The differentiation protocol was as follows:

Day 0: Once pluripotent cell culture, passaged with Accutase as single cells, reach 50-60% confluence (which is about 2-3 days if the cells were seeded at a confluence of 20-30%), the cells were washed twice with PBS and then the 51 Medium was added.

Days 1-2: 51 medium was replaced daily with a fresh 51 medium;

Day 3: The cells were washed twice with PBS and a freshly-made warm S2 medium was added;

Days 4-6: The S2 medium was replaced daily with a fresh S2 medium;

Day 7: Sub-culturing stage: When the cells reached over 90% confluence, the cells were passaged as follows. For a 6-well plate (about $10^6$ cells), the wells were washed with PBS, and then with 0.5 ml trypsin for a 2-5 minutes incubation at 37° C. 5% $CO_2$. Then, 1 ml of DMEM medium containing 10% FBS was added to dilute the trypsin, followed by a gentle pipetting of the suspension to obtain single cells. The cells were centrifuged for 5 minutes at 300 g, the medium was removed and the cells were re-suspended in S2 medium. The cells were seeded in a 1:2 or 1:3 ratio on Matrigel coated plates. It should be noted that Trypsin usually dissociates the differentiated cells into single cells, but still some clumps remain. According to this method, the clumps were gently broken using a 5 ml pipet and the cells were evenly distributed between the wells. The use of the 1 ml tip was avoided when sub-culturing.

Day 8: In case some cell death was visible, the plates were washed once with PBS before proceeding to S2 medium change.

Day 9: The cells were washed twice with PBS and a freshly made warm S3 medium was added.

Days 10-13: The S3 medium was replaced daily with a fresh S3 medium.

Day 14: The cells were washed twice with PBS and a freshly made warm S4 medium was added.

Days 15-17: The S4 medium was replaced daily with a fresh S4 medium.

Day 18: At this stage, cell density is about 10 times higher than in day 7. Meaning that in a 6 well there were $5*10^6$ cells at day 18.

Fluorescence-Activated Cell Sorting (FACS)—

Cells were harvested using TrypLE Select (Gibco) and spun down for 5 minutes, then suspended in PBS buffer containing 5% FBS and the conjugated antibodies. Cells were then incubated for 1 hour at room temperature and were washed three times in buffer. Analysis was performed in FACSAria II cell sorter (BD Biosceinces).

Quantitative Real Time Polymerase Chain Reaction (qRT-PCR)—

RNA was isolated and purified using RNeasy mini kit (Qiagen) or NucleoSpin RNA kit (Macherey-Nagel), according to manufacturer protocol. cDNA samples were synthesized using qScriptc DNA Super Mix (Quanta Bio-Sciences), according to manufacturer protocol. 1 µg of purified RNA was used for each reaction, with concentration and purity determined by a ND-1000 spectrophotometer (NanoDrop Technologies). Each reaction was diluted to reach a concentration of 10 ng/µL. Gene expression analysis was carried out utilizing KAPA SYBR FAST Universal 2×qPCR Master Mix (KapaBiosystems, Wilmington, Mass.) on BioRad CFX96 Real-Time System, according to manufacturer protocol. Gene transcription was evaluated using the ΔΔCt method normalized to UBC1 and RPL32 as housekeeping genes (Table 8, hereinbelow).

TABLE 8

| | PCR primers | | | |
|---|---|---|---|---|
| Gene Name | Forward 5'-3'' | SEQ ID NO: | Reverse 3'-5' | SEQ ID NO: |
| ABCG5 | TCTGTTTCCCGTGCTGCGAG | 23 | CCCAGCGTCCAGTAGCACAC | 24 |
| AFP | CCTACAATTCTTCTTTGGGCT | 25 | AGTAACAGTTATGGCTTGGA | 26 |
| Albumin | GGAATGCTGCCATGGAGATCTGC | 27 | CCTTCAGTTTACTGGAGATCG | 28 |
| BAAT | CTCCAAAGGCCAGCCTGACT | 29 | CAGCCCACCCAAACCACCAA | 30 |
| CPT1α | GCCTCGTATGTGAGGCAAA | 31 | CCCATTCGTAGCCTTTGGTA | 32 |
| CYP3A4 | Purchased from Qiagen (QT00067396) | | Purchased from Qiagen (QT00067396) | |
| FIS1 | AAAGTACGTCCGCGGGTTGC | 33 | TCCGATGAGTCCGGCCAGT | 34 |
| FoxA2 | GGGAGCGGTGAAGATGGA | 35 | TCATGTTGCTCACGGAGGAGTA | 36 |
| FXR | Purchased from IDT (Hs.PT.56a.27354436) | | Purchased from IDT (Hs.PT.56a.27354436) | |
| LXRα | GCCGAGTTTGCCTTGCTCA | 37 | TCCGGAGGCTCACCAGTTTC | 38 |
| MFN2 | AAGGTGAAGCGCAATGTCCCT | 39 | CCCCCAGCTGCTCAAAAATGC | 40 |
| PGC1α | TGCTCTGTGTCACTGTGGATTGG | 41 | GGGCAAAGAGGCTGGTCTTCA | 42 |
| PPARα | Purchased from Qiagen (QT00017451) | | Purchased from Qiagen (QT00017451) | |
| PXR | CTCACCTCCAGGTTTGCTTC | 43 | CTCCTTGATCGATCCTTTGC | 44 |
| OCT4 | TCTCCAGGTTGCCTCTCACT | 45 | GTGGAGGAAGCTGACAACAA | 46 |

TABLE 8-continued

PCR primers

| Gene Name | Forward 5'-3'' | SEQ ID NO: | Reverse 3'-5' | SEQ ID NO: |
|---|---|---|---|---|
| OTC | TCGAGCCAATACTG CATCTG | 47 | CTTCTGGGAGGACATCC TTG | 48 |
| SERPINA1 | ACGAGACAGAAGAC GGCATT | 49 | CCCTCTGGATCCACTGC TT | 50 |
| SLC22A1 | CCCCACATTCGTCAG CGGTGT | 51 | AGGTGCCCGAGGGTTCT GAGG | 52 |
| Sox17 | GGCGCAGCAGAATC CAGA | 53 | CCACGACTTGCCCAGCA T | 54 |
| Sox2 | GCTTAGCCTCGTCGA TGAAC | 55 | AACCCAAGATGCACAA CTC | 56 |
| UBC1 | CGGGTGTGGCACAG CTAGTT | 57 | TGCATTGTCAAGTGACG ATCAC | 58 |
| FIS1 | AAAGTACGTCCGCG GGTTGC | 59 | TCCGATGAGTCCGGCCA GT | 60 |
| CYP2C9 | Purchased from IDT (Hs.PT.56a.858384) | | Purchased from IDT (Hs.PT.56a.858384) | |

Alphabetical list of qRT-PCR primers and sequence identifiers.

Immunofluorescence Staining—

Cultured cells were fixed using 4% paraformaldehyde for 15 minutes at room temperature. Cells were then permeabilized in PBS blocking buffer containing 2% BSA and 0.25% Triton X-100 for one hour at room temperature, and incubated with primary antibodies for another hour (Table 9, hereinbelow). Following washes, cells were incubated with secondary antibodies for 1 hour at room temperature in blocking buffer (Table 10, hereinbelow). Hoechst staining was performed using bisBenzimide H33342 for 2 minutes. Imaging was performed on a Zeiss LSM 700 confocal microscope.

TABLE 9

Primary antibodies used for immunofluorescence analysis

| Antibody | Host | Company | Catalog # | Dilution |
|---|---|---|---|---|
| AFP | Rabbit | Cell Marque | 203A-16 | 1:100 |
| Albumin | Chicken | ICL | CAL80A | 1:100 |
| FoxA2 | Rabbit | Abcam | AB40874 | 1:100 |
| Gata4 | Rabbit | Abcam | AB84593 | 1:100 |
| HNF4α | Goat | Santa Cruz | SC6556 | 1:100 |
| HSP60 (k-19) | Goat | Santa Cruz | SC-1722 | 1:100 |
| OCT3/4 | Rabbit | Santa Cruz | SC9081 | 1:100 |
| PXR | Rabbit | Santa Cruz | SC25381 | 1:100 |
| Sox17 | Goat | R&D | AF1924 | 1:100 |

Table 9. Primary antibodies source and dilutions

TABLE 10

Secondary antibodies used for immunofluorescence analysis

| Reactive Sp. | Host | Fluorophore | Company | Catalog # | Dilution |
|---|---|---|---|---|---|
| Rabbit | Donkey | AlexaFluor 488 | Jackson | 715-546-150 | 1:100 |
| Goat | Donkey | AlexaFluor 647 | Jackson | 705-606-147 | 1:100 |
| Goat | Donkey | AlexaFluor 488 | Jackson | 705-546-147 | 1:100 |
| Rabbit | Donkey | AlexaFluor 594 | Jackson | 711-585-152 | 1:100 |
| Chicken | Donkey | AlexaFluor 488 | Jackson | 703-545-155 | 1:100 |

Table 10. Secondary antibodies source and dilutions

Nuclear Receptors Cop-GFP Activity Reporter Constructs

PXR Cop-GFP Activity Reporter:

PXR-luciferase reporter construct was a kind gift of Chris Liddle (University of Sydney) (Goodwin B, et al. The Orphan Human Pregnane X Receptor Mediates the Transcriptional Activation of CYP3A4 by Rifampicin through a Distal Enhancer Module. Molecular Pharmacology 1999; 56:1329-1339). The reporter contains a CYP3A4 promoter element and a distal enhancer containing PXR response elements (TGAACTTGCTGACCC; SEQ ID NO: 61), digested out with Acc65 and HindIII. PXRE fragment was blunt end ligated to pGreenFire1 vector (System Biosciences, Mountain View, Calif.) containing copGFP reporter using EcoRI-BamHI digestion.

LXR Cop-GFP Activity Reporter:

LXR Cop-GFP lentiviral reporter vector was purchased from System Biosciences (SBI). The reporter contains four LXR response elements (GGGTTACTGGCGGTCATT-GTA; SEQ ID NO: 62) upstream of a minimal CMV promoter driving Cop-GFP.

PPAR$_\alpha$ Cop-GFP Activity Reporter:

mCMV-GFP lentiviral vector was purchased from System Biosciences (SBI) and digested with EcoRI-BamHI to remove the minimal CMV promoter. The promoter fragment of the human CPT1A 5'-untranslated region (from −562 to +1890) that contains a PPAR response element (TAC- CTTTCCCCTACTTTTC; SEQ ID NO: 63) was amplified from genomic DNA by PCR using forward and reverse oligonucleotides. The forward primer contained EcoRI restriction site and the reverse primer contained a BamHI restriction site. The PCR product was sub-cloned into the digested lentiviral vector.

FXR Cop-GFP Activity Reporter:

mCMV-GFP lentiviral vector was purchased from System Biosciences (SBI) and digested with XbaII-BamHI. The vector was cloned with a PCR amplified BSEP promoter element (GGGACATTGATCCT; SEQ ID NO: 64).

Lentivirus was prepared by transfecting 293T cells with one of the copGFP lentiviral reporter constructs together with pGAG-pol and pVSVG in a ratio of 3:2:1.

A total of 12 µg DNA was diluted in Optimem™ (Invitrogen), vortexed, and supplemented with 25 µL of polyethylenimine, and added drop-wise to the cells. Following 10 minutes incubation at room temperature the mix was added drop-wise to the cells. Two days later, media was collected and filtered through a 0.2 µm syringe filter and concentrated in an Vivaspin 20 filter device (Satorium, Goettingen, Germany) or in an Amicon Ultra-15 filter device (Millipore). The device was spun at 3000×g for 10 to 15 minutes concentrating supernatant 10-fold. For 4 days, during the maturation stage of ESC-derived hepatocyte differentiation, medium was mixed with 1:10 of the concentrated virus and 1:1000 polybrene and added to the differentiating cells. In the last day of differentiation, nuclear receptor activity (PXR) was quantified using Zeiss LSM 700 microscope.

Albumin and AFP Production—

Culture media samples were collected daily and stored at −80° C. Albumin and AFP concentrations were analyzed using Human Albumin ELISA quantitation set (Bethyl laboratories, Montgomery, Tex.) and Human AFP (alpha-fetoprotein) Quantikine ELISA kit (R&D Systems, Minneapolis, Minn.), according to manufacturer directions. ApoB100 concentration was analyzed using ALerCHEK, Inc. (Portland, Me.), total human ApoB-100 ELISA kit as previously described (Goldwasser, 2011). Data was normalized to total cellular protein utilizing the Bradford assay.

Cytochrome P450 Activity and Induction—

CYP1A activity was evaluated utilizing EROD (ethoxyresorufin-o-deethylase) as previously described (Behnia, 2000). To assess CYP3A4 and CYP2C9 activity, the present inventors used a method described by Donato et al. (Donato, 2004). Briefly, cultures were incubated with 100 µM BFC (7-benzyloxy-4-trifluoromethylcoumarinat), or 10 µM MFC (7-methoxy-4-trifluoromethylcoumarin) for 1 hour at 37° C. Supernatant samples were collected every 30 minutes for 2.5 hours. The reactions were stopped by collection of the incubation medium. Metabolite conjugates formed via phase II activity were hydrolyzed by incubation of medium samples with β-glucuronidase/arylsulfatase for 2 hours at 37° C. Samples were diluted 1:1 in quenching solution and HFC (7-hydroxy-4-trifluoromethylcoumarin), the respective fluorescent metabolite formation, was measured at the appropriate wavelengths (410/510) and normalized to total protein determined by Bradford.

To evaluate CYP450 induction, cultures were incubated with 25 µM rifampicin, a PXR agonist, or 50 µM omeprazole, an AhR agonist, dissolved in culture medium for 72 hours. CYP450 activity was quantified as described above at the end of the stimulation period.

Functional Polarization Assay— hESC-derived hepatocytes were incubated for 30 minutes with 5(6)-carboxy-2',7'-dichlorofluorescein diacetate (CD-FDA). Cultures were subsequently washed with ice-cold PBS containing calcium and magnesium and imaging was performed on a Zeiss LSM 700 confocal microscope.

Assessment of Cellular Toxicity—

Cultured cells were exposed to different concentrations of compounds dissolved in culture medium for 24 hours at 37° C. Cell viability was determined utilizing LIVE/DEAD Cytotoxicity kit (Molecular Probes, Eugene, Oreg.) according to manufacturer instructions. In brief, cultures were incubated with 2 µM Calcein AM and 3 µM ethidium homodimer-1 for 25 minutes. Hydrolysis by functional intracellular esterases causes live cells to fluoresce green, while the punctured membranes of dead cells permit ethidium homodimer-1 to bind DNA and fluoresce red. Cellular viability was calculated by live to dead ratio and normalized to negative control. $TC_{50}$ values were quantified using GraphPad Prism software (La Jolla, Calif.).

Toxicological Endpoint Assays (Apoptosis, Cholestasis, Steatosis)—

Toxicological endpoints were evaluated for nine hepatotoxic compounds at $TC_{20}$ values identified above. Quantitation of apoptotic cells was performed utilizing DeadEnd™ fluorometric TUNEL System (Promega, Madison, Wis.) according to manufacturer instructions. In brief, hESC-derived hepatocytes were treated with 1.4 mM acetaminophen, 300 µM diclofenac or 2 µM aflatoxin $B_1$ for 24 hours, and subsequently fixed in 4% paraformaldehyde. Cell were permeabilized and exposed to fluorescein-12-dUTP and terminal deoxynucleotidyl transferase (TdT), dying apoptotic nuclei green. The reaction was subsequently stopped and the cells counterstained for DAPI. A percent apoptotic nucleus was calculated by dividing the number of TUNEL to DAPI positive nuclei.

Quantification of intracellular lipids was performed using LipidTOX™ Green Neutral Lipid Stain (Molecular Probes). Differentiated cells were incubated with 135 µM amiodarone, 2 mM acetylsalicylic acid or 60 µM valproic acid for 24 hours. Cells were treated with 1 µM LipidTOX™ and 1 µg/mL Hoechst 33342 for 20 minutes, and washed with PBS. Staining intensity was normalized to negative control. Hepatic cholestasis was quantified using the CDFDA staining described above. hESC-derived hepatocytes were incubated with 45 µM chlorpromazine, 575 µM cyclosporine A or 80 µM troglitazone for 24 hours. Cells were treated with 2 µg/mL CD-FDA, and 1 µg/mL Hoechst 33342 for 30 minutes. Incubation media was removed and cultures washed with ice-cold PBS containing calcium and magnesium. The number of green CDF particles was normalized to the number of Hoechst nuclei as an indicator of functional bile canaliculi. Particle and nuclei counting was performed utilizing the ImageJ particle analyzer.

Transmission Electron Microscopy (TEM)—

For the TEM analysis, cell were seeded in a plastic 8 chamber slide (Lab-Tek) and fixed in 2.5% Glutaraldeyde, 2% paraformaldehyde in 0.1 M Cacodylate buffer (pH 7.4) for 2 hours at room temp and incubated at 4° C. overnight. Cells were then rinsed 4 times, 10 minutes each, in cacodylate buffer and post fixed and stained with 1% osmium tetroxide, 1.5% potassium ferricyanide in 0.1 M cacodylate buffer for 1 hour. Cells were then washed 4 times in cacodylate buffer followed by dehydration in increasing concentrations of ethanol consisting of 30%, 50%, 70%, 80%, 90%, 95%, for 10 minutes each step followed by 100% anhydrous ethanol 3 times, 20 minutes each. Following dehydration, the cells were infiltrated with increasing concentrations of Agar 100 resin in ethanol, consisting of 25, 50, 75, and 100% resin for 16 hours each step. The cells then were embedded in fresh resin and let polymerize in an oven at 60° C. for 48 hours. Embedded cells in blocks were sectioned with a diamond knife on an LKB 3 microtome and ultrathin sections (80 nm) were collected onto 200 Mesh, thin bar copper grids. The sections on grids were sequentially stained with Uranyl acetate and Lead citrate for 10 minutes each and viewed with Tecnai 12 TEM 100 kV (Phillips, Eindhoven, The Netherlands) equipped with MegaView II CCD camera. Mitochondria diameter and cell/nuclei size were measured manually using Analysis® version 3.0 software (SoftImaging System GmbH, Münstar, Germany).

Oxygen Consumption and Mitochondria Function Evaluation Using Sea Horse—

The extracellular flux analyzer XFp (Seahorse Biosience, North Billerica, Mass.) was used to measure the oxygen consumption rate (OCR) and extracellular acidification rate (ECAR) at the end of the maturation differentiation stage (day 18). Cells were harvest using Trypsin at the last day of differentiation, centrifuge for 5 minutes at 90 g, re-suspended with control medium (no fatty acids) and seeded on a 1% Matrigel coated Seahorse XFp cell culture miniplates (Seahorse Bioscience,) in a density of 10,000 cells per well and cultured for an additional 24 hours. Mitochondrial Stress Test assay was conducted per manufacturer instructions. Briefly, cells were incubated in unbuffered XF Base Medium supplemented with 2 mM Glutamine, 1 mM sodium pyruvate, and 10 mM glucose (pH 7.4) for 1 hour at 37° C. in a non-$CO_2$ incubator. Oxygen consumption was measured by the XFp Extracellular Flux Analyzer (Seahorse Biosciences). Mitochondrial function was profiled by successive injections of 1 µM oligomycin, 0.5 µM Carbonyl cyanide-4 (trifluoromethoxy) phenylhydrazone (FCCP), and a mixture of 0.5 µM antimycin A and 0.5 µM rotenone. Data are presented normalized to $10^3$ cells as determined by Hoechst DNA content assay.

Example 1

Derivation of Hepatocytes from Pluripotent Stem Cells
Experimental Results
Rapid Derivation of Human Embryonic Stem Cell (hESC) Derived Hepatocytes—

The present inventors developed a four-step hepatic differentiation protocol that included postpartum development (FIG. 1A). SRY (sex determining region Y)-box 17 (SOX17)-positive definitive endoderm emerged on the first 3 days of culture (FIGS. 1B-E), with pluripotent markers octamer-binding transcription factor 4 (OCT4) and SOX2 disappearing by day 7 on both gene and protein levels. Transient expression of GATA-binding protein 4 (GATA4) and forkhead box protein A2 (FOXA2) marked the emergence of hepatoblasts on gene and protein levels (FIGS. 1B-E). Fluorescence-activated cell sorting analysis revealed a relatively homogenous population, with 83% of cells positive for both HNF-4α and FOXA2 (FIG. 1G). Stimulation with OSM and basic fibroblast growth factor (FGF2) directed hepatoblasts to the parenchymal fate. The fetal-like hepatocyte population showed a significant expression of AFP and alpha 1 antitrypsin (A1AT), with minor expression of albumin (FIGS. 1B-E). Finally, this protocol mimicked the postpartum environment by removing OSM [Kamiya A, et al. FEBS Lett 2001; 492:90-94] and exposing cells to 16.7 µM of oleic and linoleic acid (fatty acids) (FIG. 1A), promoting a dramatic increase in albumin expression, with an associated decrease of AFP expression (FIG. 1E). Ninety-six percent of differentiated cells were positive for albumin, and 83% were positive for both albumin and HNF-4α expression (FIG. 1H). The protocol was robust, producing similar results by qRT-PCR in HuES8 and H9 hESCs as well as hiPSC lines 12F2 and U21 on day 16 of differentiation (FIGS. 6A-J).

hESC-Derived Hepatocytes Show Low PXR-Dependent CYP450 Expression—

The present inventors compared the expression patterns of hESC-derived hepatocytes to primary human hepatocytes (PHH) and HepG2 cells cultured under the same conditions (FIGS. 2A-B). Gene expression of blood proteins albumin and A1AT, was not significantly different from primary cells (FIG. 2B). Similarly the expression of hepatic nuclear receptors HNF4α, farnesoid X receptor (FXR), and constitutive androstane receptor (CAR) was equivalent to primary cells, with fatty acid-activated peroxisome proliferator-activated receptor alpha (PPARα) showing an expected 2-fold increase over primary cells (FIGS. 2A-B). However, expression of PXR was 4% of PHH expression levels, and its targets, CYP2C9 and CYP3A4, were 4- and 8-fold lower than controls (FIGS. 2A-B). Notably, AhR target CYP1A2 and PPAR target CYP2D6 showed higher levels of expression (FIGS. 2A-B). These results suggest that lack of proper PXR activation is responsible for the minimal expression of CYP2C9 and CYP3A4 in the hESC-derived hepatocytes.

Example 2

LCA and MK4 Drive PXR-Dependent Hepatic Maturation
Experimental Results
LCA and MK4 Drive PXR-Dependent Hepatic Maturation—

LCA and MK4 are secondary metabolites previously shown to activate PXR [Staudinger J L, et al. Proc. Natl. Acad. Sci. U.S.A. 2001; 98:3369-3374; Tabb M M, et al. J Biol Chem 2003; 278:43919-43927; Ichikawa T, et al. J Biol Chem 2006; 281:16927-16934]. When added to the last stage of differentiation, LCA caused a dose-dependent induction of PXR, CAR, CYP2C9, and CYP3A4 expression (P<0.05; n=3; FIG. 2D). At 50 µM, LCA induced PXR, CAR, CYP2C9, and CYP3A4 by 10-, 16-, 5-, and 73-fold, respectively. At this concentration, CYP3A4 expression was 9-fold higher than primary hepatocytes and LCA showed mild toxicity. Therefore, subsequent differentiation was carried out at 10 µM of LCA. In contrast, addition of MK4 to the last stage of differentiation showed no significant effect (FIG. 2E). However, addition of 10 µM of both LCA and MK4 had a synergistic effect, up-regulating expression of CAR and PXR by 3- and 3.6-fold (P<0.05), while increasing expression of CYP3A4 and CYP2C9 by 3- to 4-fold (P<0.01), respectively (FIG. 2F).

To validate activation of PXR, the present inventors infected hESCs with a lentivirus reporter containing multiple repeats of the PXR response element upstream of a destabilized CopGFP (ppluGFP2). CopGFP expression was observable in fetal-like hepatocytes on day 12 of differentiation, but showed an additional 3-fold increase in activity by day 16 (P<0.004; FIG. 2G). Addition of LCA and MK4 showed an additional 1.5-fold increase in basal PXR activity (P<0.0001). Immunofluorescence staining showed that 70±12% of hESC-derived hepatocytes treated with LCA and MK4 exhibited nuclear localization of PXR, compared with 20±8% for untreated cells (P<0.01; FIG. 2H). Finally, addition of silibinin, a recently identified PXR inhibitor [Mooiman K D, et al. Drug Metab Dispos 2013; 41:1494-1504] to hESC-derived hepatocytes during treatment with LCA and MK4 reversed their effect, leading to a dose-dependent inhibition of PXR, CYP3A4, and CYP2C9 (P<0.01; FIG. 2I).

Taken together, these results demonstrate that LCA and MK4 up-regulate the nuclear receptor, PXR, and its target, CYP450, genes in hESC-derived hepatocytes. In addition, the present inventors further validated the synergistic activity of LCA and MK4 in fetal human hepatocytes [Avior Y et al. Hepatology 2015].

Example 3

Protein Expression and Functional Polarization
Experimental Results
Protein Expression and Functional Polarization—

Epithelial polarization is a critical function of hepatocytes, which secrete bile acids and modified drug metabolites by apical bile canaliculi [Kidambi S, et al. Proc Natl Acad Sci USA 2009; 106:15714-15719; Khetani S R et al. Nat Biotechnol 2008; 26:120-126]. By day 16 of differentiation, in the presence of LCA and MK4, cells acquired homogenous cuboidal morphology and displayed granular perinuclear staining for albumin and CYP3A4, as well as a strong nuclear staining for HNF-4α (FIG. 3A). A small fraction of cells became binucleated (arrows). To evaluate bile canaliculi function, cells were treated with CDFDA, which was metabolized to fluorescent CDF and secreted to bile canaliculi by active multidrug resistance-associated protein 2 (MRP2). Approximately 85% of cells showed functional bile canaliculi (arrows), with isolated clusters showing cytoplasmic CDF staining (FIG. 3B, right).

Finally, secretion of albumin, AFP, and ApoB100 was tracked throughout differentiation. Albumin and ApoB100 production escalated from day 12 onward, reaching 13.2 μg/mL of albumin (P=0.359; n=3) and 1.0 μg/mL of ApoB100 (P=0.774; n=3), not significantly different from isolated primary hepatocytes (FIG. 3C, dashed line). In contrast, AFP production declined by 22% from day 14 onward (P<0.02; n=3; FIG. 3C).

RNA-Sequencing Analysis Shows that LCA and MK4 Drive Hepatic Maturation—

To explore the extent of characteristic fetal and mature expression, the present inventors carried out RNA sequencing (RNA-Seq) analysis on LCA- and MK4-treated hESC-derived hepatocytes (LCA/MK4), comparing them to untreated controls (control). RNA was similarly isolated from adult PHHs and fetal human hepatocytes (FHHs). Unsupervised Spearman's correlation of 2,925 genes (FIG. 3D) showed that LCA- and MK4-treated cells cluster closer to adult than to fetal hepatocytes. Expression of mature factors asialoglyco protein receptor 1 (ASGR1), CYP3A4, and glutamic-pyruvate transaminase/alanine aminotransferase (GPT1/ALT) were higher in treated than untreated cells (FIG. 3E), whereas fetal makers CYP3A7 and replication factor C3 (RFC3) were lower (FIG. 3F).

Example 4

Cyp450 Activity and Induction in hESC-Derived Hepatocytes
Experimental Results
CYP450 Activity and Induction in hESC-Derived Hepatocytes—

To evaluate CYP450 activity in hESC-derived hepatocytes differentiated in the presence of LCA and MK4, the present inventors monitored the metabolism of EROD, a CYP1A substrate [Behnia K, et al. Tissue Eng 2000; 6:467-479] and that of BFC and MFC, nonspecific substrates metabolized by CYP3A4, 2E1, and 2C9 [Donato M T, et al. Drug Metab Dispos 2004; 32:699-706]. As expected, fetal CYP1A activity was 2-fold higher in hESC-derived hepatocytes than primary cells (FIG. 4A). However, treatment with LCA and MK4 caused a 3- and 2-fold increase in BFC and MFC metabolism, compared to untreated cells, respectively (P<0.05).

Importantly, CYP450 activity in LCA- and MK4-treated hESC-derived hepatocytes was inducible by classical agonists. Omeprazole, an agonist of AhR, which regulates CYP1A, induced EROD and BFC metabolism by 9- and 3-fold, respectively (FIG. 4B). Rifampicin, an agonist of PXR, which regulates CYP3A4 and 2C9, induced BFC and MFC metabolism by 2- and 10-fold, respectively (FIG. 4B). Finally, the present inventors exposed cells to 2% DMSO, a nonspecific treatment that induces CYP450 expression in primary cells. Expression of PXR and most CYP450 enzymes which were checked increased from 2- to 6-fold (FIG. 4C). Together, the data show that LCA and MK4 induced functional CYP450 regulation at a substantial fraction of primary hepatocyte potential.

Example 5

Uses of hESC-Derived Hepatocytes for Prediction of Acute Toxicity

Experimental Results
hESC-Derived Hepatocytes Demonstrate Accurate Prediction of Acute Toxicity—

Application of hESC-derived hepatocytes for predictive toxicology was suggested by several groups, but thus far demonstrated poor correlation to primary cells [Szkolnicka D, et al. Stem Cells Transl Medicine 2014; 3:141-148]. To test the ability of LCA- and MK4-treated hESC-derived hepatocytes to predict hepatotoxic effects, the present inventors tested nine compounds that display different toxicological endpoints (e.g., cholestasis) and three control compounds generally regarded as safe. Differentiation was adapted to 96-well plates (General Materials and Experimental Methods above). Cells were exposed to increasing concentrations of compounds on day 16, and viability was quantified using fluorescence Live/Dead staining after 24 hours of exposure (FIG. 4D). Results are summarized as $TC_{50}$, the concentration causing 50% cell death (FIG. 4D). Dose-dependence curves showed a classical sigmoidal response characteristic of toxic metabolite formation. Importantly, a normalized $TC_{50}$ toxicity profile generated for LCA- and MK4-treated hESC-derived hepatocytes was not significantly different from primary cells (P=0.13; n=3), whereas HepG2 profile was significantly different (P=0.04; n=3; FIG. 4E).

Remarkably, $TC_{50}$ values of LCA- and MK4-treated hESC-derived hepatocytes showed a striking correlation to primary cells, with an $R^2=0.94$ to the 45-degree angle (dotted line), compared to $R^2=0.65$ for HepG2 cells and an $R^2=0.19$ for untreated cells (FIG. 4F).

Surprisingly, whereas menthol and mannitol controls showed no adverse effects, the hormone, melatonin, demonstrated a clear toxicity at a $TC_{50}$ value of 0.7±0.2 mM. This concentration is 2 orders of magnitude higher than the standard 5- to 10-mg dose marking melatonin as safe (FIG. 4D). Based on these data, the accuracy of these predictions ranges from 92% to 100%.

Accurate Prediction of Toxicological Endpoints—

To demonstrate the ability of hESC-derived hepatocytes to predict the precise toxicological response, the present inventors evaluated toxicological endpoints of the nine hepatotoxic compounds defined above at $TC_{20}$ concentrations to minimize the effect of cell death (FIGS. 5A-I).

Steatosis was evaluated using LipidTox neutral lipid stain. After 48 hours of exposure, cultures treated with amiodarone, acetylsalicylic acid (aspirin), or valproic acid showed a 25- to 26-fold increase in intracellular lipids, compared to control (P<0.001; n=4; FIGS. 5A-B).

Cholestasis was evaluated by CDFDA staining. After 24 hours of exposure, cultures treated with troglitazone, chlorpromazine (thorazine), or cyclosporine A showed a 13- to 30-fold decrease in number of CDF-positive bile canaliculi, compared to control (P<0.003; n=4; FIGS. 5C-D).

Finally, apoptosis was evaluated using the TUNEL assay. After 24 hours of exposure, cultures treated with diclofenac, acetaminophen (Tylenol), or aflatoxin B1 showed a 3- to 4-fold increase in percent of apoptotic nuclei, compared to control (P<0.02; n=4; FIGS. 5E-F).

Taken together, the data demonstrate that hESC-derived hepatocytes can be utilized to predict appropriate toxicological end-points with high sensitivity.

Finally, the present inventors sought to identify the toxicological mechanism underlying the observed toxicity of melatonin. Melatonin did not affect the number of functional bile canaliculi at $TC_{20}$ concentration (P<0.4; n=4; FIGS. 5G-I). In contrast, melatonin caused a significant 30-fold increase in lipid accumulation (P<0.006; n=4), suggesting that the hormone might cause steatosis at high concentration or prolonged use.

Example 6

Generalized Protocol for Hepatocyte Derivation from Varying Human Pluripotent Stem Cell Lines Experimental Results Sub-Culture and General Derivation of Human Pluripotent Stem Cell (hPSC) Derived Hepatocytes—

Human embryonic stem cells (hESC) and human induced pluripotent stem cells (hiPSC) from several sources were expanded in a feeder-independent culture. When cells reached 50% confluence, the present inventors induced hepatic differentiation using the protocol described in Avior, 2015, yet with significant improvements. Fast growing cell lines reached confluence and stopped differentiating at a fetal stage due to contact inhibition. Therefore, present inventors added a sub-culture step on day 8 of endoderm induction, that permits better control of cell density, by defining 30% confluence post-seeding. The protocol was extended to 18 days, by starting stage 3 on day 10 as shown in FIG. 11B.

Example 7

Fatty Acids Oleic Acid and Linoleic Acid Increase Human Embryonic Stem Cell Derived Hepatocyte Maturation Experimental Results OA and LA Drive Nuclear Receptors Activation—

Nuclear receptors are ligand-activated transcription factors that play a critical role in the regulation of metabolic processes and mature liver function (Clavia Ruth Wooton-Kee, 2010; Panadero, 2000; Lacroix, 1997). Fatty acids were previously found to activate certain nuclear receptors in the adult liver, suggesting they might play a similar role in their fetal induction during the transition from glucose-rich placental to lipid-rich enteral nutrition (Finley et al, 1985, summarized in Table 11, hereinbelow); Fernando-Warnakulasuriya, 1981).

TABLE 11

Fatty acid composition of human breast milk

| | Percentage in fat fraction (%) | Common name |
|---|---|---|
| C12:0 | 6 | Lauric |
| C14:0 | 8 | |
| C16:0 | 23 | Palmitic |
| C18:0 | 8 | Stearic |
| C18:1 ω9 | 32 | Oleic |
| C18:2 ω6 | 17 | Linoleic |
| C18:3 ω3 | 1.6 | α-linoleic |
| C20:4 ω6 | 0.1 | Arachidonic (AA) |
| C22:6 ω3 | 0.3 | Docosahexaenoic (DHA) |

Table 11. Fatty acid composition of human breast milk (Values are obtained from Finley et al., 1985, which is fully incorporated herein by reference).

Oleic acid (OA) and linoleic acid (LA) were added to the last stage of differentiation [days 13-16 (when differentiation did not include a step of sub-culturing) or days 15-18 (when the differentiation included a step of sub-culture)]. Exposure to OA and LA induced a dose-dependent activation of PPARα response element (PPRE), LXRα response element (LXRE) and PXR response element (PXRE), but not of FXR response element (FXRE) (p<0.01) (FIG. 6A). NR activation was validated by infecting hESC with a set of lentivirus activity reporters as described in the "GENERAL MATERIALS AND EXPERIMENTAL METHODS" herein above at the last four days of differentiation (FIG. 6A). Gene expression analysis showed similar induction of the nuclear receptor and a classical target gene reaching a maximum induction between 62 to 125 µM (FIG. 6B).

OA and LA Drive Hepatocyte Maturation—

Albumin and AFP are positive and negative markers of hepatocyte maturity, respectively. Differentiation in the presence of OA and LA produced a dose-dependent correlation with albumin increasing by 45% and AFP decreasing by 30% at 125 µM (FIGS. 6C-D). Concentrations of 250 µM and above caused a toxic effect leading to decrease differentiation (FIGS. 6B-E). Finally, a 24-hours treatment with GW9662, a PPARα/γ antagonist, inhibited the expression of genes involved in lipid metabolism and caused a significant decrease in albumin gene expression and production (n=5, p<0.05), reducing them back to control levels (FIGS. 6F-G). Taken together, these results demonstrate that OA and LA promote the metabolic maturity of hESC-derived hepatocytes via nuclear receptors activation with PPAR having a key regulatory role in the hepatic metabolic profile and albumin expression.

OA and LA Promote PPAR Dependent PXR Activation—

Each NR regulates the expression and activity of other transcription factors, forming a network of interactions regulating metabolic and developmental processes. The activation of lipid metabolism regulator, PPAR, by OA and LA at the last stage of differentiation also induced the expression, activity and nuclear localization of PXR in hESC-derived hepatocytes (FIGS. 6A, 6B and 6H-I). Surprisingly, when replacing LA with its microbial derived isomer, 9CLA, an additional 40% increase in PXR nuclear localization (p<0.0001) was detected (FIGS. 6H-I). Increased activity of PXR was supported by the increase in CYP3A4 and CYP2C9 gene expression and activity (FIGS. 6H and 6I). PXR nuclear localization and activation was down-regulated by the PPAR antagonist, GW9662, supported by fluorescent microscopy and gene expression (FIGS. 6H-I).

Example 8

Effect of the Fatty Acids on Mitochondria Development in Esc-Derived Hepatic Cell Experimental Results OA and LA Promote Hepatic Mitochondria Development Via PPAR Activation—

Primary hepatocytes maintain a network of over 1400 mitochondria, whose maturation and activity is essential for hepatic function (Yue Yu, 2012; Valcarce C, 1988; EG white., 1939). Transmission electron microscopy (TEM) showed clear ultra-structural changes induced by differentiation of hESC-derived hepatocyte with OA and LA, or OA and 9CLA compared to control (FIG. 7A). Treatment with fatty acids caused the accumulation of lipid droplets (FIG. 7A) and increase cell size by 80% for OA and LA treatment compared to control ($p<0.01$; FIG. 7C). Mitochondria decreased in diameter by 20-30%, acquiring elongated morphology indicative of network formation (FIG. 7B).

Confocal imaging of mitochondrial protein HSP60 showed similar results (FIG. 7D) with a highly branched network of mitochondria appearing primarily during OA and 9CLA treatment. Indeed, image analysis showed a 20% decrease in mitochondria minor axis (i.e. diameter), a 12% increase in mitochondria major axis (i.e. length), and a 7% increase in eccentricity (FIGS. 7D-H).

PPARα is known to regulate the expression of PGC1α and MFN2, essential for proper mitochondria biogenesis and fusion (Chen, 2003; Chen, 2005). To evaluate the molecular mechanism underlying the morphological changes, expression of key biogenesis, fusion and fission regulators was evaluated. Fatty acid treatment increase MFN2 expression by 70% with FIS1 increasing only by 20%, validating the increase in fusion to fission ratio (FIG. 7J). Elongation and narrowing of mitochondria was reversed by GW9662, supported by the decrease in PGC1, MFN2 and FIS1 gene expression and indicates on a PPARα-dependent mechanism involved in regulating mitochondria morphology (FIGS. 7E-G and FIG. 7J).

OA and LA Increase Mitochondrial Function—

Hepatocyte mitochondrial activity defines the metabolic ability of the cells. To evaluate mitochondrial function the present inventors used the XFp extracellular flux analyzer (Seahorse Biosience, North Billerica, Mass.). The machine measures oxygen consumption rate (OCR) during the sequential addition of toxins and inhibitors to specifically quantify basal respiration, oxidative phosphorylation and mitochondrial mass. The present inventors show that oxidative phosphorylation (ATP production) increase by 2-folds following OA and LA addition, and by 2.7-fold increase in response to OA and 9CLA ($p<0.05$) (FIGS. 8A-B). Interestingly, induction of mitochondrial function by OA and 9CLA resulted in about half of the efficacy compared to human hepatocytes (FIGS. 8A-B).

Analysis and Discussion

Scarcity of human hepatocytes and batch-to-batch variability has increased interest in hESC and hiPSC-derived hepatocytes for both clinical and toxicological applications. In this work the present inventors present a rapid 16 to 18-day protocol for differentiation of hESC-derived hepatocytes. Like other groups, previous protocols produced a relatively homogenous induction of albumin and HNF4α (FIGS. 1A-H), but with high AFP expression levels, low CYP450 activity (Si-Tayeb 2010; Chen 2012; Roelandt 2013) and under-developed mitochondria (Yu, 2012; wanet, 2014; Avior, 2015). The limited hepatic function could be a result of failing to include postnatal developmental in current differentiation protocols. Recently the present inventors presented the hepatic-maturing influence of bacteria derived, lithocoloc acid (LCA) and vitamin $K_2$ (MK4), via PXR activation, suggesting a crucial role of postnatal cues in hepatic development (Avior et al. 2015).

Here the present inventors demonstrate the inductive role of postnatal nutritional cues, oleic acid (OA) and linoleic acid (LA) and that of the naturally occurring gut microbiota derived LA isomer, 9CLA, in promoting hepatic maturation and mitochondrial development via PPAR activation.

Hepatocytes play a central role in lipid, cholesterol and xenobiotics metabolism, as such they are highly metabolic. Relying on external cues to promote their functions, nuclear receptors act as sensors for many metabolites and nutrients consumed in the diet, and act as metabolic regulators in the liver. Post-partum, a variety of functional adaptations are essential for maintaining metabolic homeostasis. The arrest of placental circulation, consequently results in changes in hepatic NR activity and expression (RI, 2000; Roux C, 2000; Panadero, 2000; Lacroix, 1997). The present inventors found that addition of OA and LA during the last stage of hESC differentiation promoted the metabolic maturity of the cells by inducing the activation of key metabolic NRs-PPARα, LXRα and PXR (FIGS. 6A-I). Replacing LA with microbial derived 9CLA promoted an additional maturation by inducing a PPAR dependent-PXR activation (FIGS. 6H-J).

Mitochondrial development is closely linked to pluripotency, differentiation and proliferation (Wanet 2014). Pluripotent blastomeres, before implantation, and ESC possess small and underdeveloped mitochondria, which rely on anaerobic respiration. Upon cellular differentiation and commitment, functional and morphological changes that define the mature mitochondria occur. Mitochondria acquire an elongated morphology with swollen cristae and dense matrices, and cells gain a more efficient aerobic metabolism that result in an increase in ATP production and oxygen consumption (Valcarce C, 1988; Cuezva J M, 1990; JK, 1975; Jakovcic S, 1971; J. M. Facucho-Oliveira and J. C. St. John, 2009). Hepatocytes, having high metabolic activity, require high content of mitochondria to satisfy cellular energetic demand. Therefore, development and maturation of mitochondria must go hand in hand with hepatic maturation. Although the role of mitochondria in energy production and hepatic metabolic functionality is well documented, only few studies evaluated mitochondrial development in differentiated hepatocytes. Wanet and colleagues (Wanet, 2014) provide detailed characterization and kinetics of mitochondrial respiration, biogenesis and morphological changes during differentiation, elucidating the role of mitochondrial biogenesis and function in the regulation of hepatic differentiation (Wanet, 2014). In the work of Yu, the morphological and functional changes of differentiated hiPSC were compared to primary hepatocytes, highlighting the insufficient maturity of the cells. The present inventors attribute this significant difference in mitochondrial function to post-partum development.

Fatty acids are poorly transferred through the placenta and gut microbial population is considered to emerge only at birth. Research focusing on the microbiota has defined the metabolic and physiological roles bacteria play within the mutualistic relationship (Gakuhei, 2010; Redondo-lopez, 1990) and the role of nutritional composition on the developing microbiota (Redondo-lopez, 1990). The present inventors have uncovered that 9CLA, produced by neonatal bacteria populations, has a role in promoting hepatic maturation and mitochondria development via PPAR activation in hESC-derived hepatocytes (FIGS. 6A-J-8A-B). The increase in maturation markers and mitochondria function demonstrate, and further support, that there is a tight link between nutrition, gut bacteria populations and hepatic cellular development.

Mitochondrial development and metabolic maturation of differentiated pluripotent cells are a general concern not only in hepatic differentiation but also in differentiation of other cell types. Myocytes and pancreatic beta-cells, for example, are highly dependent on mitochondria function for their proper functionality and in order to meet their energy demands (Asa, 2007; Maechler, 2010). The inducible effect of OA, LA and especially that of microbial derived, 9CLA, on NR activation and mitochondrial development should be tested in other differentiation protocols and could assist in promoting maturation and full functionality.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference to the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

1. AM Z. StemBook, 2008.
2. V B S. Hepatic function and physiology in the newborn. Seminars in Neonatology 2003; 8:337-346.
3. Morelli L. Postnatal Development of Intestinal Microflora as Influenced by Infant Nutrition. J. Nutr. September 2008; 138:1791S-1795S.
4. DA. SDaM. The marriage of nutrigenomics with the microbiome: the case of infant-associated bifidobacteria and milk. American Society for Nutrition 2014; 99:6795-7035.
5. PL C. Development of intestinal microbiota. Gastrointestinal Microbiology 1997; 2:3-38.
6. Knol MHaJ. Quantitative Real-Time PCR Assays To Identify and Quantify Fecal *Bifidobacterium* Species in Infants Receiving a Prebiotic Infant Formula. APPLIED ANDENVIRONMENTALMICROBIOLOGY 2005: 2318-2324.
7. Finley D A L B, Dewey K G, Grivetti L E. Breast milk composition: fat content and fatty acid composition in vegetarians and non-vegetarians. Am J ClinNutr. 1985; 41:787-800.
8. G. V. Halade M M R, and G. Fernandes, ". "Effect of CLA isomers and their mixture on aging C57Bl/6J mice," European Journal of Nutrition 2009; 48:409-418.
9. G. V. Halade MMR, and G. Fernandes, ". Differential effects of conjugated linoleic acid isomers in insulin-resistant female C57Bl/6J mice," Journal of Nutritional Biochemistry, 2010; 21:332-337.
10. H. Poirier J S S, R. J. Kim, and M. A. Lazar, "Nutritional supplementation with trans-10, cis-12-conjugated linoleic acid induces inflammation of white adipose tissue," Diabetes 2006; 55:1634-1641.
11. C. M. Reynolds and H. M. Roche. Conjugated linoleic acid and inflammatory cell signalling," Prostaglandins Leukotrienes and Essential Fatty Acids 2010; 82:199-204.
12. J. S. Choi I U K, M. H. Jung, and J. Song, ". Effects of three different conjugated linoleic acid preparations on insulin signalling, fat oxidation and mitochondrial function in rats fed a high-fat diet,". British Journal of Nutrition, 2007; 98:264-275.
13. Finlay B S, I. Russell, S. Gut Microbiota in Health and Disease. Physiol Rev 2010; 90:859-904.
14. Moya-Camarena S Y VdHJ, Belury M A. Conjugated linoleic acid activates peroxisome proliferator-activated receptor alpha and beta subtypes but does not induce hepatic peroxisome proliferation in Sprague-Dawley rats. BiochimBiophys Acta 1999; 1436:331-342.
15. Beck Fea. The ontogeny of peroxisome-proliferator-activated receptor gene expression in the mouse and rat. Proceedings. Biological sciences/The Royal Society 1992; 247:83-87.
16. Panadero M, Herrera, E. & Bocos, C. Peroxisome proliferator-activated receptor-alpha expression in rat liver during postnatal development. Biochimie 2000; 82:723-726.
17. FA H. Energetic aspects of late fetal and neonatal metabolism Academic Press, 1975.
18. HommesFA KGaBA. The regulation of ATP synthesis in fetal rat liver. Enzyme 1973:351.
19. R. PLaS. The transport and accumulation of adenine nucleotides during mitochondrial biogenesis. Biochem J. 192:75-83 (1980). 1980; 192:75-83.
20. Yue Yu H L, Yasuhiro Ikeda, Bruce P. Amiot, Piero Rinaldo, Stephen A. Duncan, Scott L. Nyberg. Hepatocyte-like cells differentiated from human induced pluripotent stem cells: Relevance to cellular therapies Stem Cell Research 2012; 9:196-207.
21. Anaïs Waneta NmR, Mehdi Najarb, Etienne Sokalc, Thierry Arnoulda, Mustapha Najimic, Patricia Renarda, Mitochondrial remodeling in hepatic differentiation and dedifferentiation. The International Journal of Biochemistry & Cell Biology 2014; 54:174-185.
22. Avior Y L G, Zimmerman M, Kitsberg D, Schwartz R, Sadeh R, Moussaieff A, Cohen M, Itskovitz-Eldor J, Nahmias Y. Microbial-Derived Lithocholic Acid and Vitamin K2 Drive the Metabolic Maturation of Pluripotent Stem Cells-Derived and Fetal Hepatocytes. hepatology 2015; 62:265-278.
23. G J Fernando-Warnakulasuriya J E S, S C Frost and M A Wells. Studies on fat digestion, absorption, and transport in the suckling rat. I. Fatty acid composition and concentrations of major lipid components. The Journal of Lipid Research 1981; 22:668-374.
24. Clavia Ruth Wooton-Kee D J C, Antony T Athippozhy, Tianyong Zhao, Brett R Jones, and Mary Vore. Mechanisms for increased expression of cholesterol 7α-hydroxylase (Cyp7a1) in lactating rats Hepatology 2010; 51:277-285.

25. Lacroix D, Sonnier, M., Moncion, A., Cheron, G. & Cresteil, T. Expression of CYP3A in the human liver—evidence that the shift between CYP3A7 and CYP3A4 occurs immediately after birth. European journal of biochemistry/FEBS 1997; 247:625-634.
26. Esmaeli S A A, Soleimani M, Rahbarizadeh F, Frouzandeh-Moghadam M. The role of albumin and PPAR-α in differentiation-dependent change of fatty acid profile during differentiation of mesenchymal stem cells to hepatocyte-like cells. Cell Biochem Funct 2014; 32:410.
27. Mochizuki K M H, Kawai H, et al. Possible role of fatty acids in milk as the regulator of the expression of cytosolic binding proteins for fatty acids and vitamin A through PPARα in developing rats. J Nutr Sci Vitaminol 2007; 53:515-521.
28. Avior Y, Bomze, D., Ramon, O. & Nahmias, Y. Flavonoids as dietary regulators of nuclear receptor activity. Food & function 2013; 4:831-844.
29. Valcarce C N R, Encabo P, Loeches E, Satrustegui J and Cuezva J M. Postnatal Development of Rat LiverMitochondrial Functions. The Journal of Biological Chemistry 1988; 263:7767-7775.
30. EG. W. Some observations on the liver of the pig: the hepatic lobule and liver cell during post-natal growth. J Anat. 1939; 73:365-386.
31. Chen H C A, Chan D C. Disruption of fusion results in mitochondrial heterogeneity and dysfunction. J Biol Chem. 2005; 280:26185-26192.
32. Hsiuchen Chen S A D, Andrew J. Ewald, Erik E. Griffin, Scott E. Fraser, and David C. Chan. Mitofusins Mfn1 and Mfn2 coordinately regulate mitochondrial fusion and are essential for embryonic development. J Cell Biol. 2003; 160:189-200.
33. Si-Tayeb K, Lemaigre, F. P. & Duncan, S. A. Organogenesis and Development of the Liver. Developmental Cell 2010; 18 175-189
34. Chen Y-Fea. Rapid generation of mature hepatocyte-like cells from human induced pluripotent stem cells by an efficient three-step protocol. Hepatology 2012; 55:1193-1203.
35. Roelandt P, Vanhove, J. & Verfaillie, C. Directed differentiation of pluripotent stem cells to functional hepatocytes. Methods Mol Biol 2013; 997:141-147.
36. RI. K. Inborn errors of cholesterol biosynthesis. Adv Pediatr 2000; 47:1-52.
37. Roux C W C, Mulliez N, Gaoua W, Cormier V, Chevy F, D. aC. Role of cholesterol in embryonic development. Am J Clin Nutr 2000; 71 suppl:1270S-1279S.
38. Cuezva J M V C, Luis A M, Izquierdo J M, Alconada A and Chamorro M. Postnatal Mitochondrial Differentiation in the Newborn Rat. Endocrine and Biochemical Development of the Fetus and Neonate. Reproductive Biology 1990:113-135.
39. JK P. The maturation of the inner membrane of foetal rat liver mitochondria. An example of a positive feedback mechanism. BIOCHEMICAL JOURNAL 1975; 150:477-488.
40. Jakovcic S H J, Getz G S, Rabinowitz M and Swift H. Mitochondrial Development in Liver of Foetal and Newborn Rats. Biochem J 1971; 121:341-347.
41. Facucho-Oliveira J M S J J. The relationship between pluripotency and mitochondrial DNA proliferation during early embryo development and embryonic stem cell differentiation. Stem Cell Rev. 2009; 5:140-158.
42. Gakuhei Son M K, and Ian N. Hines. Contribution of Gut Bacteria to Liver Pathbiology. Gastroenterology Research and Practice 2010.
43. Redondo-Lopez V C R, Sobel J D. Emerging role of lacto-bacilli in the control and maintenance of the vaginal bacterial microflora. Rev Infect Dis 1990; 12:856-872.
44. Asa B. Gustafsson R A G. Heart mitochondria: gates of life and death Cardiovascular Research 2007.
45. Maechler P L N, Casimir M, Vetterli L, Frigerio F, Brun T. Role of mitochondria in beta-cell function and dysfunction. Adv Exp Med Biol. 2010; 654:193-216.
46. Guengerich F P. Cytochrome P450 and Chemical Toxicology. Chemical Research in Toxicology 2007; 21:70-83.
47. Kaplowitz N. Idiosyncratic drug hepatotoxicity. Nat Rev Drug Discov 2005; 4:489-499.
48. Gottmann E, Kramer S, Pfahringer B, Helma C. Data quality in predictive toxicology: reproducibility of rodent carcinogenicity experiments. Environ Health Perspect 2001; 109:509-514.
49. Olson H, Betton G, Robinson D, Thomas K, Monro A, Kolaja G, Lilly P, et al. Concordance of the toxicity of pharmaceuticals in humans and in animals. Regul Toxicol Pharmacol 2000; 32:56-67.
50. LeCluyse E L. Human hepatocyte culture systems for the in vitro evaluation of cytochrome P450 expression and regulation. Eur J Pharm Sci 2001; 13:343-368.
51. Guillouzo A. Liver cell models in vitro toxicology. Environ Health Perspect 1998; 106 Suppl 2:511-532.
52. Hewitt N J, Lechon M J, Houston J B, Hallifax D, Brown H S, Maurel P, Kenna J G, et al. Primary hepatocytes: current understanding of the regulation of metabolic enzymes and transporter proteins, and pharmaceutical practice for the use of hepatocytes in metabolism, enzyme induction, transporter, clearance, and hepatotoxicity studies. Drug Metab Rev 2007; 39:159-234.
53. Nahmias Y, Berthiaume F, Yarmush M L. Integration of technologies for hepatic tissue engineering. Adv Biochem Eng Biotechnol 2007; 103:309-329.
54. Kidambi S, Yarmush R S, Novik E, Chao P, Yarmush M L, Nahmias Y. Oxygen-mediated enhancement of primary hepatocyte metabolism, functional polarization, gene expression, and drug clearance. Proc Natl Acad Sci USA 2009; 106:15714-15719.
55. Khetani S R, Bhatia S N. Microscale culture of human liver cells for drug development. Nat Biotechnol 2008; 26:120-126.
56. Shulman M, Nahmias Y. Long-term culture and coculture of primary rat and human hepatocytes. Methods Mol Biol 2013; 945:287-302.
57. Schwartz R E, Reyes M, Koodie L, Jiang Y, Blackstad M, Lund T, Lenvik T, et al. Multipotent adult progenitor cells from bone marrow differentiate into functional hepatocyte-like cells. J Clin Invest 2002; 109:1291-1302.
58. Stock P, Bruckner S, Ebensing S, Hempel M, Dollinger M M, Christ B. The generation of hepatocytes from mesenchymal stem cells and engraftment into murine liver. Nat Protoc 2010; 5:617-627.
59. Lue J, Lin G, Ning H, Xiong A, Lin C S, Glenn J S. Transdifferentiation of adipose-derived stem cells into hepatocytes: a new approach. Liver Int 2010; 30:913-922.
60. Zhu S, Rezvani M, Harbell J, Mattis A N, Wolfe A R, Benet L Z, Willenbring H, et al. Mouse liver repopulation with hepatocytes generated from human fibroblasts. Nature 2014.
61. Duan Y, Ma X, Zou W, Wang C, Bahbahan I S, Ahuja T P, Tolstikov V, et al. Differentiation and characterization of metabolically functioning hepatocytes from human embryonic stem cells. Stem Cells 2010; 28:674-686.

62. Song Z, Cai J, Liu Y, Zhao D, Yong J, Duo S, Song X, et al. Efficient generation of hepatocyte-like cells from human induced pluripotent stem cells. Cell Res 2009; 19:1233-1242.
63. Si-Tayeb K, Noto F K, Nagaoka M, Li J, Battle M A, Duris C, North P E, et al. Highly efficient generation of human hepatocyte-like cells from induced pluripotent stem cells. Hepatology 2010; 51:297-305.
64. Chen Y F, Tseng C Y, Wang H W, Kuo H C, Yang V W, Lee O K. Rapid generation of mature hepatocyte-like cells from human induced pluripotent stem cells by an efficient three-step protocol. Hepatology 2012; 55:1193-1203.
65. Roelandt P, Vanhove J, Verfaillie C. Directed differentiation of pluripotent stem cells to functional hepatocytes. Methods Mol Biol 2013; 997:141-147.
66. Szkolnicka D, Farnworth S L, Lucendo-Villarin B, Storck C, Zhou W, Iredale J P, Flint O, et al. Accurate Prediction of Drug-Induced Liver Injury Using Stem Cell-Derived Populations. Stem Cells Translational Medicine 2014; 3:141-148.
67. Lacroix D, Sonnier M, Moncion A, Cheron G, Cresteil T. Expression of CYP3A in the human liver—evidence that the shift between CYP3A7 and CYP3A4 occurs immediately after birth. Eur J Biochem 1997; 247:625-634.
68. Morelli L. Postnatal development of intestinal microflora as influenced by infant nutrition. J Nutr 2008; 138:1791S-1795S.
69. Staudinger J L, Goodwin B, Jones S A, Hawkins-Brown D, MacKenzie K I, LaTour A, Liu Y, et al. The nuclear receptor PXR is a lithocholic acid sensor that protects against liver toxicity. Proc Natl Acad Sci USA 2001; 98:3369-3374.
70. Conly J M, Stein K. The production of menaquinones (vitamin K2) by intestinal bacteria and their role in maintaining coagulation homeostasis. Prog Food Nutr Sci 1992; 16:307-343.
71. Shearer M J, Rahim S, Barkhan P, Stimmler L. Plasma vitamin K1 in mothers and their newborn babies. Lancet 1982; 2:460-463.
72. Shearer M J. Vitamin K deficiency bleeding (VKDB) in early infancy. Blood Rev 2009; 23:49-59.
73. Tabb M M, Sun A, Zhou C, Grun F, Errandi J, Romero K, Pham H, et al. Vitamin K2 regulation of bone homeostasis is mediated by the steroid and xenobiotic receptor SXR. J Biol Chem 2003; 278:43919-43927.
74. Ichikawa T, Horie-Inoue K, Ikeda K, Blumberg B, Inoue S. Steroid and xenobiotic receptor SXR mediates vitamin K2-activated transcription of extracellular matrix-related genes and collagen accumulation in osteoblastic cells. J Biol Chem 2006; 281:16927-16934.
75. Amit M, Chebath J, Margulets V, Laevsky I, Miropolsky Y, Shariki K, Peri M, et al. Suspension culture of undifferentiated human embryonic and induced pluripotent stem cells. Stem Cell Rev 2010; 6:248-259.
76. Amit M, Carpenter M K, Inokuma M S, Chiu C P, Harris C P, Waknitz M A, Itskovitz-Eldor J, et al. Clonally derived human embryonic stem cell lines maintain pluripotency and proliferative potential for prolonged periods of culture. Dev Biol 2000; 227:271-278.
77. Kamiya A, Kinoshita T, Miyajima A. Oncostatin M and hepatocyte growth factor induce hepatic maturation via distinct signaling pathways. FEBS Lett 2001; 492:90-94.
78. Donato M T, Jimenez N, Castell J V, Gomez-Lechon M J. Fluorescence-based assays for screening nine cytochrome P450 (P450) activities in intact cells expressing individual human P450 enzymes. Drug Metab Dispos 2004; 32:699-706.
79. Roelandt P, Obeid S, Paeshuyse J, Vanhove J, Van Lommel A, Nahmias Y, Nevens F, et al. Human pluripotent stem cell-derived hepatocytes support complete replication of hepatitis C virus. Journal of Hepatology 2012; 57:246-251.
80. Takebe T, Sekine K, Enomura M, Koike H, Kimura M, Ogaeri T, Zhang R-R, et al. Vascularized and functional human liver from an iPSC-derived organ bud transplant. Nature 2013; advance online publication.
81. Si-Tayeb K, Noto F, Nagaoka M, Li J, Battle M, Duris C, North P, et al. Highly efficient generation of human hepatocyte-like cells from induced pluripotent stem cells. Hepatology 2010; 51:297-305.
82. Chen Y-F, Tseng C-Y, Wang H-W, Kuo H-C, Yang V W, Lee O K. Rapid generation of mature hepatocyte-like cells from human induced pluripotent stem cells by an efficient three-step protocol. Hepatology 2012; 55:1193-1203.
83. Beulens J W, Booth S L, van den Heuvel E G, Stoecklin E, Baka A, Vermeer C. The role of menaquinones (vitamin K(2)) in human health. Br J Nutr 2013; 110:1357-1368.
84. Makishima M, Okamoto A Y, Repa J J, Tu H, Learned R M, Luk A, Hull M V, et al. Identification of a nuclear receptor for bile acids. Science 1999; 284:1362-1365.
85. Avior Y, Bomze D, Ramon O, Nahmias Y. Flavonoids as dietary regulators of nuclear receptor activity. Food Funct 2013; 4:831-844.
86. Gronlund M M, Lehtonen O P, Eerola E, Kero P. Fecal microflora in healthy infants born by different methods of delivery: permanent changes in intestinal flora after cesarean delivery. J Pediatr Gastroenterol Nutr 1999; 28:19-25.
87. Hopkins M J, Macfarlane G T, Furrie E, Fite A, Macfarlane S. Characterisation of intestinal bacteria in infant stools using real-time PCR and northern hybridisation analyses. FEMS Microbiol Ecol 2005; 54:77-85.
88. Hay D C, Fletcher J, Payne C, Terrace J D, Gallagher R C, Snoeys J, Black J R, et al. Highly efficient differentiation of hESCs to functional hepatic endoderm requires ActivinA and Wnt3a signaling. Proc Natl Acad Sci USA 2008; 105:12301-12306.
89. Goodwin B, Hodgson E, Liddle C. The Orphan Human Pregnane X Receptor Mediates the Transcriptional Activation of CYP3A4 by Rifampicin through a Distal Enhancer Module. Molecular Pharmacology 1999; 56:1329-1339.
90. Behnia K, Bhatia S, Jastromb N, Balis U, Sullivan S, Yarmush M, Toner M. Xenobiotic metabolism by cultured primary porcine hepatocytes. Tissue Eng 2000; 6:467-479.

What is claimed is:

1. A method of increasing metabolic maturation of an in vitro cultured immature human hepatocyte, the method comprising contacting, in the absence of any IL6 ligand, the in vitro cultured immature human hepatocyte, which expresses alpha-fetoprotein (AFP) and albumin, with an effective amount of a conjugated fatty acid thereby increasing the metabolic maturation of the immature human hepatocyte.

2. The method of claim 1, wherein said immature human hepatocyte is characterized by an alpha-fetoprotein (AFP)$^+$/Albumin$^+$/CYP3A7$^\pm$/SOX2$^-$/OCT4$^-$ expression signature.

3. The method of claim 1, wherein said immature human hepatocyte does not differentiate into bile duct cells.

4. The method of claim 1, resulting in a mature human hepatocyte characterized by an albumin$^+$/CY3A4$^+$/E-cadherin$^+$/OCT4$^-$/SOX2$^-$/A1AT$^+$/HNF4α$^+$ expression signature.

5. The method of claim 1, wherein said in vitro cultured immature human hepatocyte is obtained by an in vitro differentiation of a human pluripotent stem cell.

6. The method of claim 1, further comprising, prior to said contacting, a step of in vitro differentiating a human hepatoblast into said in vitro cultured human immature hepatocyte.

7. The method of claim 6, wherein said in vitro differentiating is performed by culturing, for a pre-determined time period, said human hepatoblast in a culture medium which comprises an IL6 ligand.

8. The method of claim 7, further comprising, a step of generating said human hepatoblast in a culture medium devoid of said conjugated fatty acid.

9. The method of claim 1, wherein said conjugated fatty acid is provided at a concentration of at least 50 μM.

10. The method of claim 1, wherein said conjugated fatty acid is provided at a concentration of 50-200 μM.

11. The method of claim 1, wherein said conjugated fatty acid is 9-cis, 11-trans conjugated linoleic acid (9CLA).

12. The method of claim 1, wherein the metabolic maturation comprises an increase in a mitochondrial mass per cell as compared to said mitochondrial mass in a control immature human hepatocyte.

13. The method of claim 12, wherein said increase in said mitochondrial mass comprises an increase in a proliferation rate of said mitochondria as compared to a proliferation rate of said mitochondria in a control immature human hepatocyte.

14. The method of claim 1, wherein the metabolic maturation comprises an increase in a maturation state of mitochondria within said immature human hepatocyte as compared to a maturation state of mitochondria within a control immature human hepatocyte.

15. The method of a claim 1, wherein said in vitro cultured immature human hepatocyte is from a newborn human individual.

* * * * *

SEQUENCE LISTING

<160> NUMBER OF SEQ ID NOS: 88

<210> SEQ ID NO 1
<211> LENGTH: 609
<212> TYPE: PRT

<213> ORGANISM: homo sapiens

<400> SEQUENCE: 1

```
Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
    210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
        275                 280                 285

Cys Ser Gln Gln Asp Thr Leu Ser Asn Lys Ile Thr Glu Cys Cys Lys
    290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
        355                 360                 365

Val Ile Leu Arg Val Ala Lys Gly Tyr Gln Glu Leu Leu Glu Lys Cys
    370                 375                 380

Phe Gln Thr Glu Asn Pro Leu Glu Cys Gln Asp Lys Gly Glu Glu Glu
385                 390                 395                 400
```

```
Leu Gln Lys Tyr Ile Gln Glu Ser Gln Ala Leu Ala Lys Arg Ser Cys
                405                 410                 415
Gly Leu Phe Gln Lys Leu Gly Glu Tyr Tyr Leu Gln Asn Ala Phe Leu
            420                 425                 430
Val Ala Tyr Thr Lys Lys Ala Pro Gln Leu Thr Ser Ser Glu Leu Met
        435                 440                 445
Ala Ile Thr Arg Lys Met Ala Ala Thr Ala Thr Cys Cys Gln Leu
    450                 455                 460
Ser Glu Asp Lys Leu Leu Ala Cys Gly Glu Ala Ala Asp Ile Ile
465                 470                 475                 480
Ile Gly His Leu Cys Ile Arg His Glu Met Thr Pro Val Asn Pro Gly
            485                 490                 495
Val Gly Gln Cys Cys Thr Ser Ser Tyr Ala Asn Arg Arg Pro Cys Phe
                500                 505                 510
Ser Ser Leu Val Val Asp Glu Thr Tyr Val Pro Pro Ala Phe Ser Asp
            515                 520                 525
Asp Lys Phe Ile Phe His Lys Asp Leu Cys Gln Ala Gln Gly Val Ala
    530                 535                 540
Leu Gln Thr Met Lys Gln Glu Phe Leu Ile Asn Leu Val Lys Gln Lys
545                 550                 555                 560
Pro Gln Ile Thr Glu Glu Gln Leu Glu Ala Val Ile Ala Asp Phe Ser
            565                 570                 575
Gly Leu Leu Glu Lys Cys Cys Gln Gly Gln Glu Gln Glu Val Cys Phe
                580                 585                 590
Ala Glu Glu Gly Gln Lys Leu Ile Ser Lys Thr Arg Ala Ala Leu Gly
            595                 600                 605
Val

<210> SEQ ID NO 2
<211> LENGTH: 503
<212> TYPE: PRT
<213> ORGANISM: homo sapiens

<400> SEQUENCE: 2

Met Asp Leu Ile Pro Asn Leu Ala Val Glu Thr Trp Leu Leu Leu Ala
1               5                   10                  15
Val Ser Leu Ile Leu Leu Tyr Leu Tyr Gly Thr Arg Thr His Gly Leu
            20                  25                  30
Phe Lys Lys Leu Gly Ile Pro Gly Pro Thr Pro Leu Pro Phe Leu Gly
        35                  40                  45
Asn Ala Leu Ser Phe Arg Lys Gly Tyr Trp Thr Phe Asp Met Glu Cys
    50                  55                  60
Tyr Lys Lys Tyr Arg Lys Val Trp Gly Ile Tyr Asp Cys Gln Gln Pro
65                  70                  75                  80
Met Leu Ala Ile Thr Asp Pro Asp Met Ile Lys Thr Val Leu Val Lys
                85                  90                  95
Glu Cys Tyr Ser Val Phe Thr Asn Arg Arg Pro Phe Gly Pro Val Gly
            100                 105                 110
Phe Met Lys Asn Ala Ile Ser Ile Ala Glu Asp Glu Glu Trp Lys Arg
        115                 120                 125
Ile Arg Ser Leu Leu Ser Pro Thr Phe Thr Ser Gly Lys Leu Lys Glu
    130                 135                 140
Met Val Pro Ile Ile Ala Gln Tyr Gly Asp Val Leu Val Arg Asn Leu
145                 150                 155                 160
```

Arg Arg Glu Ala Glu Thr Gly Lys Pro Val Thr Leu Lys His Val Phe
            165                 170                 175

Gly Ala Tyr Ser Met Asp Val Ile Thr Ser Thr Ser Phe Gly Val Ser
            180                 185                 190

Ile Asp Ser Leu Asn Asn Pro Gln Asp Pro Phe Val Glu Asn Thr Lys
            195                 200                 205

Lys Leu Leu Arg Phe Asn Pro Leu Asp Pro Val Leu Ser Ile Lys
210                 215                 220

Val Phe Pro Phe Leu Thr Pro Ile Leu Glu Ala Leu Asn Ile Thr Val
225                 230                 235                 240

Phe Pro Arg Lys Val Ile Ser Phe Leu Thr Lys Ser Val Lys Gln Ile
            245                 250                 255

Lys Glu Gly Arg Leu Lys Glu Thr Gln Lys His Arg Val Asp Phe Leu
            260                 265                 270

Gln Leu Met Ile Asp Ser Gln Asn Ser Lys Asp Ser Glu Thr His Lys
            275                 280                 285

Ala Leu Ser Asp Leu Glu Leu Met Ala Gln Ser Ile Ile Phe Ile Phe
            290                 295                 300

Ala Gly Tyr Glu Thr Thr Ser Ser Val Leu Ser Phe Ile Ile Tyr Glu
305                 310                 315                 320

Leu Ala Thr His Pro Asp Val Gln Gln Lys Val Gln Lys Glu Ile Asp
            325                 330                 335

Thr Val Leu Pro Asn Lys Ala Pro Pro Thr Tyr Asp Thr Val Leu Gln
            340                 345                 350

Leu Glu Tyr Leu Asp Met Val Val Asn Glu Thr Leu Arg Leu Phe Pro
            355                 360                 365

Val Ala Met Arg Leu Glu Arg Val Cys Lys Lys Asp Val Glu Ile Asn
370                 375                 380

Gly Met Phe Ile Pro Lys Gly Val Val Met Ile Pro Ser Tyr Val
385                 390                 395                 400

Leu His His Asp Pro Lys Tyr Trp Thr Glu Pro Glu Lys Phe Leu Pro
            405                 410                 415

Glu Arg Phe Ser Lys Lys Asn Lys Asp Asn Ile Asp Pro Tyr Ile Tyr
            420                 425                 430

Thr Pro Phe Gly Ser Gly Pro Arg Asn Cys Ile Gly Met Arg Phe Ala
            435                 440                 445

Leu Val Asn Met Lys Leu Ala Leu Val Arg Val Leu Gln Asn Phe Ser
450                 455                 460

Phe Lys Pro Cys Lys Glu Thr Gln Ile Pro Leu Lys Leu Arg Phe Gly
465                 470                 475                 480

Gly Leu Leu Leu Thr Glu Lys Pro Ile Val Leu Lys Ala Glu Ser Arg
            485                 490                 495

Asp Glu Thr Val Ser Gly Ala
            500

<210> SEQ ID NO 3
<211> LENGTH: 502
<212> TYPE: PRT
<213> ORGANISM: homo sapiens

<400> SEQUENCE: 3

Met Ala Leu Ile Pro Asp Leu Ala Met Glu Thr Trp Leu Leu Leu Ala
1               5                   10                  15

Val Ser Leu Val Leu Leu Tyr Leu Tyr Gly Thr His Ser His Gly Leu
            20                  25                  30

```
Phe Lys Lys Leu Gly Ile Pro Gly Pro Thr Pro Leu Pro Phe Leu Gly
         35                  40                  45

Asn Ile Leu Ser Tyr His Lys Gly Phe Cys Met Phe Asp Met Glu Cys
 50                  55                  60

His Lys Lys Tyr Gly Lys Val Trp Gly Phe Tyr Asp Gly Gln Gln Pro
 65              70                  75                  80

Val Leu Ala Ile Thr Asp Pro Asp Met Ile Lys Thr Val Leu Val Lys
                 85                  90                  95

Glu Cys Tyr Ser Val Phe Thr Asn Arg Arg Pro Phe Gly Pro Val Gly
                100                 105                 110

Phe Met Lys Ser Ala Ile Ser Ile Ala Glu Asp Glu Trp Lys Arg
             115                 120                 125

Leu Arg Ser Leu Leu Ser Pro Thr Phe Thr Ser Gly Lys Leu Lys Glu
         130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys Asp Val Phe
                 165                 170                 175

Gly Ala Tyr Ser Met Asp Val Ile Thr Ser Thr Ser Phe Gly Val Asn
                 180                 185                 190

Ile Asp Ser Leu Asn Asn Pro Gln Asp Pro Phe Val Glu Asn Thr Lys
             195                 200                 205

Lys Leu Leu Arg Phe Asp Phe Leu Asp Pro Phe Phe Leu Ser Ile Ile
         210                 215                 220

Phe Pro Phe Leu Ile Pro Ile Leu Glu Val Leu Asn Ile Cys Val Phe
225                 230                 235                 240

Pro Arg Glu Val Thr Asn Phe Leu Arg Lys Ser Val Lys Arg Met Lys
                 245                 250                 255

Glu Ser Arg Leu Glu Asp Thr Gln Lys His Arg Val Asp Phe Leu Gln
             260                 265                 270

Leu Met Ile Asp Ser Gln Asn Ser Lys Glu Thr Glu Ser His Lys Ala
         275                 280                 285

Leu Ser Asp Leu Glu Leu Val Ala Gln Ser Ile Ile Phe Ile Phe Ala
         290                 295                 300

Gly Tyr Glu Thr Thr Ser Ser Val Leu Ser Phe Ile Met Tyr Glu Leu
305                 310                 315                 320

Ala Thr His Pro Asp Val Gln Gln Lys Leu Gln Glu Glu Ile Asp Ala
                 325                 330                 335

Val Leu Pro Asn Lys Ala Pro Pro Thr Tyr Asp Thr Val Leu Gln Met
             340                 345                 350

Glu Tyr Leu Asp Met Val Val Asn Glu Thr Leu Arg Leu Phe Pro Ile
         355                 360                 365

Ala Met Arg Leu Glu Arg Val Cys Lys Lys Asp Val Glu Ile Asn Gly
         370                 375                 380

Met Phe Ile Pro Lys Gly Val Val Met Ile Pro Ser Tyr Ala Leu
385                 390                 395                 400

His Arg Asp Pro Lys Tyr Trp Thr Glu Pro Glu Lys Phe Leu Pro Glu
                 405                 410                 415

Arg Phe Ser Lys Lys Asn Lys Asp Asn Ile Asp Pro Tyr Ile Tyr Thr
             420                 425                 430

Pro Phe Gly Ser Gly Pro Arg Asn Cys Ile Gly Met Arg Phe Ala Leu
         435                 440                 445
```

```
Met Asn Met Lys Leu Ala Leu Ile Arg Val Leu Gln Asn Phe Ser Phe
    450                 455                 460

Lys Pro Cys Lys Glu Thr Gln Ile Pro Leu Lys Leu Ser Leu Gly Gly
465                 470                 475                 480

Leu Leu Gln Pro Glu Lys Pro Val Val Leu Lys Val Glu Ser Arg Asp
                485                 490                 495

Gly Thr Val Ser Gly Ala
                500

<210> SEQ ID NO 4
<211> LENGTH: 503
<212> TYPE: PRT
<213> ORGANISM: homo sapiens

<400> SEQUENCE: 4

Met Ala Leu Ile Pro Asp Leu Ala Met Glu Thr Trp Leu Leu Leu Ala
1               5                   10                  15

Val Ser Leu Val Leu Leu Tyr Leu Tyr Gly Thr His Ser His Gly Leu
                20                  25                  30

Phe Lys Lys Leu Gly Ile Pro Gly Pro Thr Pro Leu Pro Phe Leu Gly
            35                  40                  45

Asn Ile Leu Ser Tyr His Lys Gly Phe Cys Met Phe Asp Met Glu Cys
50                  55                  60

His Lys Lys Tyr Gly Lys Val Trp Gly Phe Tyr Asp Gly Gln Gln Pro
65                  70                  75                  80

Val Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
                100                 105                 110

Phe Met Lys Ser Ala Ile Ser Ile Ala Glu Asp Glu Glu Trp Lys Arg
            115                 120                 125

Leu Arg Ser Leu Leu Ser Pro Thr Phe Thr Ser Gly Lys Leu Lys Glu
130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys Asp Val Phe
                165                 170                 175

Gly Ala Tyr Ser Met Asp Val Ile Thr Ser Thr Ser Phe Gly Val Asn
                180                 185                 190

Ile Asp Ser Leu Asn Asn Pro Gln Asp Pro Phe Val Glu Asn Thr Lys
            195                 200                 205

Lys Leu Leu Arg Phe Asp Phe Leu Asp Pro Phe Phe Leu Ser Ile Thr
210                 215                 220

Val Phe Pro Phe Leu Ile Pro Ile Leu Glu Val Leu Asn Ile Cys Val
225                 230                 235                 240

Phe Pro Arg Glu Val Thr Asn Phe Leu Arg Lys Ser Val Lys Arg Met
                245                 250                 255

Lys Glu Ser Arg Leu Glu Asp Thr Gln Lys His Arg Val Asp Phe Leu
                260                 265                 270

Gln Leu Met Ile Asp Ser Gln Asn Ser Lys Glu Thr Glu Ser His Lys
            275                 280                 285

Ala Leu Ser Asp Leu Glu Leu Val Ala Gln Ser Ile Ile Phe Ile Phe
290                 295                 300

Ala Gly Tyr Glu Thr Thr Ser Ser Val Leu Ser Phe Ile Met Tyr Glu
305                 310                 315                 320
```

Leu Ala Thr His Pro Asp Val Gln Gln Lys Leu Gln Glu Glu Ile Asp
                325                 330                 335

Ala Val Leu Pro Asn Lys Ala Pro Pro Thr Tyr Asp Thr Val Leu Gln
            340                 345                 350

Met Glu Tyr Leu Asp Met Val Val Asn Glu Thr Leu Arg Leu Phe Pro
        355                 360                 365

Ile Ala Met Arg Leu Glu Arg Val Cys Lys Lys Asp Val Glu Ile Asn
    370                 375                 380

Gly Met Phe Ile Pro Lys Gly Val Val Met Ile Pro Ser Tyr Ala
385                 390                 395                 400

Leu His Arg Asp Pro Lys Tyr Trp Thr Glu Pro Glu Lys Phe Leu Pro
                405                 410                 415

Glu Arg Phe Ser Lys Lys Asn Lys Asp Asn Ile Asp Pro Tyr Ile Tyr
            420                 425                 430

Thr Pro Phe Gly Ser Gly Pro Arg Asn Cys Ile Gly Met Arg Phe Ala
        435                 440                 445

Leu Met Asn Met Lys Leu Ala Leu Ile Arg Val Leu Gln Asn Phe Ser
    450                 455                 460

Phe Lys Pro Cys Lys Glu Thr Gln Ile Pro Leu Lys Leu Ser Leu Gly
465                 470                 475                 480

Gly Leu Leu Gln Pro Glu Lys Pro Val Val Leu Lys Val Glu Ser Arg
                485                 490                 495

Asp Gly Thr Val Ser Gly Ala
            500

<210> SEQ ID NO 5
<211> LENGTH: 728
<212> TYPE: PRT
<213> ORGANISM: homo sapiens

<400> SEQUENCE: 5

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser

-continued

```
                180                 185                 190
Asn Pro Glu Val Arg Tyr Glu Val Cys Asp Ile Pro Gln Cys Ser Glu
            195                 200                 205
Val Glu Cys Met Thr Cys Asn Gly Glu Ser Tyr Arg Gly Leu Met Asp
            210                 215                 220
His Thr Glu Ser Gly Lys Ile Cys Gln Arg Trp Asp His Gln Thr Pro
225                 230                 235                 240
His Arg His Lys Phe Leu Pro Glu Arg Tyr Pro Asp Lys Gly Phe Asp
                245                 250                 255
Asp Asn Tyr Cys Arg Asn Pro Asp Gly Gln Pro Arg Pro Trp Cys Tyr
            260                 265                 270
Thr Leu Asp Pro His Thr Arg Trp Glu Tyr Cys Ala Ile Lys Thr Cys
            275                 280                 285
Ala Asp Asn Thr Met Asn Asp Thr Asp Val Pro Leu Glu Thr Thr Glu
            290                 295                 300
Cys Ile Gln Gly Gln Gly Glu Gly Tyr Arg Gly Thr Val Asn Thr Ile
305                 310                 315                 320
Trp Asn Gly Ile Pro Cys Gln Arg Trp Asp Ser Gln Tyr Pro His Glu
                325                 330                 335
His Asp Met Thr Pro Glu Asn Phe Lys Cys Lys Asp Leu Arg Glu Asn
            340                 345                 350
Tyr Cys Arg Asn Pro Asp Gly Ser Glu Ser Pro Trp Cys Phe Thr Thr
            355                 360                 365
Asp Pro Asn Ile Arg Val Gly Tyr Cys Ser Gln Ile Pro Asn Cys Asp
            370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                405                 410                 415
Lys Asn Met Glu Asp Leu His Arg His Ile Phe Trp Glu Pro Asp Ala
            420                 425                 430
Ser Lys Leu Asn Glu Asn Tyr Cys Arg Asn Pro Asp Asp Ala His
            435                 440                 445
Gly Pro Trp Cys Tyr Thr Gly Asn Pro Leu Ile Pro Trp Asp Tyr Cys
            450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
            500                 505                 510
Tyr Arg Asn Lys His Ile Cys Gly Gly Ser Leu Ile Lys Glu Ser Trp
            515                 520                 525
Val Leu Thr Ala Arg Gln Cys Phe Pro Ser Arg Asp Leu Lys Asp Tyr
            530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                565                 570                 575
Ser Asp Leu Val Leu Met Lys Leu Ala Arg Pro Ala Val Leu Asp Asp
            580                 585                 590
Phe Val Ser Thr Ile Asp Leu Pro Asn Tyr Gly Cys Thr Ile Pro Glu
            595                 600                 605
```

```
Lys Thr Ser Cys Ser Val Tyr Gly Trp Gly Tyr Thr Gly Leu Ile Asn
        610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 6
<211> LENGTH: 290
<212> TYPE: PRT
<213> ORGANISM: homo sapiens

<400> SEQUENCE: 6

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
```

```
                    245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
            275                 280                 285

Glu Thr
    290

<210> SEQ ID NO 7
<211> LENGTH: 723
<212> TYPE: PRT
<213> ORGANISM: homo sapiens

<400> SEQUENCE: 7

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
    210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Ala Asp Asn Thr Met
        275                 280                 285

Asn Asp Thr Asp Val Pro Leu Glu Thr Thr Glu Cys Ile Gln Gly Gln
    290                 295                 300

Gly Glu Gly Tyr Arg Gly Thr Val Asn Thr Ile Trp Asn Gly Ile Pro
305                 310                 315                 320
```

```
Cys Gln Arg Trp Asp Ser Gln Tyr Pro His Glu His Asp Met Thr Pro
                325                 330                 335
Glu Asn Phe Lys Cys Lys Asp Leu Arg Glu Asn Tyr Cys Arg Asn Pro
            340                 345                 350
Asp Gly Ser Glu Ser Pro Trp Cys Phe Thr Thr Asp Pro Asn Ile Arg
        355                 360                 365
Val Gly Tyr Cys Ser Gln Ile Pro Asn Cys Asp Met Ser His Gly Gln
    370                 375                 380
Asp Cys Tyr Arg Gly Asn Gly Lys Asn Tyr Met Gly Asn Leu Ser Gln
385                 390                 395                 400
Thr Arg Ser Gly Leu Thr Cys Ser Met Trp Asp Lys Asn Met Glu Asp
                405                 410                 415
Leu His Arg His Ile Phe Trp Glu Pro Asp Ala Ser Lys Leu Asn Glu
            420                 425                 430
Asn Tyr Cys Arg Asn Pro Asp Asp Ala His Gly Pro Trp Cys Tyr
        435                 440                 445
Thr Gly Asn Pro Leu Ile Pro Trp Asp Tyr Cys Pro Ile Ser Arg Cys
    450                 455                 460
Glu Gly Asp Thr Thr Pro Thr Ile Val Asn Leu Asp His Pro Val Ile
465                 470                 475                 480
Ser Cys Ala Lys Thr Lys Gln Leu Arg Val Val Asn Gly Ile Pro Thr
                485                 490                 495
Arg Thr Asn Ile Gly Trp Met Val Ser Leu Arg Tyr Arg Asn Lys His
            500                 505                 510
Ile Cys Gly Gly Ser Leu Ile Lys Glu Ser Trp Val Leu Thr Ala Arg
        515                 520                 525
Gln Cys Phe Pro Ser Arg Asp Leu Lys Asp Tyr Glu Ala Trp Leu Gly
    530                 535                 540
Ile His Asp Val His Gly Arg Gly Asp Glu Lys Cys Lys Gln Val Leu
545                 550                 555                 560
Asn Val Ser Gln Leu Val Tyr Gly Pro Glu Gly Ser Asp Leu Val Leu
                565                 570                 575
Met Lys Leu Ala Arg Pro Ala Val Leu Asp Asp Phe Val Ser Thr Ile
            580                 585                 590
Asp Leu Pro Asn Tyr Gly Cys Thr Ile Pro Glu Lys Thr Ser Cys Ser
        595                 600                 605
Val Tyr Gly Trp Gly Tyr Thr Gly Leu Ile Asn Tyr Asp Gly Leu Leu
    610                 615                 620
Arg Val Ala His Leu Tyr Ile Met Gly Asn Glu Lys Cys Ser Gln His
625                 630                 635                 640
His Arg Gly Lys Val Thr Leu Asn Glu Ser Glu Ile Cys Ala Gly Ala
                645                 650                 655
Glu Lys Ile Gly Ser Gly Pro Cys Glu Gly Asp Tyr Gly Gly Pro Leu
            660                 665                 670
Val Cys Glu Gln His Lys Met Arg Met Val Leu Gly Val Ile Val Pro
        675                 680                 685
Gly Arg Gly Cys Ala Ile Pro Asn Arg Pro Gly Ile Phe Val Arg Val
    690                 695                 700
Ala Tyr Tyr Ala Lys Trp Ile His Lys Ile Ile Leu Thr Tyr Lys Val
705                 710                 715                 720
Pro Gln Ser

<210> SEQ ID NO 8
```

<211> LENGTH: 285
<212> TYPE: PRT
<213> ORGANISM: homo sapiens

<400> SEQUENCE: 8

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Glu Thr
        275                 280                 285
```

<210> SEQ ID NO 9
<211> LENGTH: 210
<212> TYPE: PRT
<213> ORGANISM: homo sapiens

<400> SEQUENCE: 9

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
50                  55                  60
```

-continued

```
Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
        130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
            195                 200                 205

Gly Lys
    210

<210> SEQ ID NO 10
<211> LENGTH: 573
<212> TYPE: PRT
<213> ORGANISM: homo sapiens

<400> SEQUENCE: 10

Met Leu Arg Leu Pro Thr Val Phe Arg Gln Met Arg Pro Val Ser Arg
 1               5                  10                  15

Val Leu Ala Pro His Leu Thr Arg Ala Tyr Ala Lys Asp Val Lys Phe
                20                  25                  30

Gly Ala Asp Ala Arg Ala Leu Met Leu Gln Gly Val Asp Leu Leu Ala
            35                  40                  45

Asp Ala Val Ala Val Thr Met Gly Pro Lys Gly Arg Thr Val Ile Ile
        50                  55                  60

Glu Gln Ser Trp Gly Ser Pro Lys Val Thr Lys Asp Gly Val Thr Val
 65                  70                  75                  80

Ala Lys Ser Ile Asp Leu Lys Asp Lys Tyr Lys Asn Ile Gly Ala Lys
                 85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
            115                 120                 125

Glu Lys Ile Ser Lys Gly Ala Asn Pro Val Glu Ile Arg Arg Gly Val
        130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
            195                 200                 205

Asp Glu Leu Glu Ile Ile Glu Gly Met Lys Phe Asp Arg Gly Tyr Ile
```

```
                210                 215                 220
Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
                260                 265                 270

Ile Ile Ala Glu Asp Val Asp Gly Glu Ala Leu Ser Thr Leu Val Leu
                275                 280                 285

Asn Arg Leu Lys Val Gly Leu Gln Val Val Ala Val Lys Ala Pro Gly
                290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
                340                 345                 350

Asp Asp Ala Met Leu Leu Lys Gly Lys Gly Asp Lys Ala Gln Ile Glu
                355                 360                 365

Lys Arg Ile Gln Glu Ile Ile Glu Gln Leu Asp Val Thr Thr Ser Glu
                370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
                420                 425                 430

Glu Glu Gly Ile Val Leu Gly Gly Cys Ala Leu Leu Arg Cys Ile
                435                 440                 445

Pro Ala Leu Asp Ser Leu Thr Pro Ala Asn Glu Asp Gln Lys Ile Gly
                450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
                500                 505                 510

Met Val Glu Lys Gly Ile Ile Asp Pro Thr Lys Val Val Arg Thr Ala
                515                 520                 525

Leu Leu Asp Ala Ala Gly Val Ala Ser Leu Leu Thr Thr Ala Glu Val
                530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Met Phe
                565                 570

<210> SEQ ID NO 11
<211> LENGTH: 573
<212> TYPE: PRT
<213> ORGANISM: homo sapiens

<400> SEQUENCE: 11

Met Leu Arg Leu Pro Thr Val Phe Arg Gln Met Arg Pro Val Ser Arg
1               5                   10                  15
```

```
Val Leu Ala Pro His Leu Thr Arg Ala Tyr Ala Lys Asp Val Lys Phe
             20                  25                  30

Gly Ala Asp Ala Arg Ala Leu Met Leu Gln Gly Val Asp Leu Leu Ala
         35                  40                  45

Asp Ala Val Ala Val Thr Met Gly Pro Lys Gly Arg Thr Val Ile Ile
     50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                 85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
        355                 360                 365

Lys Arg Ile Gln Glu Ile Ile Glu Gln Leu Asp Val Thr Thr Ser Glu
    370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Gly Cys Ala Leu Leu Arg Cys Ile
```

```
                435               440               445
Pro Ala Leu Asp Ser Leu Thr Pro Ala Asn Glu Asp Gln Lys Ile Gly
        450                   455               460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                    485                 490                 495

Ser Ser Ser Glu Val Gly Tyr Asp Ala Met Ala Gly Asp Phe Val Asn
                500                 505                 510

Met Val Glu Lys Gly Ile Ile Asp Pro Thr Lys Val Val Arg Thr Ala
                515                 520                 525

Leu Leu Asp Ala Ala Gly Val Ala Ser Leu Leu Thr Thr Ala Glu Val
            530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Gly Met Phe
                        565                 570

<210> SEQ ID NO 12
<211> LENGTH: 2057
<212> TYPE: DNA
<213> ORGANISM: homo sapiens

<400> SEQUENCE: 12
atattgtgct tccaccactg ccaataacaa ataactagc aaccatgaag tgggtggaat      60
caatttttt aatttccta ctaaatttta ctgaatccag aacactgcat agaaatgaat      120
atggaatagc ttccatattg gattcttacc aatgtactgc agagataagt ttagctgacc      180
tggctaccat atttttgcc cagtttgttc aagaagccac ttacaaggaa gtaagcaaaa      240
tggtgaaaga tgcattgact gcaattgaga aacccactgg agatgaacag tcttcagggt      300
gtttagaaaa ccagctacct gccttctgg aagaactttg ccatgagaaa gaaattttgg      360
agaagtacgg acattcagac tgctgcagcc aaagtgaaga gggaagacat aactgttttc      420
ttgcacacaa aaagcccact ccagcatcga tcccactttt ccaagttcca gaacctgtca      480
caagctgtga agcatatgaa aagacaggg agacattcat gaacaaattc atttatgaga      540
tagcaagaag gcatcccttc ctgtatgcac ctacaattct tctttgggct gctcgctatg      600
acaaaataat tccatcttgc tgcaaagctg aaaatgcagt tgaatgcttc caaacaaagg      660
cagcaacagt tacaaaagaa ttaagagaaa gcagcttgtt aaatcaacat gcatgtgcag      720
taatgaaaaa ttttgggacc cgaactttcc aagccataac tgttactaaa ctgagtcaga      780
agtttaccaa agttaatttt actgaaatcc agaaactagt cctggatgtg gcccatgtac      840
atgagcactg ttgcagagga gatgtgctgg attgtctgca ggatggggaa aaaatcatgt      900
cctacatatg ttctcaacaa gacactctgt caaacaaaat aacagaatgc tgcaaactga      960
ccacgctgga acgtggtcaa tgtataattc atgcagaaaa tgatgaaaaa cctgaaggtc      1020
tatctccaaa tctaaacagg tttttaggag atagagattt taaccaattt tcttcagggg      1080
aaaaaaatat cttcttggca agttttgttc atgaatattc aagaagacat cctcagcttg      1140
ctgtctcagt aattctaaga gttgctaaag gataccagga gttattggag aagtgtttcc      1200
agactgaaaa ccctcttgaa tgccaagata aggagaaga agaattacag aaatacatcc      1260
aggagagcca agcattggca aagcgaagct gcggcctctt ccagaaacta ggagaatatt      1320
acttacaaaa tgcgtttctc gttgcttaca caaagaaagc ccccagctg acctcgtcgg      1380
```

```
agctgatggc catcaccaga aaaatggcag ccacagcagc cacttgttgc caactcagtg    1440
aggacaaact attggcctgt ggcgaggag cggctgacat tattatcgga cacttatgta     1500
tcagacatga aatgactcca gtaaaccctg tgttggcca gtgctgcact tcttcatatg     1560
ccaacaggag gccatgcttc agcagcttgg tggtggatga acatatgtc cctcctgcat     1620 tctctgatga caagttcatt ttccataagg atctgtgcca agctcagggt gtagcgctgc    1680
aaacgatgaa gcaagagttt ctcattaacc ttgtgaagca aaagccacaa ataacagagg    1740
aacaacttga ggctgtcatt gcagatttct caggcctgtt ggagaaatgc tgccaaggcc    1800
aggaacagga agtctgcttt gctgaagagg acaaaaact gatttcaaaa actcgtgctg     1860
ctttgggagt ttaaattact tcaggggaag agaagacaaa acgagtcttt cattcggtgt    1920
gaacttttct ctttaatttt aactgattta acacttttg tgaattaatg aaatgataaa     1980
gacttttatg tgagatttcc ttatcacaga aataaaatat ctccaaatgt ttccttttca    2040
aaaaaaaaaa aaaaaaa                                                   2057

<210> SEQ ID NO 13
<211> LENGTH: 2099
<212> TYPE: DNA
<213> ORGANISM: homo sapiens

<400> SEQUENCE: 13
aatcactgct gtgcagggca ggaaagctcc acacacacag cccagcaaac agcagcacgc      60
tgctgaaaaa aagactcaga ggagagagat aaggaaggaa agtagtgatg gatctcatcc     120
caaacttggc cgtggaaacc tggcttctcc tggctgtcag cctgatactc ctctatctat     180
atggaacccg tacacatgga ctttttaaga agcttggaat tccagggccc acacctctgc     240
cttttttggg aaatgctttg tccttccgta agggctattg gacgtttgac atggaatgtt    300
ataaaaagta tagaaaagtc tggggtattt atgactgtca acagcctatg ctggctatca    360
cagatcccga catgatcaaa acagtgctag tgaaagaatg ttattctgtc ttcacaaacc    420
ggaggccttt cgggccagtg ggatttatga aaaatgccat ctctatagct gaggatgaag    480 aatgaagag aatacgatca ttgctgtctc caacattcac cagcggaaaa ctcaaggaga     540
tggtccctat cattgcccag tatggagatg tgttggtgag aaatctgagg cgggaagcag    600
agacaggcaa gcctgtcacc ttgaaacacg tctttgggc ctacagcatg gatgtgatca     660
ctagcacatc atttggagtg agcatcgact ctctcaacaa tccacaagac cctttgtgg    720 aaaacaccaa gaagctttta agatttaatc cattagatcc attcgttctc tcaataaaag    780
tctttccatt ccttacccca attcttgaag cattaaatat cactgtgttt ccaagaaaag    840
ttataagttt tctaacaaaa tctgtaaaac agataaaaga aggtcgcctc aaagagacac    900
aaaagcaccg agtggatttc cttcagctga tgattgactc tcagaattca aaagactctg    960
agacccacaa agctctgtct gatctggagc tcatggccca atcaattatc tttatttttg    1020
ctggctatga aaccacgagc agtgttctct ccttcattat atatgaactg gccactcacc    1080
ctgatgtcca gcagaaagtg cagaaggaaa ttgatacagt tttacccaat aaggcaccac    1140
ccacctatga tactgtgcta cagttggagt atcttgacat ggtggtgaat gaaacactca    1200
gattattccc agttgctatg agacttgaga gggtctgcaa aaagatgtt gaaatcaatg     1260 ggatgtttat tccaaagggg gtggtggtga tgattccaag ctatgttctt catcatgacc    1320
caaagtactg gacagagcct gagaagttcc tccctgaaag gttcagtaaa aagaacaagg    1380
```

```
acaacataga tccttacata tacacaccct ttggaagtgg acccagaaac tgcattggca   1440
tgaggtttgc tctcgtgaac atgaaacttg ctctagtcag agtccttcag aacttctcct   1500
tcaaaccttg taaagaaaca cagatccccc tgaaattacg ctttggagga cttcttctaa   1560
cagaaaaacc cattgttcta aaggctgagt caagggatga gaccgtaagt ggagcctgat   1620
ttccctaagg acttctggtt tgctctttaa gaaagctgtg ccccagaaca ccagagacct   1680
caaattactt tacaaataga accctgaaat gaagacgggc ttcatccaat gtgctgcata   1740
aataatcagg gattctgtac gtgcattgtg ctctctcatg gtctgtatag agtgttatac   1800
ttggtaatat agaggagatg accaaatcag tgctggggaa gtagatttgg cttctctgct   1860
tctcatagga ctatctccac cacccccagt tagcaccatt aactcctcct gagctctgat   1920
aacataatta acatttctca ataatttcaa ccacaatcat taataaaaat aggaattatt   1980
ttgatggctc taacagtgac atttatatca tgtgttatat ctgtagtatt ctatagtaag   2040
ctttatatta agcaaatcaa taaaaacctc tttacaaaag taaaaaaaaa aaaaaaaaa    2099
```

<210> SEQ ID NO 14
<211> LENGTH: 2789
<212> TYPE: DNA
<213> ORGANISM: homo sapiens

<400> SEQUENCE: 14

```
aatcactgct gtgcagggca ggaaagctcc atgcacatag cccagcaaag agcaacacag     60
agctgaaagg aagactcaga ggagagagat aagtaaggaa agtagtgatg gctctcatcc    120
cagacttggc catggaaacc tggcttctcc tggctgtcag cctggtgctc ctctatctat    180
atggaaccca ttcacatgga ctttttaaga agcttggaat tccagggccc acacctctgc    240
ctttttttggg aaatattttg tcctaccata agggcttttg tatgtttgac atggaatgtc    300
ataaaaagta tggaaaagtg tggggctttt atgatggtca acagcctgtg ctggctatca    360
cagatcctga catgatcaaa acagtgctag tgaaagaatg ttattctgtc ttcacaaacc    420
ggaggccttt tggtccagtg ggatttatga aaagtgccat ctctatagct gaggatgaag    480
aatggaagag attacgatca ttgctgtctc caaccttcac cagtggaaaa ctcaaggaga    540
tggtccctat cattgcccag tatggagatg tgttggtgag aaatctgagg cgggaagcag    600
agacaggcaa gcctgtcacc ttgaaagacg tctttggggc ctacagcatg gatgtgatca    660
ctagcacatc atttggagtg aacatcgact ctctcaacaa tccacaagac ccctttgtgg    720
aaaacaccaa gaagctttta agatttgatt ttttggatcc attctttctc tcaataatct    780
ttccattcct catcccaatt cttgaagtat taaatatctg tgtgtttcca agagaagtta    840
caaatttttt aagaaaatct gtaaaaagga tgaaagaaag tcgcctcgaa gatacacaaa    900
agcaccgagt ggatttcctt cagctgatga ttgactctca gaattcaaaa gaaactgagt    960
cccacaaagc tctgtccgat ctggagctcg tggcccaatc aattatcttt atttttgctg   1020
gctatgaaac cacgagcagt gttctctcct tcattatgta tgaactggcc actcaccctg   1080
atgtccagca gaaactgcag gaggaaattg atgcagtttt acccaataag gcaccaccca   1140
cctatgatac tgtgctacag atggagtatc ttgacatggt ggtgaatgaa acgctcagat   1200
tattcccaat tgctatgaga cttgagaggg tctgcaaaaa agatgttgag atcaatggga   1260
tgttcattcc caaaggggtg gtggtgatga ttccaagcta tgctcttcac cgtgacccaa   1320
agtactggac agagcctgag aagttcctcc ctgaaagatt cagcaagaag aacaaggaca   1380
acatagatcc ttacatatac acaccctttg gaagtggacc cagaaactgc attggcatga   1440
```

```
ggtttgctct catgaacatg aaacttgctc taatcagagt ccttcagaac ttctccttca    1500
aaccttgtaa agaaacacag atcccoctga aattaagctt aggaggactt cttcaaccag    1560
aaaaacccgt tgttctaaag gttgagtcaa gggatggcac cgtaagtgga gcctgaattt    1620
tcctaaggac ttctgctttg ctcttcaaga atctgtgcc tgagaacacc agagacctca    1680
aattactttg tgaatagaac tctgaaatga agatgggctt catccaatgg actgcataaa    1740
taaccgggga ttctgtacat gcattgagct ctctcattgt ctgtgtagag tgttatactt    1800
gggaatataa aggaggtgac caaatcagtg tgaggaggta gatttggctc ctctgcttct    1860
cacgggacta tttccaccac ccccagttag caccattaac tcctcctgag ctctgataag    1920
agaatcaaca tttctcaata atttcctcca caaattatta atgaaaataa gaattatttt    1980
gatggctcta caatgacat ttatatcaca tgttttctct ggagtattct ataagtttta    2040
tgttaaatca ataaagacca ctttacaaaa gtattatcag atgctttcct gcacattaag    2100
gagaaatcta tagaactgaa tgagaaccaa caagtaaata tttttggtca ttgtaatcac    2160
tgttggcgtg gggccttttgt cagaactaga atttgattat taacataggt gaaagttaat    2220
ccactgtgac tttgcccatt gtttagaaag aatattcata gtttaattat gccttttttg    2280
atcaggcaca gtggctcacg cctgtaatcc tagcagtttg ggaggctgag ccgggtggat    2340
cgcctgaggt caggagttca agacaagcct ggcctacatg gttgaaaccc catctctact    2400
aaaaatacac aaattagcta ggcatggtgg actcgcctgt aatctcacta cacaggaggc    2460
tgaggcagga gaatcacttg aacctgggag gcggatgttg aagtgagctg agattgcacc    2520
actgcactcc agtctgggtg agagtgagac tcagtcttaa aaaaatatgc ctttttgaag    2580
cacgtacatt ttgtaacaaa gaactgaagc tcttattata ttattagttt tgatttaatg    2640
ttttcagccc atctcctttc atatttctgg gagacagaaa acatgtttcc ctacacctct    2700
tgcattccat cctcaacacc caactgtctc gatgcaatga acacttaata aaaaacagtc    2760
gattggtcaa ttgattgagc aataagcct                                     2789
```

<210> SEQ ID NO 15
<211> LENGTH: 2792
<212> TYPE: DNA
<213> ORGANISM: homo sapiens

<400> SEQUENCE: 15

```
aatcactgct gtgcagggca ggaaagctcc atgcacatag cccagcaaag agcaacacag     60
agctgaaagg aagactcaga ggagagagat aagtaaggaa agtagtgatg gctctcatcc    120
cagacttggc catggaaacc tggcttctcc tggctgtcag cctggtgctc ctctatctat    180
atggaaccca ttcacatgga ctttttaaga agcttggaat tccagggccc acacctctgc    240
cttttttggg aaatattttg tcctaccata agggcttttg tatgtttgac atggaatgtc    300
ataaaaagta tggaaaagtg tggggctttt atgatggtca acagcctgtg ctggctatca    360
cagatcctga catgatcaaa acagtgctag tgaaagaatg ttattctgtc ttcacaaacc    420
ggaggccttt tggtccagtg ggattttatga aaagtgccat ctctatagct gaggatgaag    480
aatggaagag attacgatca ttgctgtctc caaccttcac cagtggaaaa ctcaaggaga    540
tggtccctat cattgcccag tatggagatg tgttggtgag aaatctgagg cgggaagcag    600
agacaggcaa gcctgtcacc ttgaaagacg tcttgggc ctacagcatg gatgtgatca    660
ctagcacatc atttggagtg aacatcgact ctctcaacaa tccacaagac cccttgtgg    720
```

```
aaaacaccaa gaagctttta agatttgatt ttttggatcc attctttctc tcaataacag       780
tctttccatt cctcatccca attcttgaag tattaaatat ctgtgtgttt ccaagagaag       840
ttacaaattt tttaagaaaa tctgtaaaaa ggatgaaaga aagtcgcctc gaagatacac       900
aaaagcaccg agtggatttc cttcagctga tgattgactc tcagaattca aaagaaactg       960
agtcccacaa agctctgtcc gatctggagc tcgtggccca atcaattatc tttattttg       1020 ctggctatga aaccacgagc agtgttctct ccttcattat gtatgaactg gccactcacc      1080
ctgatgtcca gcagaaactg caggaggaaa ttgatgcagt tttacccaat aaggcaccac      1140
ccacctatga tactgtgcta cagatggagt atcttgacat ggtggtgaat gaaacgctca      1200
gattattccc aattgctatg agacttgaga gggtctgcaa aaaagatgtt gagatcaatg      1260
ggatgttcat tcccaagggg gtggtggtga tgattccaag ctatgctctt caccgtgacc      1320
caaagtactg gacagagcct gagaagttcc tccctgaaag attcagcaag aagaacaagg      1380
acaacataga tccttacata tacacaccct ttggaagtgg acccagaaac tgcattggca      1440
tgaggtttgc tctcatgaac atgaaacttg ctctaatcag agtccttcag aacttctcct      1500
tcaaaccttg taaagaaaca cagatccccc tgaaattaag cttaggagga cttcttcaac      1560
cagaaaaacc cgttgttcta aaggttgagt caagggatgg caccgtaagt ggagcctgaa      1620
ttttcctaag gacttctgct ttgctcttca agaaatctgt gcctgagaac accagagacc      1680
tcaaattact ttgtgaatag aactctgaaa tgaagatggg cttcatccaa tggactgcat      1740
aaataaccgg ggattctgta catgcattga gctctctcat tgtctgtgta gagtgttata      1800
cttgggaata taaggaggt gaccaaatca gtgtgaggag gtagatttgg ctcctctgct       1860
tctcacggga ctatttccac cacccccagt tagcaccatt aactcctcct gagctctgat      1920
aagagaatca acatttctca ataatttcct ccacaaatta ttaatgaaaa taagaattat      1980
tttgatggct ctaacaatga catttatatc acatgttttc tctggagtat tctataagtt      2040
ttatgttaaa tcaataaaga ccactttaca aaagtattat cagatgcttt cctgcacatt      2100
aaggagaaat ctatagaact gaatgagaac caacaagtaa atattttggg tcattgtaat      2160
cactgttggc gtggggcctt tgtcagaact agaatttgat tattaacata ggtgaaagtt      2220
aatccactgt gactttgccc attgtttaga agaatattc atagtttaat tatgcctttt       2280
ttgatcaggc acagtggctc acgcctgtaa tcctagcagt ttgggaggct gagccgggtg      2340
gatcgcctga ggtcaggagt tcaagacaag cctggcctac atggttgaaa ccccatctct      2400
actaaaaata cacaaattag ctaggcatgg tggactcgcc tgtaatctca ctacacagga      2460
ggctgaggca ggagaatcac ttgaacctgg gaggcggatg ttgaagtgag ctgagattgc      2520
accactgcac tccagtctgg gtgagagtga gactcagtct aaaaaaata tgccttttg       2580 aagcacgtac attttgtaac aaagaactga agctcttatt atattattag ttttgattta      2640
atgttttcag cccatctcct ttcatatttc tgggagacag aaaacatgtt ccctacacc       2700 tcttgcattc catcctcaac acccaactgt ctcgatgcaa tgaacactta ataaaaaaca      2760
gtcgattggt caattgattg agcaataagc ct                                    2792
```

<210> SEQ ID NO 16
<211> LENGTH: 6002
<212> TYPE: DNA
<213> ORGANISM: homo sapiens

<400> SEQUENCE: 16

```
gaggaaagga gggggctgga agagagtaaa gggctgttgt taaacagttt cttaccgtaa        60
```

```
gagggagttc agacctagat ctttccagtt aatcacacaa caaacttagc tcatcgcaat      120
aaaaagcagc tcagagccga ctggctcttt taggcactga ctccgaacag gattctttca      180
cccaggcatc tcctccagag ggatccgcca gcccgtccag cagcaccatg tgggtgacca      240
aactcctgcc agcccgctg ctgcagcatg tcctcctgca tctcctcctg ctccccatcg       300
ccatccccta tgcagaggga caaaggaaaa gaagaaatac aattcatgaa ttcaaaaaat      360
cagcaaagac taccctaatc aaaatagatc cagcactgaa gataaaaacc aaaaagtga      420 atactgcaga ccaatgtgct aatagatgta ctaggaataa aggacttcca ttcacttgca     480
aggcttttgt ttttgataaa gcaagaaaac aatgcctctg gttccccttc aatagcatgt     540
caagtggagt gaaaaagaa tttggccatg aatttgacct ctatgaaaac aaagactaca      600
ttagaaactg catcattggt aaaggacgca gctacaaggg aacagtatct atcactaaga     660
gtggcatcaa atgtcagccc tggagttcca tgataccaca cgaacacagc ttttttgcctt    720 cgagctatcg gggtaaagac ctacaggaaa actactgtcg aaatcctcga ggggaagaag     780
ggggaccctg gtgtttcaca agcaatccag aggtacgcta cgaagtctgt gacattcctc     840
agtgttcaga agttgaatgc atgacctgca atggggagag ttatcgaggt ctcatggatc     900
atacagaatc aggcaagatt tgtcagcgct gggatcatca gacaccacac cggcacaaat     960
tcttgcctga agatatccc gacaagggct tgatgataa ttattgccgc aatcccgatg      1020
gccagccgag gccatggtgc tatactcttg accctcacac ccgctgggag tactgtgcaa    1080
ttaaaacatg cgctgacaat actatgaatg acactgatgt tcctttggaa caactgaat    1140 gcatccaagg tcaaggagaa ggctacaggg gcactgtcaa taccatttgg aatggaattc    1200
catgtcagcg ttgggattct cagtatcctc acgagcatga catgactcct gaaaatttca    1260
agtgcaagga cctacgagaa aattactgcc gaaatccaga tgggtctgaa tcaccctggt    1320
gttttaccac tgatccaaac atccgagttg gctactgctc ccaaattcca aactgtgata    1380
tgtcacatgg acaagattgt tatcgtggga atggcaaaaa ttatatgggc aacttatccc    1440
aaacaagatc tggactaaca tgttcaatgt gggacaagaa catggaagac ttacatcgtc    1500
atatcttctg gaaccagat gcaagtaagc tgaatgagaa ttactgccga aatccagatg    1560
atgatgctca tggaccctgg tgctacacgg gaaatccact cattccttgg gattattgcc    1620
ctatttctcg ttgtgaaggt gataccacac ctacaatagt caatttagac catcccgtaa    1680
tatcttgtgc caaaacgaaa caattgcgag ttgtaaatgg gattccaaca cgaacaaaca    1740
taggatggat ggttagtttg agatacagaa ataaacatat ctgcggagga tcattgataa    1800
aggagagttg ggttcttact gcacgacagt gtttcccttc tcgagacttg aaagattatg    1860
aagcttggct tggaattcat gatgtccacg gaagaggaga tgagaaatgc aaacaggttc    1920
tcaatgtttc ccagctggta tatggccctg aaggatcaga tctggtttta atgaagcttg    1980
ccaggcctgc tgtcctggat gattttgtta gtacgattga tttacctaat tatgatgca    2040 caattcctga aaagaccagt tgcagtgttt atggctgggg ctacactgga ttgatcaact    2100
atgatggcct attacgagtg gcacatctct atataatggg aaatgagaaa tgcagccagc    2160
atcatcgagg aaggtgact ctgaatgagt ctgaaatatg tgctgggct gaaagattg     2220 gatcaggacc atgtgagggg gattatggtg gcccacttgt ttgtgagcaa cataaaatga    2280
gaatggttct tggtgtcatt gttcctggtc gtggatgtgc cattccaaat cgtcctggta    2340
tttttgtccg agtagcatat tatgcaaaat ggatacacaa aattatttta acatataagg    2400
```

```
taccacagtc atagctgaag taagtgtgtc tgaagcaccc accaatacaa ctgtctttta      2460
catgaagatt tcagagaatg tggaatttaa aatgtcactt acaacaatcc taagacaact      2520
actggagagt catgtttgtt gaaattctca ttaatgttta tgggtgtttt ctgttgtttt      2580
gtttgtcagt gttattttgt caatgttgaa gtgaattaag gtacatgcaa gtgtaataac      2640
atatctcctg aagatacttg aatggattaa aaaaacacac aggtatattt gctggatgat      2700
aaagatttca tgggaaaaaa aatcaattaa tctgtctaag ctgctttctg atgttggttt      2760
cttaataatg agtaaaccac aaattaaatg ttatttaaac ctcaccaaaa caatttatac      2820
cttgtgtccc taaattgtag ccctatatta aattatatta catttcatat gctatatgtt      2880
atagttcatt catttctctt caccatgtat cctgcaatac tggtacacga acacactttt      2940
tacaaaacca catacccatg tacacatgcc taggtacaca tgtgcatgca ctacagttta      3000
aattatggtg tacctaatgt aacccctaaa tattttagaa gtatgtacct atagttttac      3060
ctcaaaaaaa ccagaaatct ctaaagacca gtagaaatat taaaaaatga tgcaagatca      3120
aaatgattag ctaattctcc atacataatc tgcagatgat cttctttggt tggcatttca      3180
ggtgtggcca tcacccagag ttaaataaca cctaatctag gtgtttacat gtattcatta      3240
tcctagttat ttcatgtagt ttctaattct taaaggaaag agggtaatag ttctatttgt      3300
gtaatttgtt tcctccaaac ttaaggccac ttatttacac aagatatttg tagatctatt      3360
ttcctaaagc atttcttaag tgctcagatc agtatctaat tgaagaagtt taaaagtgtt      3420
ttggtcatta aaaatgtact taaataggtt aaatctaagc cttgctgctg tgattggctt      3480
ctagctcact gcctttaaat tttaaaaaat ttaagaggaa aatttccaag tctccaaagt      3540
tttataaata cccttcatca agtcatgcat taaagtatat attggagaaa aaaataaaaa      3600
tacttttctc aacctggaag attttagcct aataaagctt ttttgaagta aaagacaact      3660
tgtaaaagga aagaaactag tttgtctcaa ctctgtattc atttattttt tttttgaagt      3720
agagtggaat ctgttgaatc agatatttta tcaagatatg tttatttttt cttatttcat      3780
tttacaaagt tcactcctaa tgccatatgt aacagacatt taaattttgt gttctgtata      3840
acagccaaat tatcatattt atcattgtat ttgtcatgct tagctaaaga tcatgtattt      3900
gttgagaaat agaataacaa aaagtaatag gataggcttt gaattttttgc agaaatcttc      3960 ctgtacaaaa cacctttaaa aataattttt tgaatggtgt gaatccagta gtcccatttc      4020
tctgacttag ttttcttgag tgatttttat caaggccaag tccccaaaca attccctacc      4080
agctctttag agtactgttc aatctggact aaaatggttt taagtttatg gagagcttag      4140
tccacagaat atagggcggc gagtccagaa atgcttatac aattttttt tcataataag      4200 atatgtgctg gcatcaagaa acttaaagtg gaagcaaaaa gacatccaac tagttgctgg      4260
tctctatcat cttatctgat ggtatttcta ttttccttat ataatacacc attttagtaa      4320
gaactcctag aaatttcaag agcatattgc caaaatataa agtatatttc atagtttctt      4380
ctggctgaac cagtgaaatt ttattattgc atattaatga tatttgtaaa acttttataa      4440
aaattgtcat aattttaaat actcacattt taaaaatact tctttaatga ctcttcctct      4500
aaatttcctg gaaatacaga taagattag ctagatacaa gatacagcta agtatttaga      4560
cattttgagg ctagtatttt tcattttatt aaaggctaaa aacaatacca ccaataaatc      4620
atcaaacaaa ccgtacaaag taattctctc tttgggaggc tcctttcgtg atagagggac      4680
atgggtggaa ttgacaatga aacttagatg aacaaggtcc atgttatttt aggtggtaga      4740
acagggtaga gtcatgtcat tatttgctgg tggaagacac tatttaccag gtgttctttg      4800
```

| | | | | |
|---|---|---|---|---|
| ctgaataaat | cattaaacat | ttttaaaaat | ccaacaatcc | actttatttt | gtgtcattga | 4860 |
| caaaaggatc | ttttaaatca | gaaggtttca | atgcaatttt | tggtttggct | gtttgaataa | 4920 |
| tggttatgta | ctgttataat | tgtagacatt | ttctcacgtc | taccaggaat | tgaagtgtaa | 4980 |
| aactaaaata | ttttcataa | tgcctctgcc | gtgcagaagg | aatgataatc | cttttgtata | 5040 |
| cttcttaat | tttattgtaa | aatgtgtaat | gacttttacc | tatatgctgt | gggcaggtcc | 5100 |
| tcagtaaaat | ctattgagtc | aatttctagt | attaacaggc | ttttgcttgc | tatctaagtg | 5160 |
| tttcaaatta | tgggaagtgt | gagacactgg | aaggcaagaa | aattaacaat | aatggcatgt | 5220 |
| gatagcaaaa | ttgtatttca | cttattcctg | tgaatatttc | ttgttggtac | caatggtact | 5280 |
| gtacaaagtg | aatgttatag | ccacaacatt | ctcttgaaaa | gaacactgtc | aagaagtggg | 5340 |
| aaattgctgt | caggcatttc | attgttgttt | ttaaactttt | ttaaaagaaa | tactggtttt | 5400 |
| gcaatataga | gatcatgtgg | taagaatttt | taataagatc | ttatactaaa | aagccttaaa | 5460 |
| tcaatttatt | gagattcaaa | aaatactatt | ataattaatt | acatcccata | catataggca | 5520 |
| aactcattta | aaaataaaa | ctaattttgg | taaaagtaca | tggcctttgt | ttttaaaata | 5580 |
| cataattta | aaataaatca | cttgtcatga | taaagtccaa | aaagaagtta | tcattcaaca | 5640 |
| ttcaactaag | gttggagcta | agaatttact | aatacaaaaa | aagttaaaat | ttttggacc | 5700 |
| atatatatct | tgacagtgta | acttttaagt | aggttcattt | ccatttgcac | agaaagtttc | 5760 |
| tgtctttagg | aaactgaaaa | tgaaatactg | tggatgctat | gactgtttgt | cttgtatgta | 5820 |
| aataggaaat | taataagctg | cctattgagt | ggtatagctg | tatgcttacc | caaaaaggg | 5880 |
| aacactgtgg | ttatgacttg | tattataaac | tttctgtagt | taataaagtt | gttattttta | 5940 |
| taaccatgat | tatattatta | ttattaataa | aatattttat | caaaatgaaa | aaaaaaaaa | 6000 |
| aa | | | | | 6002 |

<210> SEQ ID NO 17
<211> LENGTH: 1369
<212> TYPE: DNA
<213> ORGANISM: homo sapiens

<400> SEQUENCE: 17

| | | | | |
|---|---|---|---|---|
| gaggaaagga | gggggctgga | agagagtaaa | gggctgttgt | taaacagttt | cttaccgtaa | 60 |
| gagggagttc | agacctagat | cttccagtt | aatcacacaa | caaacttagc | tcatcgcaat | 120 |
| aaaagcagc | tcagagccga | ctggctcttt | taggcactga | ctccgaacag | gattctttca | 180 |
| cccaggcatc | tcctccagag | ggatccgcca | gcccgtccag | cagcaccatg | tgggtgacca | 240 |
| aactcctgcc | agccctgctg | ctgcagcatg | tcctcctgca | tctcctcctg | ctccccatcg | 300 |
| ccatcccta | tgcagaggga | caaaggaaaa | gaagaaatac | aattcatgaa | ttcaaaaaat | 360 |
| cagcaaagac | taccctaatc | aaaatagatc | cagcactgaa | gataaaaacc | aaaaaagtga | 420 |
| atactgcaga | ccaatgtgct | aatagatgta | ctaggaataa | aggacttcca | ttcacttgca | 480 |
| aggcttttgt | ttttgataaa | gcaagaaaac | aatgcctctg | gttccccttc | aatagcatgt | 540 |
| caagtggagt | gaaaaagaa | tttggccatg | aatttgacct | ctatgaaaac | aaagactaca | 600 |
| ttagaaactg | catcattggt | aaaggacgca | gctacaaggg | aacagtatct | atcactaaga | 660 |
| gtggcatcaa | atgtcagccc | tggagttcca | tgataccaca | cgaacacagc | ttttttgcctt | 720 |
| cgagctatcg | gggtaaagac | ctacaggaaa | actactgtcg | aaatcctcga | ggggaagaag | 780 |
| ggggaccctg | gtgtttcaca | agcaatccag | aggtacgcta | cgaagtctgt | gacattcctc | 840 |

```
agtgttcaga agttgaatgc atgacctgca atggggagag ttatcgaggt ctcatggatc      900
atacagaatc aggcaagatt tgtcagcgct gggatcatca gacaccacac cggcacaaat      960
tcttgcctga aagatatccc gacaagggct tgatgataa ttattgccgc aatcccgatg      1020
gccagccgag gccatggtgc tatactcttg accctcacac ccgctgggag tactgtgcaa      1080
ttaaaacatg cgagacataa catgggctct caactgatgg tgaacttctt ctggtgagtg      1140
acagaggctg cagtgaagaa taatgagtct aatagaagtt tatcacagat gtctctaatc      1200
tttatagctg atccctacct ctctcgctgt ctttgtaccc agcctgcatt ctgtttcgat      1260
ctgtctttta gcagtccata caatcatttt tctacatgct ggcccttacc tagcttttct      1320
gaatttacaa taaaaactat tttttaacgt gaaaaaaaaa aaaaaaaa                   1369

<210> SEQ ID NO 18
<211> LENGTH: 5987
<212> TYPE: DNA
<213> ORGANISM: homo sapiens

<400> SEQUENCE: 18
gaggaaagga gggggctgga agagagtaaa gggctgttgt taaacagttt cttaccgtaa      60
gagggagttc agacctagat cttttccagtt aatcacacaa caaacttagc tcatcgcaat     120
aaaaagcagc tcagagccga ctggctcttt taggcactga ctccgaacag gattctttca     180
cccaggcatc tcctccagag ggatccgcca gcccgtccag cagcaccatg tgggtgacca     240
aactcctgcc agccctgctg ctgcagcatg tcctcctgca tctcctcctg ctccccatcg     300
ccatccccta tgcagaggga caaggaaaa gaagaaatac aattcatgaa ttcaaaaaat      360
cagcaaagac taccctaatc aaaatagatc cagcactgaa gataaaaacc aaaaaagtga     420
atactgcaga ccaatgtgct aatagatgta ctaggaataa aggacttcca ttcacttgca     480
aggcttttgt ttttgataaa gcaagaaaac aatgcctctg gttccccttc aatagcatgt     540
caagtggagt gaaaaaagaa tttggccatg aatttgacct ctatgaaaac aaagactaca     600
ttagaaactg catcattggt aaaggacgca gctacaaggg aacagtatct atcactaaga     660
gtggcatcaa atgtcagccc tggagttcca tgataccaca cgaacacagc tatcgggta      720
aagacctaca ggaaaactac tgtcgaaatc ctcgagggga agaaggggga ccctggtgtt     780
tcacaagcaa tccagaggta cgctacgaag tctgtgacat tcctcagtgt tcagaagttg     840
aatgcatgac ctgcaatggg agagttatc gaggtctcat ggatcataca gaatcaggca     900
agatttgtca cgctgggat catcagacac acaccggca caattcttg cctgaaagat        960
atcccgacaa gggctttgat gataattatt gccgcaatcc cgatggccag ccgaggccat    1020
ggtgctatac tcttgacccct cacacccgct gggagtactg tgcaattaaa acatgcgctg   1080
acaatactat gaatgacact gatgttcctt tggaaacaac tgaatgcatc caaggtcaag    1140
gagaaggcta caggggcact gtcaatacca tttggaatgg aattccatgt cagcgttggg    1200
attctcagta tcctcacgag catgacatga ctcctgaaaa tttcaagtgc aaggacctac    1260
gagaaaatta ctgccgaaat ccagatgggt ctgaatcacc tggtgttttt accactgatc    1320
caaacatccg agttggctac tgctcccaaa ttccaaactg tgatatgtca catggacaag    1380
attgttatcg tgggaatggc aaaaattata tgggcaactt atcccaaaca agatctggac    1440
taacatgttc aatgtgggac aagaacatgg aagacttaca tcgtcatatc ttctgggaac    1500
cagatgcaag taagctgaat gagaaattact gccgaaatcc agatgatgat gctcatggac    1560
cctggtgcta cacgggaaat ccactcattc cttgggatta ttgccctatt tctcgttgtg    1620
```

```
aaggtgatac cacacctaca atagtcaatt tagaccatcc cgtaatatct tgtgccaaaa   1680
cgaaacaatt gcgagttgta aatgggattc caacacgaac aaacatagga tggatggtta   1740
gtttgagata cagaaataaa catatctgcg gaggatcatt gataaaggag agttgggttc   1800
ttactgcacg acagtgtttc ccttctcgag acttgaaaga ttatgaagct tggcttggaa   1860
ttcatgatgt ccacggaaga ggagatgaga aatgcaaaca ggttctcaat gtttcccagc   1920
tggtatatgg ccctgaagga tcagatctgg ttttaatgaa gcttgccagg cctgctgtcc   1980
tggatgattt tgttagtacg attgatttac ctaattatgg atgcacaatt cctgaaaaga   2040
ccagttgcag tgtttatggc tggggctaca ctggattgat caactatgat ggcctattac   2100
gagtggcaca tctctatata tgggaaatg agaaatgcag ccagcatcat cgagggaagg   2160
tgactctgaa tgagtctgaa atatgtgctg gggctgaaaa gattggatca ggaccatgtg   2220 aggggggatta tggtggccca cttgtttgtg agcaacataa aatgagaatg gttcttggtg   2280
tcattgttcc tggtcgtgga tgtgccattc caaatcgtcc tggtattttt gtccgagtag   2340
catattatgc aaaatggata cacaaaatta ttttaacata taaggtacca cagtcatagc   2400
tgaagtaagt gtgtctgaag cacccaccaa tacaactgtc ttttacatga agatttcaga   2460
gaatgtggaa tttaaaatgt cacttacaac aatcctaaga caactactgg agagtcatgt   2520
ttgttgaaat tctcattaat gtttatgggt gttttctgtt gttttgtttg tcagtgttat   2580
tttgtcaatg ttgaagtgaa ttaaggtaca tgcaagtgta ataacatatc tcctgaagat   2640
acttgaatgg attaaaaaaa cacacaggta tatttgctgg atgataaaga tttcatggga   2700
aaaaaaatca attaatctgt ctaagctgct ttctgatgtt ggtttcttaa taatgagtaa   2760
accacaaatt aaatgttatt ttaacctcac caaaacaatt tataccttgt gtccctaaat   2820
tgtagcccta tattaaatta tattcacttt catatgctat atgttatagt tcattcattt   2880
ctcttcacca tgtatcctgc aatactggta cacgaacaca cttttacaa aaccacatac   2940 ccatgtacac atgcctaggt acacatgtgc atgcactaca gtttaaatta tggtgtacct   3000
aatgtaaccc ctaaatattt tagaagtatg tacctatagt tttacctcaa aaaaaccaga   3060
aatctctaaa gaccagtaga aatattaaaa aatgatgcaa gatcaaaatg attagctaat   3120
tctccataca taatctgcag atgatcttct ttggttggca tttcaggtgt ggccatcacc   3180
cagagttaaa taacacctaa tctaggtgtt tacatgtatt cattatccta gttatttcat   3240
gtagtttcta attcttaaag gaaagagggt aatagttcta tttgtgtaat ttgtttcctc   3300
caaacttaag gccacttatt tacacaagat atttgtagat ctattttcct aaagcatttc   3360
ttaagtgctc agatcagtat ctaattgaag aagtttaaaa gtgttttggt cattaaaaat   3420
gtacttaaat aggttaaatc taagccttgc tgctgtgatt ggcttctagc tcactgcctt   3480 taaatttaa aaaatttaag aggaaaattt ccaagtctcc aaagttttat aaatacccctt   3540 catcaagtca tgcattaaag tatatattgg agaaaaaaat aaaaatactt ttctcaacct   3600
ggaagatttt agcctaataa agctttttg aagtaaaaga caacttgtaa aaggaaagaa   3660
actagtttgt ctcaactctg tattcattta tttttttttt gaagtagagt ggaatctgtt   3720
gaatcagata ttttatcaag atatgtttat tttttcttat ttcatttac aaagttcact   3780 cctaatgcca tatgtaacag acatttaaat tttgtgttct gtataacagc caaattatca   3840
tatttatcat tgtatttgtc atgcttagct aaagatcatg tatttgttga gaaatagaat   3900
aacaaaaagt aataggatag gctttgaatt tttgcagaaa tcttcctgta caaaacaccct   3960
```

```
ttaaaaataa ttttttgaat ggtgtgaatc cagtagtccc atttctctga cttagttttc    4020
ttgagtgatt tttatcaagg ccaagtcccc aaacaattcc ctaccagctc tttagagtac    4080
tgttcaatct ggactaaaat ggttttaagt ttatggagag cttagtccac agaatatagg    4140
gcggcgagtc cagaaatgct tatacaattt ttttttcata ataagatatg tgctggcatc    4200
aagaaactta aagtggaagc aaaaagacat ccaactagtt gctggtctct atcatcttat    4260
ctgatggtat ttctattttc cttatataat acaccatttt agtaagaact cctagaaatt    4320
tcaagagcat attgccaaaa tataaagtat atttcatagt ttcttctggc tgaaccagtg    4380
aaattttatt attgcatatt aatgatattt gtaaaacttt tataaaaatt gtcataattt    4440
taaatactca cattttaaaa atacttcttt aatgactctt cctctaaatt tcctggaaat    4500
acagataaag attagctaga tacaagatac agctaagtat ttagacattt tgaggctagt    4560
attttttcatt ttattaaagg ctaaaaacaa taccaccaat aaatcatcaa acaaaccgta    4620
caaagtaatt ctctctttgg gaggctcctt tcgtgataga gggacatggg tggaattgac    4680
aatgaaactt agatgaacaa ggtccatgtt attttaggtg gtagaacagg gtagagtcat    4740
gtcattattt gctggtggaa gacactattt accaggtgtt cttgctgaa taaatcatta    4800
aacattttta aaaatccaac aatccacttt attttgtgtc attgacaaaa ggatctttta    4860
aatcagaagg tttcaatgca attttttggtt tggctgtttg aataatggtt atgtactgtt    4920
ataattgtag acattttctc acgtctacca ggaattgaag tgtaaaacta aaatattttt    4980
cataatgcct ctgccgtgca gaaggaatga taatcctttt gtatacttct ttaatttttat    5040
tgtaaaatgt gtaatgactt ttacctatat gctgtgggca ggtcctcagt aaaatctatt    5100
gagtcaattt ctagtattaa caggcttttg cttgctatct aagtgtttca aattatggga    5160
agtgtgagac actggaaggc aagaaaatta acaataatgg catgtgatag caaaattgta    5220
tttcacttat tcctgtgaat atttcttgtt ggtaccaatg gtactgtaca aagtgaatgt    5280
tatagccaca acattctctt gaaaagaaca ctgtcaagaa gtgggaaatt gctgtcaggc    5340
atttcattgt tgtttttaaa cttttttaaa agaaatactg gttttgcaat atagagatca    5400
tgtggtaaag aattttaata agatcttata ctaaaaagcc ttaaatcaat ttattgagat    5460
tcaaaaaata ctattataat taattacatc ccatacatat aggcaaactc atttaaaaaa    5520
taaaactaat tttggtaaaa gtacatggcc tttgttttta aaatacataa ttttaaaata    5580
aatcacttgt catgataaag tccaaaaaga agttatcatt caacattcaa ctaaggttgg    5640
agctaagaat ttactaatac aaaaaaagtt aaaattttt ggaccatata tatcttgaca    5700
gtgtaacttt taagtaggtt catttccatt tgcacagaaa gtttctgtct ttaggaaact    5760
gaaaatgaaa tactgtggat gctatgactg tttgtcttgt atgtaaatag gaaattaata    5820
agctgcctat tgagtggtat agctgtatgc ttacccaaaa aagggaacac tgtggttatg    5880
acttgtatta taaactttct gtagttaata aagttgttat ttttataacc atgattatat    5940
tattattatt aataaaatat tttatcaaaa tgaaaaaaaa aaaaaa                   5987
```

<210> SEQ ID NO 19
<211> LENGTH: 1354
<212> TYPE: DNA
<213> ORGANISM: homo sapiens

<400> SEQUENCE: 19

```
gaggaaagga gggggctgga agagagtaaa gggctgttgt taaacagttt cttaccgtaa     60
gagggagttc agacctagat cttttccagtt aatcacacaa caaacttagc tcatcgcaat    120
```

```
aaaaagcagc tcagagccga ctggctcttt taggcactga ctccgaacag gattctttca      180
cccaggcatc tcctccagag ggatccgcca gcccgtccag cagcaccatg tgggtgacca      240
aactcctgcc agccctgctg ctgcagcatg tcctcctgca tctcctcctg ctccccatcg      300
ccatccccta tgcagaggga caaggaaaa gaagaaatac aattcatgaa ttcaaaaaat       360
cagcaaagac taccctaatc aaaatagatc cagcactgaa gataaaaacc aaaaaagtga     420
atactgcaga ccaatgtgct aatagatgta ctaggaataa aggacttcca ttcacttgca      480
aggcttttgt ttttgataaa gcaagaaaac aatgcctctg gttccccttc aatagcatgt     540
caagtggagt gaaaaaagaa tttggccatg aatttgacct ctatgaaaac aaagactaca    600
ttagaaactg catcattggt aaaggacgca gctacaaggg aacagtatct atcactaaga    660
gtggcatcaa atgtcagccc tggagttcca tgataccaca cgaacacagc tatcggggta    720
aagacctaca ggaaaactac tgtcgaaatc ctcgagggga agaaggggga ccctggtgtt    780
tcacaagcaa tccagaggta cgctacgaag tctgtgacat tcctcagtgt tcagaagttg    840
aatgcatgac ctgcaatggg gagagttatc gaggtctcat ggatcataca gaatcaggca     900
agatttgtca gcgctgggat catcagacac acaccggca caaattcttg cctgaaagat      960
atcccgacaa gggctttgat gataattatt gccgcaatcc cgatggccag ccgaggccat    1020
ggtgctatac tcttgacccct cacacccgct gggagtactg tgcaattaaa acatgcgaga   1080
cataacatgg gctctcaact gatggtgaac ttcttctggt gagtgacaga ggctgcagtg    1140
aagaataatg agtctaatag aagtttatca cagatgtctc taatctttat agctgatccc     1200
tacctctctc gctgtctttg tacccagcct gcattctgtt tcgatctgtc ttttagcagt    1260
ccatacaatc atttttctac atgctggccc ttacctagct tttctgaatt tacaataaaa    1320
actatttttt aacgtgaaaa aaaaaaaaaa aaaa                                1354
```

<210> SEQ ID NO 20
<211> LENGTH: 2102
<212> TYPE: DNA
<213> ORGANISM: homo sapiens

<400> SEQUENCE: 20

```
gaggaaagga gggggctgga agagagtaaa gggctgttgt taaacagttt cttaccgtaa      60
gagggagttc agacctagat ctttccagtt aatcacacaa caaacttagc tcatcgcaat    120
aaaaagcagc tcagagccga ctggctcttt taggcactga ctccgaacag gattctttca     180
cccaggcatc tcctccagag ggatccgcca gcccgtccag cagcaccatg tgggtgacca    240
aactcctgcc agccctgctg ctgcagcatg tcctcctgca tctcctcctg ctccccatcg    300
ccatccccta tgcagaggga caaggaaaa gaagaaatac aattcatgaa ttcaaaaaat     360
cagcaaagac taccctaatc aaaatagatc cagcactgaa gataaaaacc aaaaaagtga    420
atactgcaga ccaatgtgct aatagatgta ctaggaataa aggacttcca ttcacttgca    480
aggcttttgt ttttgataaa gcaagaaaac aatgcctctg gttccccttc aatagcatgt    540
caagtggagt gaaaaaagaa tttggccatg aatttgacct ctatgaaaac aaagactaca    600
ttagaaactg catcattggt aaaggacgca gctacaaggg aacagtatct atcactaaga    660
gtggcatcaa atgtcagccc tggagttcca tgataccaca cgaacacagc tttttgcctt    720
cgagctatcg ggtaaagac ctacaggaaa actactgtcg aaatcctcga ggggaagaag    780
ggggaccctg gtgtttcaca agcaatccag aggtacgcta cgaagtctgt gacattcctc     840
```

| | |
|---|---|
| agtgttcaga aggtaaataa acctgaatgc catgtgggcc attctattcc ccctatgtgt | 900 |
| agaactgtaa ctcacattaa aggttaacag caacgaatca atcataacaa atatgttgtt | 960 |
| cgtgcaaatg caactacaaa taattattta aacatttta tacaatgttt ttaaaactgt | 1020 |
| tggattatca ccagattaat gcaaaataac agagcgagtt atcagtttga atttcaacac | 1080 |
| tgcctgagac atccctctgg ggaaagtgaa agagagggtt tacttaccta ctgtcttgag | 1140 |
| ctcacatacc tcaaaatcta ctactgtgtg gcacctgaaa ggagttgaat gaagcttagc | 1200 |
| cttcattag caatgttaat tctattcaac cagcacctgc ttccacagaa attctgtcca | 1260 |
| aactatcatg aagtggtgtg acaagggtat atggacccag aagataatac aatataagaa | 1320 |
| gggatcactg gaagcttgac cccatgcaca ttttggtgaa aatgtgccta gaatcaaatg | 1380 |
| tgacacgtag gctggaactg agtaccattc agaataggat ctgaagagat caaagcaatg | 1440 |
| gagaccacca aactgtcttg aaggcatgtc tatggacctt aagtccatgt ctatgttttc | 1500 |
| agctcttctc acagcataaa agggcattgt ccttactttt gcagtggaaa actgaatggc | 1560 |
| tgacaagatg gaagagtaac catttcagca ttgtatgtgg tttcattttt cttagttatc | 1620 |
| tggctactga atagccggat ttttcagttc tgtcagaaac tctaaatttc caaaatcta | 1680 |
| agtgaaacat ggatgaaact ctgttagaaa attgttagga ttttggagta tttggggagg | 1740 |
| gggactactg gaatgctgtc caagttttat actaagatat cttacctgtt tgttattaac | 1800 |
| caaatatttt taaaaatatt tcctccataa atattcattt aatattaggt tgatatttat | 1860 |
| cacataaaaa gtaaaggcta ctgttagcta attgtcacag agaaggattt gttttctgtt | 1920 |
| gttagtgaat ttgaaatcct tgactttatg tgctacagcc agttccatct ctgtttgtaa | 1980 |
| attcttactt tccattccat atcatattct gttccctata acctcttcat tgttttcttt | 2040 |
| tctttaaaa ataataaact tttctatgat caaaaaaaaa aaaaaaaaa aaaaaaaaa | 2100 |
| aa | 2102 |

<210> SEQ ID NO 21
<211> LENGTH: 2339
<212> TYPE: DNA
<213> ORGANISM: homo sapiens

<400> SEQUENCE: 21

| | |
|---|---|
| acgcggtgcc gcggggcggg agtagaggcg gagggagggg acacgggctc attgcggtgt | 60 |
| gcgccctgca ctctgtccct cactcgccgc cgacgacctg tctcgccgag cgcacgcctt | 120 |
| gccgccgccc cgcagaaatg cttcggttac ccacagtctt tcgccagatg agaccggtgt | 180 |
| ccagggtact ggctcctcat ctcactcggg cttatgccaa agatgtaaaa tttggtgcag | 240 |
| atgcccgagc cttaatgctt caaggtgtag acctttagc cgatgctgtg gccgttacaa | 300 |
| tggggccaaa gggaagaaca gtgattattg agcagagttg gggaagtccc aaagtaacaa | 360 |
| aagatggtgt gactgttgca aagtcaattg acttaaaaga taaatacaaa acattggag | 420 |
| ctaaacttgt tcaagatgtt gccaataaca caaatgaaga agctggggat ggcactacca | 480 |
| ctgctactgt actggcacgc tctatagcca aggaaggctt cgagaagatt agcaaaggtg | 540 |
| ctaatccagt ggaaatcagg agaggtgtga tgttagctgt tgatgctgta attgctgaac | 600 |
| ttaaaaagca gtctaaacct gtgaccaccc ctgaagaaat tgcacaggtt gctacgattt | 660 |
| ctgcaaacgg agacaaagaa attggcaata tcatctctga tgcaatgaaa aaagttggaa | 720 |
| gaaagggtgt catcacagta aaggatggaa aaacactgaa tgatgaatta gaaattattg | 780 |
| aaggcatgaa gtttgatcga ggctatattt ctccatactt tattaataca tcaaaaggtc | 840 |

```
agaaatgtga attccaggat gcctatgttc tgttgagtga aaagaaaatt tctagtatcc      900
agtccattgt acctgctctt gaaattgcca atgctcaccg taagcctttg gtcataatcg      960
ctgaagatgt tgatggagaa gctctaagta cactcgtctt gaataggcta aaggttggtc     1020
ttcaggttgt ggcagtcaag gctccagggt ttggtgacaa tagaaagaac cagcttaaag     1080
atatggctat tgctactggt ggtgcagtgt ttggagaaga gggattgacc ctgaatcttg     1140
aagacgttca gcctcatgac ttaggaaaag ttggagaggt cattgtgacc aaagacgatg     1200
ccatgctctt aaaaggaaaa ggtgacaagg ctcaaattga aaacgtatt caagaaatca      1260
ttgagcagtt agatgtcaca actagtgaat atgaaaagga aaactgaat gaacggcttg      1320
caaaactttc agatggagtg gctgtgctga aggttggtgg gacaagtgat gttgaagtga     1380
atgaaaagaa agacagagtt acagatgccc ttaatgctac aagagctgct gttgaagaag     1440
gcattgtttt gggagggggt tgtgccctcc ttcgatgcat tccagccttg gactcattga     1500
ctccagctaa tgaagatcaa aaaattggta tagaaattat taaagaaca ctcaaaattc      1560
cagcaatgac cattgctaag aatgcaggtg ttgaaggatc tttgatagtt gagaaaatta     1620
tgcaaagttc ctcagaagtt ggttatgatg ctatggctgg agattttgtg aatatggtgg     1680
aaaaaggaat cattgaccca acaaaggttg tgagaactgc tttattggat gctgctggtg     1740
tggcctctct gttaactaca gcagaagttg tagtcacaga aattcctaaa gaagagaagg     1800
accctggaat gggtgcaatg ggtggaatgg gaggtggtat gggaggtggc atgttctaac     1860
tcctagacta gtgctttacc tttattaatg aactgtgaca ggaagcccaa ggcagtgttc     1920
ctcaccaata acttcagaga agtcagttgg agaaaatgaa gaaaaaggct ggctgaaaat     1980
cactataacc atcagttact ggtttcagtt gacaaaatat ataatggttt actgctgtca     2040
ttgtccatgc ctacagataa tttattttgt atttttgaat aaaaaacatt tgtacattcc     2100
tgatactggg tacaagagcc atgtaccagt gtactgcttt caacttaaat cactgaggca     2160
tttttactac tattctgtta aaatcaggat tttagtgctt gccaccacca gatgagaagt     2220
taagcagcct ttctgtggag agtgagaata attgtgtaca agtagagaa gtatccaatt      2280
atgtgacaac ctttgtgtaa taaaaatttg tttaaagtta aaaaaaaaaa aaaaaaaa       2339
```

<210> SEQ ID NO 22
<211> LENGTH: 2319
<212> TYPE: DNA
<213> ORGANISM: homo sapiens

<400> SEQUENCE: 22

```
gccccgacgc gcaccgcgat tcgccccaag ggccctgcgc aggacgctga cgcgaagact       60
cggaggcgga agaaaaaagg agctgttttct aggcttttct aggcgcccag ccgagaaatg     120
cttcggttac ccacagtctt tcgccagatg agaccggtgt ccagggtact ggctcctcat      180
ctcactcggg cttatgccaa agatgtaaaa tttggtgcag atgcccgagc ttaatgctt       240
caaggtgtag acctttagc cgatgctgtg gccgttacaa tggggccaaa gggaagaaca       300
gtgattattg agcagagttg gggaagtccc aaagtaacaa aagatggtgt gactgttgca      360
aagtcaattg acttaaaaga taaatacaaa acattggag ctaaacttgt tcaagatgtt       420
gccaataaca caaatgaaga agctggggat ggcactacca ctgctactgt actggcacgc      480
tctatagcca aggaaggctt cgagaagatt agcaaggtg ctaatccagt ggaaatcagg       540
agaggtgtga tgttagctgt tgatgctgta attgctgaac ttaaaaagca gtctaaacct      600
```

```
gtgaccaccc ctgaagaaat tgcacaggtt gctacgattt ctgcaaacgg agacaaagaa    660
attggcaata tcatctctga tgcaatgaaa aagttggaa gaaagggtgt catcacagta    720
aaggatggaa aaacactgaa tgatgaatta gaaattattg aaggcatgaa gtttgatcga    780
ggctatattt ctccatactt tattaataca tcaaaaggtc agaaatgtga attccaggat    840
gcctatgttc tgttgagtga aagaaaatt tctagtatcc agtccattgt acctgctctt    900
gaaattgcca atgctcaccg taagcctttg tcataatcg ctgaagatgt tgatggagaa    960
gctctaagta cactcgtctt gaataggcta aaggttggtc ttcaggttgt ggcagtcaag   1020
gctccagggt ttggtgacaa tagaaagaac cagcttaaag atatggctat tgctactggt   1080
ggtgcagtgt ttggagaaga gggattgacc ctgaatcttg aagacgttca gcctcatgac   1140
ttaggaaaag ttggagaggt cattgtgacc aaagacgatg ccatgctctt aaaaggaaaa   1200
ggtgacaagg ctcaaattga aaacgtatt caagaaatca ttgagcagtt agatgtcaca   1260
actagtgaat atgaaaagga aaactgaat gaacggcttg caaaactttc agatggagtg   1320
gctgtgctga aggttggtgg acaagtgat gttgaagtga atgaaaagaa agacagagtt   1380
acagatgccc ttaatgctac aagagctgct gttgaagaag gcattgtttt gggaggggt   1440 tgtgccctcc ttcgatgcat tccagccttg gactcattga ctccagctaa tgaagatcaa   1500
aaaattggta tagaaattat taaaagaaca ctcaaaattc cagcaatgac cattgctaag   1560
aatgcaggtg ttgaaggatc tttgatagtt gagaaaatta tgcaaagttc ctcagaagtt   1620
ggttatgatg ctatggctgg agattttgtg aatatggtgg aaaaaggaat cattgaccca   1680
acaaaggttg tgagaactgc tttattggat gctgctggtg tggcctctct gttaactaca   1740
gcagaagttg tagtcacaga aattcctaaa gaagagaagg accctggaat gggtgcaatg   1800
ggtggaatgg gaggtggtat gggaggtggc atgttctaac tcctagacta gtgctttacc   1860
tttattaatg aactgtgaca ggaagcccaa ggcagtgttc ctcaccaata acttcagaga   1920
agtcagttgg agaaaatgaa gaaaaaggct ggctgaaaat cactataacc atcagttact   1980
ggtttcagtt gacaaaatat ataatggttt actgctgtca ttgtccatgc ctacagataa   2040
tttattttgt atttttgaat aaaaaacatt tgtacattcc tgatactggg tacaagagcc   2100
atgtaccagt gtactgcttt caacttaaat cactgaggca tttttactac tattctgtta   2160
aaatcaggat tttagtgctt gccaccacca gatgagaagt taagcagcct ttctgtggag   2220
agtgagaata attgtgtaca agtagagaa gtatccaatt atgtgacaac ctttgtgtaa   2280
taaaaatttg tttaaagtta aaaaaaaaaa aaaaaaaaa                         2319
```

<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 23
tctgtttccc gtgctgcgag                                                20

<210> SEQ ID NO 24
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 24

```
cccagcgtcc agtagcacac                                                   20

<210> SEQ ID NO 25
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 25
cctacaattc ttctttgggc t                                                 21

<210> SEQ ID NO 26
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 26
agtaacagtt atggcttgga                                                   20

<210> SEQ ID NO 27
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 27
ggaatgctgc catggagatc tgc                                               23

<210> SEQ ID NO 28
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 28
ccttcagttt actggagatc g                                                 21

<210> SEQ ID NO 29
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 29
ctccaaaggc cagcctgact                                                   20

<210> SEQ ID NO 30
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 30
cagcccaccc aaaccaccaa                                                   20

<210> SEQ ID NO 31
<211> LENGTH: 19
<212> TYPE: DNA
```

```
<213> ORGANISM: Artificial sequence
<220> FEATURE:
<223> OTHER INFORMATION: Single strand DNA oligonucleotide

<400> SEQUENCE: 31
gcctcgtatg tgaggcaaa                                                19

<210> SEQ ID NO 32
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 32
cccattcgta gcctttggta                                               20

<210> SEQ ID NO 33
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 33
aaagtacgtc cgcgggttgc                                               20

<210> SEQ ID NO 34
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 34
tccgatgagt ccggccagt                                                19

<210> SEQ ID NO 35
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 35
gggagcggtg aagatgga                                                 18

<210> SEQ ID NO 36
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 36
tcatgttgct cacggaggag ta                                            22

<210> SEQ ID NO 37
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 37
gccgagtttg ccttgctca                                                19
```

-continued

<210> SEQ ID NO 38
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 38
tccggaggct caccagtttc                                                      20

<210> SEQ ID NO 39
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 39
aaggtgaagc gcaatgtccc t                                                    21

<210> SEQ ID NO 40
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 40
cccccagctg ctcaaaaatg c                                                    21

<210> SEQ ID NO 41
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 41
tgctctgtgt cactgtggat tgg                                                  23

<210> SEQ ID NO 42
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 42
gggcaaagag gctggtcttc a                                                    21

<210> SEQ ID NO 43
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 43
ctcacctcca ggtttgcttc                                                      20

<210> SEQ ID NO 44
<211> LENGTH: 20
<212> TYPE: DNA
<213> ORGANISM: Artificial sequence
<220> FEATURE:

<223> OTHER INFORMATION: Single strand DNA oligonucleotide

<400> SEQUENCE: 44
ctccttgatc gatcctttgc                                               20

<210> SEQ ID NO 45
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 45
tctccaggtt gcctctcact                                               20

<210> SEQ ID NO 46
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 46
gtggaggaag ctgacaacaa                                               20

<210> SEQ ID NO 47
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 47
tcgagccaat actgcatctg                                               20

<210> SEQ ID NO 48
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 48
cttctgggag gacatccttg                                               20

<210> SEQ ID NO 49
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 49
acgagacaga agacggcatt                                               20

<210> SEQ ID NO 50
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 50
ccctctggat ccactgctt                                                19

```
<210> SEQ ID NO 51
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 51
ccccacattc gtcagcggtg t                                              21

<210> SEQ ID NO 52
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 52
aggtgcccga gggttctgag g                                              21

<210> SEQ ID NO 53
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 53
ggcgcagcag aatccaga                                                  18

<210> SEQ ID NO 54
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 54
ccacgacttg cccagcat                                                  18

<210> SEQ ID NO 55
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 55
gcttagcctc gtcgatgaac                                                20

<210> SEQ ID NO 56
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 56
aaccccaaga tgcacaactc                                                20

<210> SEQ ID NO 57
<211> LENGTH: 20
<212> TYPE: DNA
<213> ORGANISM: Artificial sequence
<220> FEATURE:
<223> OTHER INFORMATION: Single strand DNA oligonucleotide
```

```
<400> SEQUENCE: 57
cgggtgtggc acagctagtt                                              20

<210> SEQ ID NO 58
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 58
tgcattgtca agtgacgatc ac                                           22

<210> SEQ ID NO 59
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 59
aaagtacgtc cgcgggttgc                                              20

<210> SEQ ID NO 60
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 60
tccgatgagt ccggccagt                                               19

<210> SEQ ID NO 61
<211> LENGTH: 15
<212> TYPE: DNA
<213> ORGANISM: Artificial sequence
<220> FEATURE:
<223> OTHER INFORMATION: PXR response element

<400> SEQUENCE: 61
tgaacttgct gaccc                                                   15

<210> SEQ ID NO 62
<211> LENGTH: 21
<212> TYPE: DNA
<213> ORGANISM: Artificial sequence
<220> FEATURE:
<223> OTHER INFORMATION: LXR response elements

<400> SEQUENCE: 62
gggttactgg cggtcattgt a                                            21

<210> SEQ ID NO 63
<211> LENGTH: 19
<212> TYPE: DNA
<213> ORGANISM: Artificial sequence
<220> FEATURE:
<223> OTHER INFORMATION: PPAR response element

<400> SEQUENCE: 63
tacctttccc ctacttttc                                               19

<210> SEQ ID NO 64
<211> LENGTH: 14
```

```
<212> TYPE: DNA
<213> ORGANISM: Artificial sequence
<220> FEATURE:
<223> OTHER INFORMATION: BSEP promoter element

<400> SEQUENCE: 64
gggacattga tcct                                                       14

<210> SEQ ID NO 65
<211> LENGTH: 110
<212> TYPE: PRT
<213> ORGANISM: homo sapiens

<400> SEQUENCE: 65
```

Met Ala Leu Trp Met Arg Leu Leu Pro Leu Leu Ala Leu Leu Ala Leu
1               5                   10                  15

Trp Gly Pro Asp Pro Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

```
<210> SEQ ID NO 66
<211> LENGTH: 469
<212> TYPE: DNA
<213> ORGANISM: homo sapiens

<400> SEQUENCE: 66
agccctccag gacaggctgc atcagaagag gccatcaagc agatcactgt ccttctgcca     60
tggccctgtg gatgcgcctc ctgccctgc tggcgctgct ggccctctgg ggacctgacc    120
cagccgcagc ctttgtgaac caacacctgt gcggctcaca cctggtggaa gctctctacc    180
tagtgtgcgg ggaacgaggc ttcttctaca cacccaagac ccgccgggag cagaggacc     240 tgcaggtggg gcaggtggag ctgggcgggg gccctggtgc aggcagcctg cagcccttgg    300
ccctggaggg gtccctgcag aagcgtggca ttgtggaaca atgctgtacc agcatctgct    360
ccctctacca gctggagaac tactgcaact agacgcagcc cgcaggcagc cccacacccg    420
ccgcctcctg caccgagaga gatggaataa agcccttgaa ccagcaaaa               469

<210> SEQ ID NO 67
<211> LENGTH: 288
<212> TYPE: PRT
<213> ORGANISM: homo sapiens

<400> SEQUENCE: 67
```

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
        50                  55                  60
Thr Arg Gly Arg Arg Thr Glu Glu Arg Pro Ser Gly Ser Arg Leu Gly
 65                  70                  75                  80
Asp Arg Gly Arg Gly Arg Ala Leu Pro Gly Gly Arg Leu Gly Gly Arg
                 85                  90                  95
Gly Arg Gly Arg Ala Pro Glu Arg Val Gly Arg Gly Arg Gly Arg
            100                 105                 110
Gly Thr Ala Ala Pro Arg Ala Ala Pro Ala Ala Arg Gly Ser Arg Pro
            115                 120                 125
Gly Pro Ala Gly Thr Met Ala Ala Gly Ser Ile Thr Thr Leu Pro Ala
130                 135                 140
Leu Pro Glu Asp Gly Gly Ser Gly Ala Phe Pro Pro Gly His Phe Lys
145                 150                 155                 160
Asp Pro Lys Arg Leu Tyr Cys Lys Asn Gly Gly Phe Phe Leu Arg Ile
                165                 170                 175
His Pro Asp Gly Arg Val Asp Gly Val Arg Glu Lys Ser Asp Pro His
            180                 185                 190
Ile Lys Leu Gln Leu Gln Ala Glu Glu Arg Gly Val Val Ser Ile Lys
            195                 200                 205
Gly Val Cys Ala Asn Arg Tyr Leu Ala Met Lys Glu Asp Gly Arg Leu
210                 215                 220
Leu Ala Ser Lys Cys Val Thr Asp Glu Cys Phe Phe Phe Glu Arg Leu
225                 230                 235                 240
Glu Ser Asn Asn Tyr Asn Thr Tyr Arg Ser Arg Lys Tyr Thr Ser Trp
                245                 250                 255
Tyr Val Ala Leu Lys Arg Thr Gly Gln Tyr Lys Leu Gly Ser Lys Thr
            260                 265                 270
Gly Pro Gly Gln Lys Ala Ile Leu Phe Leu Pro Met Ser Ala Lys Ser
            275                 280                 285

<210> SEQ ID NO 68
<211> LENGTH: 6774
<212> TYPE: DNA
<213> ORGANISM: homo sapiens

<400> SEQUENCE: 68
cggccccaga aaacccgagc gagtaggggg cggcgcgcag gagggaggag aactgggggc      60
gcgggaggct ggtgggtgtg gggggtggag atgtagaaga tgtgacgccg cggcccggcg     120
ggtgccagat tagcggacgc ggtgcccgcg gttgcaacgg gatcccgggc gctgcagctt     180
gggaggcggc tctccccagg cggcgtccgc ggagacaccc atccgtgaac cccaggtccc     240
gggccgccgg ctcgccgcgc accaggggcc ggcggacaga gagcggccg agcggctcga      300 ggctggggga ccgcgggcgc ggccgcgcgc tgccgggcgg gaggctgggg ggccggggcc     360
ggggccgtgc cccggagcgg gtcggaggcc ggggccgggg ccggggacg gcggctcccc      420 gcgcggctcc agcggctcgg ggatcccggc cgggccccgc aggaccatg gcagccggga     480 gcatcaccac gctgcccgcc ttgcccgagg atggcggcag cggcgccttc ccgcccggcc     540
acttcaagga ccccaagcgg ctgtactgca aaaacggggg cttcttcctg cgcatccacc     600
ccgacggccg agttgacggg gtccgggaga agagcgaccc tcacatcaag ctacaacttc     660
aagcagaaga gagaggagtt gtgtctatca aggagtgtg tgctaaccgt tacctggcta     720
tgaaggaaga tggaagatta ctggcttcta aatgtgttac ggatgagtgt ttcttttttg     780

```
aacgattgga atctaataac tacaatactt accggtcaag gaaatacacc agttggtatg    840
tggcactgaa acgaactggg cagtataaac ttggatccaa aacaggacct gggcagaaag    900
ctatacttt tcttccaatg tctgctaaga gctgatttta atggccacat ctaatctcat    960
ttcacatgaa agaagaagta tatttttagaa atttgttaat gagagtaaaa gaaaataaat   1020
gtgtatagct cagtttggat aattggtcaa acaattttt atccagtagt aaaatatgta    1080
accattgtcc cagtaaagaa aaataacaaa agttgtaaaa tgtatattct ccctttata   1140
ttgcatctgc tgttacccag tgaagcttac ctagagcaat gatcttttc acgcatttgc   1200
tttattcgaa aagaggcttt taaaatgtgc atgtttagaa acaaaatttc ttcatggaaa   1260
tcatatacat tagaaaatca cagtcagatg tttaatcaat ccaaaatgtc cactatttct   1320
tatgtcattc gttagtctac atgtttctaa acatataaat gtgaatttaa tcaattcctt   1380
tcatagtttt ataattctct ggcagttcct tatgatagag tttataaaac agtcctgtgt   1440
aaactgctgg aagttcttcc acagtcaggt caattttgtc aaacccttct ctgtacccat   1500
acagcagcag cctagcaact ctgctggtga tgggagttgt attttcagtc ttcgccaggt   1560
cattgagatc catccactca catcttaagc attcttcctg gcaaaattt atggtgaatg   1620
aatatggctt taggcggcag atgatataca tatctgactt cccaaaagct ccaggatttg   1680
tgtgctgttg ccgaatactc aggacggacc tgaattctga ttttatacca gtctcttcaa   1740
aaacttctcg aaccgctgtg tctcctacgt aaaaaaagag atgtacaaat caataataat   1800
tacacttta gaaactgtat catcaaagat tttcagttaa agtagcatta tgtaaaggct   1860
caaaacatta ccctaacaaa gtaaagtttt caatacaaat tctttgcctt gtggatatca   1920
agaaatccca aaatatttc ttaccactgt aaattcaaga agcttttgaa atgctgaata   1980
tttctttggc tgctacttgg aggcttatct acctgtacat ttttggggtc agctcttttt   2040
aacttcttgc tgctctttt cccaaaaggt aaaaatatag attgaaaagt taaaacattt   2100
tgcatggctg cagttccttt gtttcttgag ataagattcc aaagaactta gattcatttc   2160
ttcaacaccg aaatgctgga ggtgtttgat cagttttcaa gaaacttgga atataaataa   2220
ttttataatt caacaaaggt tttcacattt tataaggttg attttcaat taaatgcaaa   2280
tttgtgtggc aggatttta ttgccattaa catattttg tggctgcttt tctacacat    2340
ccagatggtc cctctaactg gctttctct aattttgtga tgttctgtca ttgtctccca   2400
aagtatttag gagaagccct ttaaaaagct gccttcctct accactttgc tggaaagctt   2460
cacaattgtc acagacaaag attttgttc caatactcgt tttgcctcta ttttcttgt    2520
ttgtcaaata gtaaatgata tttgcccttg cagtaattct actggtgaaa acatgcaaa   2580
gaagaggaag tcacagaaac atgtctcaat tcccatgtgc tgtgactgta gactgtctta   2640
ccatagactg tcttacccat cccctggata tgctcttgtt ttttccctct aatagctatg   2700
gaaagatgca tagaaagagt ataatgtttt aaaacataag gcattcgtct gccatttttc   2760
aattacatgc tgacttccct tacaattgag atttgcccat aggttaaaca tggttagaaa   2820
caactgaaag cataaagaa aaatctaggc cgggtgcagt ggctcatgcc tatattccct   2880
gcactttggg aggccaaagc aggaggatcg cttgagccca ggagttcaag accaacctgg   2940
tgaaaccccg tctctacaaa aaaacacaaa aaatagccag gcatggtggc gtgtacatgt   3000
ggtctcagat acttgggagg ctgaggtggg agggttgatc acttgaggct gagaggtcaa   3060
ggttgcagtg agccataatc gtgccactgc agtccagcct aggcaacaga gtgagacttt   3120
gtctcaaaaa aagagaaatt ttccttaata agaaaagtaa tttttactct gatgtgcaat   3180
```

```
acatttgtta ttaaatttat tatttaagat ggtagcacta gtcttaaatt gtataaaata    3240 tccccctaaca tgtttaaatg tccattttta ttcattatgc tttgaaaaat aattatgggg   3300
aaatacatgt tgttattaa atttattatt aaagatagta gcactagtct taaatttgat    3360
ataacatctc ctaacttgtt taaatgtcca tttttattct ttatgtttga aaataaatta   3420
tggggatcct atttagctct tagtaccact aatcaaaagt tcggcatgta gctcatgatc   3480
tatgctgttt ctatgtcgtg gaagcaccgg atggggtag tgagcaaatc tgccctgctc    3540
agcagtcacc atagcagctg actgaaaatc agcactgcct gagtagtttt gatcagttta   3600
acttgaatca ctaactgact gaaaattgaa tgggcaaata agtgcttttg tctccagagt   3660
atgcgggaga cccttccacc tcaagatgga tatttcttcc ccaaggattt caagatgaat   3720 tgaaatttt aatcaagata gtgtgcttta ttctgttgta ttttttatta ttttaatata    3780
ctgtaagcca aactgaaata acatttgctg ttttataggt ttgaagaaca taggaaaaac   3840
taagaggttt tgttttatt tttgctgatg aagagatatg tttaaatatg ttgtattgtt    3900
ttgtttagtt acaggacaat aatgaaatgg agtttatatt tgttatttct attttgttat   3960
atttaataat agaattagat tgaaataaaa tataatggga aataatctgc agaatgtggg   4020
ttttcctggt gtttccctct gactctagtg cactgatgat ctctgataag gctcagctgc   4080
tttatagttc tctggctaat gcagcagata ctcttcctgc cagtggtaat acgattttt   4140 aagaaggcag tttgtcaatt ttaatcttgt ggatacctt atactcttag ggtattattt    4200
tatacaaaag ccttgaggat tgcattctat tttctatatg accctcttga tatttaaaaa   4260
acactatgga taacaattct tcatttacct agtattatga agaatgaag gagttcaaac    4320 aaatgtgttt cccagttaac tagggtttac tgtttgagcc aatataaatg tttaactgtt   4380
tgtgatggca gtattcctaa agtacattgc atgttttcct aaatacagag tttaaataat   4440
ttcagtaatt cttagatgat tcagcttcat cattaagaat atcttttgtt ttatgttgag   4500
ttagaaatgc cttcatatag acatagtctt tcagacctct actgtcagtt tcatttcta    4560 gctgctttca gggttttatg aattttcagg caaagcttta atttatacta agcttaggaa   4620
gtatggctaa tgccaacggc agtttttttc ttcttaattc cacatgactg aggcatatat   4680
gatctctggg taggtgagtt gttgtgacaa ccacaagcac ttttttttt tttaagaaa    4740 aaaaggtagt gaatttttaa tcatctggac tttaagaagg attctggagt atacttaggc   4800
ctgaaattat atatatttgg cttggaaatg tgttttcctt caattacatc tacaagtaag   4860
tacagctgaa attcagagga cccataagag ttcacatgaa aaaatcaat ttatttgaaa    4920 aggcaagatg caggagagag gaagccttgc aaacctgcag actgcttttt gcccaatata   4980
gattgggtaa ggctgcaaaa cataagctta attagctcac atgctctgct ctcacgtggc   5040
accagtggat agtgtgagag aattaggctg tagaacaaat ggccttctct ttcagcattc   5100
acaccactac aaaatcatct tttatatcaa cagaagaata agcataaaact aagcaaaagg   5160 tcaataagta cctgaaacca agattggcta gagatatatc ttaatgcaat ccatttctg    5220 atggattgtt acgagttggc tatataatgt atgtatggta ttttgatttg tgtaaaagtt   5280
ttaaaaatca agctttaagt acatggacat ttttaaataa aatatttaaa gacaatttag   5340
aaaattgcct taatatcatt gttggctaaa tagaataggg gacatgcata ttaaggaaaa   5400
ggtcatggag aaataatatt ggtatcaaac aaatacattg atttgtcatg atacacattg   5460
aatttgatcc aatagtttaa ggaataggta ggaaaatttg gtttctatt ttcgatttcc     5520
```

-continued

```
tgtaaatcag tgacataaat aattcttagc ttatttata tttccttgtc ttaaatactg    5580
agctcagtaa gttgtgttag gggattattt ctcagttgag actttcttat atgacatttt    5640
actatgtttt gacttcctga ctattaaaaa taaatagtag atacaatttt cataaagtga    5700
agaattatat aatcactgct ttataactga ctttattata tttatttcaa agttcattta    5760
aaggctacta ttcatcctct gtgatggaat ggtcaggaat ttgttttctc atagtttaat    5820
tccaacaaca atattagtcg tatccaaaat aaccttaat gctaaacttt actgatgtat    5880
atccaaagct tctcatttc agacagatta atccagaagc agtcataaac agaagaatag    5940
gtggtatgtt cctaatgata ttatttctac taatggaata aactgtaata ttagaaatta    6000
tgctgctaat tatatcagct ctgaggtaat ttctgaaatg ttcagactca gtcggaacaa    6060
attggaaaat ttaatttttt attcttagct ataaagcaag aaagtaaaca cattaatttc    6120
ctcaacattt ttaagccaat taaaaatata aagatacac accaatatct tcttcaggct    6180
ctgacaggcc tcctggaaac ttccacatat ttttcaactg cagtataaag tcagaaaata    6240
aagttaacat aactttcact aacacacaca tatgtagatt tcacaaaatc cacctataat    6300
tggtcaaagt ggttgagaat atattttta gtaattgcat gcaaaatttt tctagcttcc    6360
atcctttctc cctcgtttct tctttttttg ggggagctgg taactgatga aatcttttcc    6420 cacctttct cttcaggaaa tataagtggt tttgtttggt taacgtgata cattctgtat    6480
gaatgaaaca ttggagggaa acatctactg aatttctgta atttaaaata ttttgctgct    6540
agttaactat gaacagatag aagaatctta cagatgctgc tataaataag tagaaaatat    6600
aaatttcatc actaaaatat gctatttaa aatctatttc ctatattgta tttctaatca    6660
gatgtattac tcttattatt tctattgtat gtgttaatga ttttatgtaa aaatgtaatt    6720
gcttttcatg agtagtatga ataaaattga ttagtttgtg ttttcttgtc tccc          6774
```

<210> SEQ ID NO 69
<211> LENGTH: 40
<212> TYPE: PRT
<213> ORGANISM: homo sapiens

<400> SEQUENCE: 69

Gly Pro Gly Ala Gly Ser Leu Gln Pro Leu Ala Leu Glu Gly Ser Leu
1               5                   10                  15

Gln Lys Arg Gly Ile Val Glu Gln Cys Cys Thr Ser Ile Cys Ser Leu
            20                  25                  30

Tyr Gln Leu Glu Asn Tyr Cys Asn
        35                  40

<210> SEQ ID NO 70
<211> LENGTH: 6774
<212> TYPE: DNA
<213> ORGANISM: homo sapiens

<400> SEQUENCE: 70

```
cggccccaga aaccccgagc gagtaggggg cggcgcgcag gagggaggag aactgggggc      60
gcgggaggct ggtgggtgtg gggggtggag atgtagaaga tgtgacgccg cggcccggcg     120
ggtgccagat tagcggacgc ggtgcccgcg gttgcaacgg gatcccgggc gctgcagctt     180
gggaggcggc tctccccagg cggcgtccgc ggagacaccc atccgtgaac cccaggtccc     240
gggccgccgg ctcgccgcgc accagggcc ggcggacaga gagcggccg agcggctcga     300 ggctggggga ccgcgggcgc ggccgcgcgc tgccgggcgg gaggctgggg ggccggggcc     360
```

```
ggggccgtgc cccggagcgg gtcggaggcc ggggccgggg ccggggacg gcggctcccc      420
gcgcggctcc agcggctcgg ggatcccggc cgggccccgc agggaccatg gcagccggga      480
gcatcaccac gctgcccgcc ttgcccgagg atggcggcag cggcgccttc ccgcccggcc      540
acttcaagga ccccaagcgg ctgtactgca aaaacggggg cttcttcctg cgcatccacc      600
ccgacggccg agttgacggg gtccgggaga agagcgaccc tcacatcaag ctacaacttc      660
aagcagaaga gagaggagtt gtgtctatca aggagtgtg tgctaaccgt tacctggcta       720
tgaaggaaga tggaagatta ctggcttcta aatgtgttac ggatgagtgt ttcttttttg      780
aacgattgga atctaataac tacaatactt accggtcaag gaaatacacc agttggtatg      840
tggcactgaa acgaactggg cagtataaac ttggatccaa acaggacct gggcagaaag        900
ctatactttt tcttccaatg tctgctaaga gctgatttta atggccacat ctaatctcat      960
ttcacatgaa agaagaagta tattttagaa atttgttaat gagagtaaaa gaaataaat      1020
gtgtatagct cagtttggat aattggtcaa acaattttt atccagtagt aaatatgta       1080
accattgtcc cagtaaagaa aataacaaa agttgtaaaa tgtatattct ccctttata       1140
ttgcatctgc tgttacccag tgaagcttac ctagagcaat gatctttttc acgcatttgc     1200
tttattcgaa aagaggcttt taaatgtgc atgtttagaa acaaaatttc ttcatggaaa      1260
tcatatacat tagaaaatca cagtcagatg tttaatcaat ccaaaatgtc cactatttct      1320
tatgtcattc gttagtctac atgtttctaa acatataaat gtgaatttaa tcaattcctt     1380
tcatagtttt ataattctct ggcagttcct tatgatagag tttataaaac agtcctgtgt    1440
aaactgctgg aagttcttcc acagtcaggt caattttgtc aaacccttct ctgtacccat     1500
acagcagcag cctagcaact ctgctggtga tgggagttgt attttcagtc ttcgccaggt     1560
cattgagatc catccactca catcttaagc attcttcctg gcaaaattt atggtgaatg     1620
aatatggctt taggcggcag atgatataca tatctgactt cccaaaagct ccaggatttg     1680
tgtgctgttg ccgaatactc aggacggacc tgaattctga ttttatacca gtctcttcaa     1740
aaacttctcg aaccgctgtg tctcctacgt aaaaaaagag atgtacaaat caataataat     1800
tacactttta gaaactgtat catcaaagat tttcagttaa agtagcatta tgtaaaggct     1860
caaaacatta ccctaacaaa gtaaagtttt caatacaaat tctttgcctt gtggatatca     1920
agaaatccca aaatattttc ttaccactgt aaattcaaga agcttttgaa atgctgaata     1980
tttctttggc tgctacttgg aggcttatct acctgtacat ttttggggtc agctctttt     2040
aacttcttgc tgctctttt cccaaaaggt aaaaatatag attgaaaagt taaaacatt      2100
tgcatggctg cagttccttt gtttcttgag ataagattcc aaagaactta gattcatttc     2160
ttcaacaccg aaatgctgga ggtgtttgat cagttttcaa gaaacttgga atataaataa     2220
ttttataatt caacaaaggt tttcacattt tataaggttg attttcaat taaatgcaaa      2280
tttgtgtggc aggattttta ttgccattaa catattttg tggctgcttt ttctacacat      2340
ccagatggtc cctctaactg ggctttctct aattttgtga tgttctgtca ttgtctccca     2400
aagtatttag gagaagccct ttaaaaagct gccttcctct accactttgc tggaaagctt     2460
cacaattgtc acagacaaag atttttgttc caatactcgt tttgcctcta ttttctgt       2520
ttgtcaaata gtaaatgata tttgcccttg cagtaattct actggtgaaa acatgcaaa      2580
gaagaggaag tcacagaaac atgtctcaat tcccatgtgc tgtgactgta gactgtctta     2640
ccatagactc tcttacccat cccctggata tgctcttgtt ttttccctct aatagctatg     2700
gaaagatgca tagaaagagt ataatgtttt aaaacataag gcattcgtct gccattttc     2760
```

```
aattacatgc tgacttccct tacaattgag atttgcccat aggttaaaca tggttagaaa    2820
caactgaaag cataaaagaa aaatctaggc cgggtgcagt ggctcatgcc tatattccct    2880
gcactttggg aggccaaagc aggaggatcg cttgagccca ggagttcaag accaacctgg    2940
tgaaaccccg tctctacaaa aaaacacaaa aaatagccag gcatggtggc gtgtacatgt    3000
ggtctcagat acttgggagg ctgaggtggg agggttgatc acttgaggct gagaggtcaa    3060
ggttgcagtg agccataatc gtgccactgc agtccagcct aggcaacaga gtgagacttt    3120
gtctcaaaaa aagagaaatt ttccttaata agaaagtaa ttttactct gatgtgcaat    3180 acatttgtta ttaaatttat tatttaagat ggtagcacta gtcttaaatt gtataaaata    3240
tcccctaaca tgtttaaatg tccattttta ttcattatgc tttgaaaaat aattatgggg    3300
aaatacatgt ttgttattaa atttattatt aaagatagta gcactagtct taaatttgat    3360
ataacatctc ctaacttgtt taaatgtcca tttttattct ttatgtttga aaataaatta    3420
tggggatcct atttagctct tagtaccact aatcaaaagt tcggcatgta gctcatgatc    3480
tatgctgttt ctatgtcgtg aagcaccgg atggggtag tgagcaaatc tgccctgctc    3540
agcagtcacc atagcagctg actgaaaatc agcactgcct gagtagtttt gatcagttta    3600
acttgaatca ctaactgact gaaaattgaa tgggcaaata agtgcttttg tctccagagt    3660
atgcgggaga cccttccacc tcaagatgga tatttcttcc ccaaggattt caagatgaat    3720 tgaattttt aatcaagata gtgtgcttta ttctgttgta ttttttatta ttttaatata    3780
ctgtaagcca aactgaaata acatttgctg ttttataggt ttgaagaaca taggaaaaac    3840
taagaggttt tgtttttatt tttgctgatg aagagatatg tttaaatatg ttgtattgtt    3900
ttgtttagtt acaggacaat aatgaaatgg agtttatatt tgttatttct attttgttat    3960
atttaataat agaattagat tgaaataaaa tataatggga aataatctgc agaatgtggg    4020
ttttcctggt gtttccctct gactctagtg cactgatgat ctctgataag gctcagctgc    4080
tttatagttc tctggctaat gcagcagata ctcttcctgc cagtggtaat acgattttt    4140 aagaaggcag tttgtcaatt ttaatcttgt ggatacctt atactcttag ggtattattt    4200
tatacaaaag ccttgaggat tgcattctat tttctatatg accctcttga tatttaaaaa    4260
acactatgga taacaattct tcatttacct agtattatga agaatgaag gagttcaaac    4320 aaatgtgttt cccagttaac tagggttac tgtttgagcc aatataaatg tttaactgtt    4380
tgtgatggca gtattcctaa agtacattgc atgttttcct aaatacagag tttaaataat    4440
ttcagtaatt cttagatgat tcagcttcat cattaagaat atcttttgtt ttatgttgag    4500
ttagaaatgc cttcatatag acatagtctt tcagacctct actgtcagtt ttcatttcta    4560
gctgctttca gggttttatg aattttcagg caaagcttta atttatacta agcttaggaa    4620
gtatggctaa tgccaacggc agttttttc ttcttaattc cacatgactg aggcatatat    4680
gatctctggg taggtgagtt gttgtgacaa ccacaagcac tttttttttt tttaaagaaa    4740
aaaaggtagt gaattttaa tcatctggac tttaagaagg attctggagt atacttaggc    4800
ctgaaattat atatatttgg cttggaaatg tgtttttctt caattacatc tacaagtaag    4860
tacagctgaa attcagagga cccataagag ttccatgaa aaaatcaat ttatttgaaa    4920 aggcaagatg caggagagag gaagccttgc aaacctgcag actgcttttt gcccaatata    4980
gattgggtaa ggctgcaaaa cataagctta attagctcac atgctctgct ctcacgtggc    5040
accagtggat agtgtgagag aattaggctg tagaacaaat ggccttctct ttcagcattc    5100
```

-continued

```
acaccactac aaaatcatct tttatatcaa cagaagaata agcataaact aagcaaaagg      5160
tcaataagta cctgaaacca agattggcta gagatatatc ttaatgcaat ccattttctg      5220
atggattgtt acgagttggc tatataatgt atgtatggta ttttgatttg tgtaaaagtt      5280
ttaaaaatca agctttaagt acatggacat ttttaaataa aatatttaaa gacaatttag      5340
aaaattgcct taatatcatt gttggctaaa tagaataggg gacatgcata ttaaggaaaa      5400
ggtcatggag aaataatatt ggtatcaaac aaatacattg atttgtcatg atacacattg      5460
aatttgatcc aatagtttaa ggaataggta ggaaaatttg gtttctattt tcgatttcc       5520 tgtaaatcag tgacataaat aattcttagc ttattttata tttccttgtc ttaaatactg      5580
agctcagtaa gttgtgttag gggattattt ctcagttgag actttcttat atgacatttt      5640
actatgtttt gacttcctga ctattaaaaa taaatagtag atacaatttt cataaagtga      5700
agaattatat aatcactgct ttataactga ctttattata tttatttcaa agttcattta      5760
aaggctacta ttcatcctct gtgatggaat ggtcaggaat tgttttctc atagtttaat       5820 tccaacaaca atattagtcg tatccaaaat aacctttaat gctaaacttt actgatgtat      5880
atccaaagct tctcattttc agacagatta atccagaagc agtcataaac agaagaatag      5940
gtggtatgtt cctaatgata ttatttctac taatggaata aactgtaata ttagaaatta      6000
tgctgctaat tatatcagct ctgaggtaat ttctgaaatg ttcagactca gtcggaacaa      6060
attggaaaat ttaattttt attcttagct ataaagcaag aaagtaaaca cattaatttc       6120
ctcaacattt ttaagccaat taaaaatata aagatacac accaatatct tcttcaggct       6180
ctgacaggcc tcctggaaac ttccacatat ttttcaactg cagtataaag tcagaaaata      6240
aagttaacat aactttcact aacacacaca tatgtagatt tcacaaaatc cacctataat      6300
tggtcaaagt ggttgagaat atatttttta gtaattgcat gcaaaatttt tctagcttcc      6360
atcctttctc cctcgtttct tcttttttg ggggagctgg taactgatga aatcttttcc       6420 cacctttct cttcaggaaa tataagtggt tttgttggt taacgtgata cattctgtat        6480
gaatgaaaca ttggagggaa acatctactg aatttctgta atttaaaata ttttgctgct      6540
agttaactat gaacagatag aagaatctta cagatgctgc tataaataag tagaaaatat      6600
aaatttcatc actaaaatat gctattttaa aatctatttc ctatattgta tttctaatca      6660
gatgtattac tcttattatt tctattgtat gtgttaatga tttatgtaa aaatgtaatt       6720 gcttttcatg agtagtatga ataaaattga ttagtttgtg ttttcttgtc tccc            6774
```

<210> SEQ ID NO 71
<211> LENGTH: 6002
<212> TYPE: DNA
<213> ORGANISM: homo sapiens

<400> SEQUENCE: 71

```
gaggaaagga gggggctgga agagagtaaa gggctgttgt taaacagttt cttaccgtaa        60
gagggagttc agacctagat cttttccagtt aatcacacaa caaacttagc tcatcgcaat      120
aaaaagcagc tcagagccga ctggctcttt taggcactga ctccgaacag gattctttca      180
cccaggcatc tcctccagag ggatccgcca gcccgtccag cagcaccatg tgggtgacca      240
aactcctgcc agccctgctg ctgcagcatg tcctcctgca tctcctcctg ctccccatcg      300
ccatccccta tgcagaggga caaggaaaa aagaaatac aattcatgaa ttcaaaaaat         360
cagcaaagac taccctaatc aaaatagatc cagcactgaa gataaaaacc aaaaagtga       420 atactgcaga ccaatgtgct aatagatgta ctaggaataa aggacttcca ttcacttgca      480
```

```
aggcttttgt ttttgataaa gcaagaaaac aatgcctctg gttccccttc aatagcatgt      540
caagtggagt gaaaaagaa tttggccatg aatttgacct ctatgaaaac aaagactaca      600
ttagaaactg catcattggt aaaggacgca gctacaaggg aacagtatct atcactaaga     660
gtggcatcaa atgtcagccc tggagttcca tgataccaca cgaacacagc tttttgcctt     720
cgagctatcg gggtaaagac ctacaggaaa actactgtcg aaatcctcga ggggaagaag     780
ggggaccctg gtgtttcaca agcaatccag aggtacgcta cgaagtctgt gacattcctc     840
agtgttcaga agttgaatgc atgacctgca atggggagag ttatcgaggt ctcatggatc     900
atacagaatc aggcaagatt tgtcagcgct gggatcatca gacaccacac cggcacaaat     960
tcttgcctga aagatatccc gacaagggct tgatgataaa ttattgccgc aatcccgatg    1020
gccagccgag gccatggtgc tatactcttg accctcacac ccgctgggag tactgtgcaa    1080
ttaaaacatg cgctgacaat actatgaatg acactgatgt tcctttggaa acaactgaat    1140
gcatccaagt tcaaggagaa ggctacaggg gcactgtcaa taccatttgg aatggaattc    1200
catgtcagcg ttgggattct cagtatcctc acgagcatga catgactcct gaaaatttca    1260
agtgcaagga cctacgagaa aattactgcc gaaatccaga tgggtctgaa tcaccctggt    1320
gttttaccac tgatccaaac atccgagttg gctactgctc ccaaattcca aactgtgata    1380
tgtcacatgg acaagattgt tatcgtggga atggcaaaaa ttatatgggc aacttatccc    1440
aaacaagatc tggactaaca tgttcaatgt gggacaagaa catggaagac ttacatcgtc    1500
atatcttctg gaaccagat gcaagtaagc tgaatgagaa ttactgccga atccagatg     1560 atgatgctca tggaccctgg tgctacacgg gaaatccact cattccttgg gattattgcc    1620
ctatttctcg ttgtgaaggt gataccacac ctacaatagt caatttagac catcccgtaa    1680
tatcttgtgc caaaacgaaa caattgcgag ttgtaaatgg gattccaaca cgaacaaaca    1740
taggatggat ggttagtttg agatacagaa ataaacatat ctgcggagga tcattgataa    1800
aggagagttg ggttcttact gcacgacagt gttttccctt ctcgagacttg aaagattatg   1860 aagcttggct tggaattcat gatgtccacg gaagaggaga tgagaaatgc aaacaggttc    1920
tcaatgtttc ccagctggta tatggccctg aaggatcaga tctggtttta atgaagcttg    1980
ccaggcctgc tgtcctggat gattttgtta gtacgattga tttacctaat tatggatgca    2040
caattcctga aaagaccagt tgcagtgttt atggctgggg ctacactgga ttgatcaact    2100
atgatggcct attacgagtg gcacatctct atataatggg aaatgagaaa tgcagccagc    2160
atcatcgagg aaggtgact ctgaatgagt ctgaaatatg tgctgggggct gaaaagattg   2220 gatcaggacc atgtgagggg gattatgtg gcccacttgt ttgtgagcaa cataaaatga    2280
gaatggttct tggtgtcatt gttcctggtc gtggatgtgc cattccaaat cgtcctggta    2340
tttttgtccg agtagcatat atgcaaaaat ggatacacaa aattatttta acatataagg    2400
taccacagtc atagctgaag taagtgtgtc tgaagcaccc accaatacaa ctgtctttta    2460
catgaagatt tcagagaatg tggaatttaa aatgtcactt acaacaatcc taagacaact    2520
actggagagt catgtttgtt gaaattctca ttaatgttta tgggtgtttt ctgttgtttt    2580
gtttgtcagt gttattttgt caatgttgaa gtgaattaag gtacatgcaa gtgtaataac    2640
atatctcctg aagatacttg aatggattaa aaaacacac aggtatattt gctggatgat    2700
aaagatttca tggaaaaaa atcaattaa tctgtctaag ctgctttctg atgttggttt      2760
cttaataatg agtaaaccac aaattaaatg ttatttttaac ctcaccaaaa caatttatac    2820
```

```
cttgtgtccc taaattgtag ccctatatta aattatatta catttcatat gctatatgtt    2880
atagttcatt catttctctt caccatgtat cctgcaatac tggtacacga acacactttt    2940
tacaaaacca catacccatg tacacatgcc taggtacaca tgtgcatgca ctacagttta    3000
aattatggtg tacctaatgt aacccctaaa tattttagaa gtatgtacct atagttttac    3060
ctcaaaaaaa ccagaaatct ctaaagacca gtagaaatat taaaaaatga tgcaagatca    3120
aaatgattag ctaattctcc atacataatc tgcagatgat cttctttggt tggcatttca    3180
ggtgtggcca tcacccagag ttaaataaca cctaatctag gtgtttacat gtattcatta    3240
tcctagttat ttcatgtagt ttctaattct taaaggaaag agggtaatag ttctatttgt    3300
gtaatttgtt tcctccaaac ttaaggccac ttatttacac aagatatttg tagatctatt    3360
ttcctaaagc atttcttaag tgctcagatc agtatctaat tgaagaagtt taaaagtgtt    3420
ttggtcatta aaaatgtact taaataggtt aaatctaagc cttgctgctg tgattggctt    3480
ctagctcact gcctttaaat tttaaaaaat ttaagaggaa aatttccaag tctccaaagt    3540
tttataaata cccttcatca agtcatgcat taaagtatat attggagaaa aaaataaaaa    3600
tacttttctc aacctggaag attttagcct aataaagctt ttttgaagta aaagacaact    3660
tgtaaaagga aagaaactag tttgtctcaa ctctgtattc atttattttt tttttgaagt    3720
agagtggaat ctgttgaatc agatatttta tcaagatatg tttattttt cttatttcat    3780
tttacaaagt tcactcctaa tgccatatgt aacagacatt taaattttgt gttctgtata    3840
acagccaaat tatcatattt atcattgtat ttgtcatgct tagctaaaga tcatgtattt    3900
gttgagaaat agaataacaa aaagtaatag gataggcttt gaattttgc agaaatcttc    3960
ctgtacaaaa cacctttaaa aataattttt tgaatggtgt gaatccagta gtcccatttc    4020
tctgacttag ttttcttgag tgattttat caaggccaag tccccaaaca attccctacc    4080
agctctttag agtactgttc aatctggact aaaatggttt taagtttatg gagagcttag    4140
tccacagaat atagggcggc gagtccagaa atgcttatac aattttttt tcataataag    4200
atatgtgctg gcatcaagaa acttaaagtg gaagcaaaaa gacatccaac tagttgctgg    4260
tctctatcat cttatctgat ggtatttcta ttttccttat ataatacacc attttagtaa    4320
gaactcctag aaatttcaag agcatattgc caaaatataa agtatatttc atagtttctt    4380
ctggctgaac cagtgaaatt ttattattgc atattaatga tatttgtaaa acttttataa    4440
aaattgtcat aattttaaat actcacattt taaaaatact tctttaatga ctcttcctct    4500
aaatttcctg gaaatacaga taaagattag ctagatacaa gatacagcta agtatttaga    4560
cattttgagg ctagtatttt tcattttatt aaaggctaaa aacaatacca ccaataaatc    4620
atcaaacaaa ccgtacaaag taattctctc tttgggaggc tcctttcgtg atagagggac    4680
atgggtggaa ttgacaatga aacttagatg aacaaggtcc atgttatttt aggtggtaga    4740
acagggtaga gtcatgtcat tatttgctgg tggaagacac tatttaccag gtgttctttg    4800
ctgaataaat cattaaacat ttttaaaaat ccaacaatcc actttatttt gtgtcattga    4860
caaaaggatc ttttaaatca gaaggtttca atgcaatttt tggtttggct gtttgaataa    4920
tggttatgta ctgttataat tgtagacatt ttctcacgtc taccaggaat tgaagtgtaa    4980
aactaaaata ttttcataa tgcctctgcc gtgcagaagg aatgataatc cttttgtata    5040
cttctttaat tttattgtaa aatgtgtaat gactttacc tatatgctgt gggcaggtcc    5100
tcagtaaaat ctattgagtc aatttctagt attaacaggc ttttgcttgc tatctaagtg    5160
tttcaaatta tgggaagtgt gagacactgg aaggcaagaa aattaacaat aatggcatgt    5220
```

-continued

```
gatagcaaaa ttgtatttca cttattcctg tgaatatttc ttgttggtac caatggtact    5280
gtacaaagtg aatgttatag ccacaacatt ctcttgaaaa gaacactgtc aagaagtggg    5340
aaattgctgt caggcatttc attgttgttt ttaaactttt ttaaaagaaa tactggtttt    5400
gcaatataga gatcatgtgg taaagaattt taataagatc ttatactaaa aagccttaaa    5460
tcaatttatt gagattcaaa aaatactatt ataattaatt acatcccata catataggca    5520
aactcattta aaaataaaa ctaattttgg taaaagtaca tggcctttgt ttttaaaata    5580
cataatttta aaataaatca cttgtcatga taaagtccaa aaagaagtta tcattcaaca    5640
ttcaactaag gttggagcta agaatttact aatacaaaaa aagttaaaat tttttggacc    5700
atatatatct tgacagtgta acttttaagt aggttcattt ccatttgcac agaaagtttc    5760 tgtcttagg aaactgaaaa tgaaatactg tggatgctat gactgtttgt cttgtatgta    5820
aataggaaat taataagctg cctattgagt ggtatagctg tatgcttacc caaaaaggg    5880 aacactgtgg ttatgacttg tattataaac tttctgtagt taataaagtt gttattttta    5940
taaccatgat tatattatta ttattaataa aatatttat caaaatgaaa aaaaaaaaaa    6000
aa                                                                  6002
```

<210> SEQ ID NO 72
<211> LENGTH: 728
<212> TYPE: PRT
<213> ORGANISM: homo sapiens

<400> SEQUENCE: 72

```
Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220
```

```
His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
            245                 250                 255

Asp Asn Tyr Cys Arg Asn Pro Asp Gly Gln Pro Arg Pro Trp Cys Tyr
        260                 265                 270

Thr Leu Asp Pro His Thr Arg Trp Glu Tyr Cys Ala Ile Lys Thr Cys
    275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Ala His
                435                 440                 445

Gly Pro Trp Cys Tyr Thr Gly Asn Pro Leu Ile Pro Trp Asp Tyr Cys
        450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
            485                 490                 495

Asn Gly Ile Pro Thr Arg Thr Asn Ile Gly Trp Met Val Ser Leu Arg
                500                 505                 510

Tyr Arg Asn Lys His Ile Cys Gly Gly Ser Leu Ile Lys Glu Ser Trp
            515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
            565                 570                 575

Ser Asp Leu Val Leu Met Lys Leu Ala Arg Pro Ala Val Leu Asp Asp
        580                 585                 590

Phe Val Ser Thr Ile Asp Leu Pro Asn Tyr Gly Cys Thr Ile Pro Glu
    595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
```

```
                    645                 650                 655
Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
        690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 73
<211> LENGTH: 1369
<212> TYPE: DNA
<213> ORGANISM: homo sapiens

<400> SEQUENCE: 73
gaggaaagga gggggctgga agagagtaaa gggctgttgt taaacagttt cttaccgtaa      60
gagggagttc agacctagat cttttccagtt aatcacacaa caaacttagc tcatcgcaat    120
aaaaagcagc tcagagccga ctggctcttt taggcactga ctccgaacag gattctttca    180
cccaggcatc tcctccagag ggatccgcca gcccgtccag cagcaccatg tgggtgacca    240
aactcctgcc agccctgctg ctgcagcatg tcctcctgca tctcctcctg ctccccatcg    300
ccatccccta tgcagaggga caaggaaaa gaagaaatac aattcatgaa ttcaaaaaat      360
cagcaaagac taccctaatc aaaatagatc cagcactgaa gataaaaacc aaaaaagtga    420
atactgcaga ccaatgtgct aatagatgta ctaggaataa aggacttcca ttcacttgca    480
aggcttttgt ttttgataaa gcaagaaaac aatgcctctg gttccccttc aatagcatgt    540
caagtggagt gaaaaagaa tttggccatg aatttgacct ctatgaaaac aaagactaca    600
ttagaaactg catcattggt aaaggacgca gctacaaggg aacagtatct atcactaaga    660
gtggcatcaa atgtcagccc tggagttcca tgataccaca cgaacacagc ttttttgcctt    720 cgagctatcg gggtaaagac ctacaggaaa actactgtcg aaatcctcga ggggaagaag    780
ggggaccctg gtgtttcaca agcaatccag aggtacgcta cgaagtctgt gacattcctc    840
agtgttcaga agttgaatgc atgaccctgca atggggagag ttatcgaggt ctcatggatc    900
atacagaatc aggcaagatt tgtcagcgct gggatcatca gacaccacac cggcacaaat    960
tcttgcctga aagatatccc gacaagggct ttgatgataa ttattgccgc aatcccgatg   1020
gccagccgag gccatggtgc tatactcttg accctcacac ccgctgggag tactgtgcaa   1080
ttaaaacatg cgagacataa catgggctct caactgatgg tgaacttctt ctggtgagtg   1140
acagaggctg cagtgaagaa taatgagtct aatagaagtt tatcacagat gtctctaatc   1200
tttatagctg atccctacct ctctcgctgt ctttgtaccc agcctgcatt ctgtttcgat   1260
ctgtctttta gcagtccata caatcatttt tctacatgct ggcccttacc tagcttttct   1320
gaatttacaa taaaaactat tttttaacgt gaaaaaaaaa aaaaaaaa                1369

<210> SEQ ID NO 74
<211> LENGTH: 290
<212> TYPE: PRT
<213> ORGANISM: homo sapiens

<400> SEQUENCE: 74
```

Met Trp Val Thr Lys Leu Leu Pro Ala Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Glu Thr
    290

<210> SEQ ID NO 75
<211> LENGTH: 5987
<212> TYPE: DNA
<213> ORGANISM: homo sapiens

<400> SEQUENCE: 75
gaggaaagga gggggctgga agagagtaaa gggctgttgt taaacagttt cttaccgtaa      60
gagggagttc agacctagat cttctccagtt aatcacacaa caaacttagc tcatcgcaat    120
aaaaagcagc tcagagccga ctggctcttt taggcactga ctccgaacag gattctttca    180
cccaggcatc tcctccagag ggatccgcca gcccgtccag cagcaccatg tgggtgacca    240
aactcctgcc agccctgctg ctgcagcatg tcctcctgca tctcctcctg ctccccatcg    300
ccatccccta tgcagaggga caaggaaaa gaagaaatac aattcatgaa ttcaaaaat       360 cagcaaagac tacctaatc aaaatagatc cagcactgaa gataaaaacc aaaaaagtga     420

```
atactgcaga ccaatgtgct aatagatgta ctaggaataa aggacttcca ttcacttgca    480
aggcttttgt ttttgataaa gcaagaaaac aatgcctctg gttccccttc aatagcatgt    540
caagtggagt gaaaaagaa tttggccatg aatttgacct ctatgaaaac aaagactaca     600
ttagaaactg catcattggt aaaggacgca gctacaaggg aacagtatct atcactaaga    660
gtggcatcaa atgtcagccc tggagttcca tgataccaca cgaacacagc tatcggggta    720
aagacctaca ggaaaactac tgtcgaaatc ctcgagggga agaagggga ccctggtgtt     780
tcacaagcaa tccagaggta cgctacgaag tctgtgacat tcctcagtgt tcagaagttg    840
aatgcatgac ctgcaatggg gagagttatc gaggtctcat ggatcataca gaatcaggca    900
agatttgtca gcgctgggat catcagacac cacaccggca caaattcttg cctgaaagat    960
atcccgacaa gggctttgat gataattatt gccgcaatcc cgatggccag ccgaggccat   1020
ggtgctatac tcttgaccct cacacccgct gggagtactg tgcaattaaa acatgcgctg   1080
acaatactat gaatgacact gatgttcctt tggaaacaac tgaatgcatc caaggtcaag   1140
gagaaggcta caggggcact gtcaatacca tttggaatgg aattccatgt cagcgttggg   1200
attctcagta tcctcacgag catgacatga ctcctgaaaa tttcaagtgc aaggacctac   1260
gagaaaatta ctgccgaaat ccagatgggt ctgaatcacc ctggtgtttt accactgatc   1320
caaacatccg agttggctac tgctcccaaa ttccaaactg tgatatgtca catggacaag   1380
attgttatcg tgggaatggc aaaaattata tgggcaactt atcccaaaca agatctggac   1440
taacatgttc aatgtgggac aagaacatgg aagacttaca tcgtcatatc ttctgggaac   1500
cagatgcaag taagctgaat gagaattact gccgaaatcc agatgatgat gctcatggac   1560
cctggtgcta cacgggaaat ccactcattc cttgggatta ttgccctatt tctcgttgtg   1620
aaggtgatac cacacctaca atagtcaatt tagaccatcc cgtaatatct tgtgccaaaa   1680
cgaaacaatt gcgagttgta atgggattc caacacgaac aaacatagga tggatggtta   1740
gtttgagata cagaaataaa catatctgcg gaggatcatt gataaaggag agttgggttc   1800
ttactgcacg acagtgtttc ccttctcgag acttgaaaga ttatgaagct ggcttggaa    1860
ttcatgatgt ccacggaaga ggagatgaga atgcaaaca ggttctcaat gtttcccagc    1920
tggtatatgg ccctgaagga tcagatctgg ttttaatgaa gcttgccagg cctgctgtcc   1980
tggatgattt tgttagtacg attgatttac taattatgg atgcacaatt cctgaaaaga   2040
ccagttgcag tgtttatggc tggggctaca ctggattgat caactatgat ggcctattac   2100
gagtggcaca tctctatata tgggaaatg agaaatgcag ccagcatcat cgagggaagg    2160
tgactctgaa tgagtctgaa atatgtgctg ggctgaaaa gattggatca ggaccatgtg    2220
aggggatta tggtggccca cttgtttgtg agcaacataa aatgagaatg gttcttggtg    2280
tcattgttcc tggtcgtgga tgtgccattc caaatcgtcc tggtatttt gtccgagtag    2340
catattatgc aaaatggata cacaaaatta ttttaacata taaggtacca cagtcatagc    2400
tgaagtaagt gtgtctgaag cacccaccaa tacaactgtc ttttacatga agatttcaga   2460
gaatgtggaa tttaaaatgt cacttacaac aatcctaaga caactactgg agagtcatgt   2520
tgttgaaat tctcattaat gtttatgggt gttttctgtt gttttgtttg tcagtgttat    2580
tttgtcaatg ttgaagtgaa ttaaggtaca tgcaagtgta ataacatatc tcctgaagat   2640
acttgaatgg attaaaaaaa cacacaggta tatttgctgg atgataaaga tttcatggga   2700
aaaaaaatca attaatctgt ctaagctgct ttctgatgtt ggtttcttaa taatgagtaa   2760
accacaaatt aaatgttatt ttaaccctcac caaaacaatt tataccttgt gtccctaaat   2820
```

| | | | |
|---|---|---|---|
| tgtagcccta | tattaaatta | tattacattt catatgctat | atgttatagt tcattcattt | 2880 |
| ctcttcacca | tgtatcctgc | aatactggta cacgaacaca | cttttacaa aaccacatac | 2940 |
| ccatgtacac | atgcctaggt | acacatgtgc atgcactaca | gtttaaatta tggtgtacct | 3000 |
| aatgtaaccc | ctaaatattt | tagaagtatg tacctatagt | tttacctcaa aaaaccaga | 3060 |
| aatctctaaa | gaccagtaga | aatattaaaa aatgatgcaa | gatcaaaatg attagctaat | 3120 |
| tctccataca | taatctgcag | atgatcttct ttggttggca | tttcaggtgt ggccatcacc | 3180 |
| cagagttaaa | taacacctaa | tctaggtgtt tacatgtatt | cattatccta gttatttcat | 3240 |
| gtagttttcta | attcttaaag | gaagagggg aatagttcta | tttgtgtaat ttgtttcctc | 3300 |
| caaacttaag | gccacttatt | tacacaagat atttgtagat | ctattttcct aaagcatttc | 3360 |
| ttaagtgctc | agatcagtat | ctaattgaag aagtttaaaa | gtgttttggt cattaaaaat | 3420 |
| gtacttaaat | aggttaaatc | taagccttgc tgctgtgatt | ggcttctagc tcactgcctt | 3480 |
| taaatttaa | aaaatttaag | aggaaaattt ccaagtctcc | aaagttttat aaatacccctt | 3540 |
| catcaagtca | tgcattaaag | tatatattgg agaaaaaaat | aaaatactt ttctcaacct | 3600 |
| ggaagatttt | agcctaataa | agcttttttg aagtaaaaga | caacttgtaa aaggaaagaa | 3660 |
| actagtttgt | ctcaactctg | tattcattta tttttttttt | gaagtagagt ggaatctgtt | 3720 |
| gaatcagata | ttttatcaag | atatgtttat ttttcttat | ttcatttac aaagttcact | 3780 |
| cctaatgcca | tatgtaacag | acattaaat tttgtgttct | gtataacagc caaattatca | 3840 |
| tatttatcat | tgtatttgtc | atgcttagct aaagatcatg | tatttgttga gaaatagaat | 3900 |
| aacaaaaagt | aataggatag | gctttgaatt tttgcagaaa | tcttcctgta caaacaccct | 3960 |
| ttaaaaataa | tttttgaat | ggtgtgaatc cagtagtccc | atttctctga cttagttttc | 4020 |
| ttgagtgatt | tttatcaagg | ccaagtcccc aaacaattcc | ctaccagctc tttagagtac | 4080 |
| tgttcaatct | ggactaaaat | ggttttaagt ttatggagag | cttagtccac agaatatagg | 4140 |
| gcggcgagtc | cagaaatgct | tatacaattt ttttttcata | ataagatatg tgctggcatc | 4200 |
| aagaaactta | aagtggaagc | aaaaagacat ccaactagtt | gctggtctct atcatcttat | 4260 |
| ctgatggtat | ttctattttc | cttatataat acaccatttt | agtaagaact cctagaaatt | 4320 |
| tcaagagcat | attgccaaaa | tataaagtat atttcatagt | ttcttctggc tgaaccagtg | 4380 |
| aaattttatt | attgcatatt | aatgatattt gtaaaacttt | tataaaaatt gtcataattt | 4440 |
| taaatactca | cattttaaaa | atacttcttt aatgactctt | cctctaaatt tcctggaaat | 4500 |
| acagataaag | attagctaga | tacaagatac agctaagtat | ttagacattt tgaggctagt | 4560 |
| attttttcatt | ttattaaagg | ctaaaacaa taccaccaat | aaatcatcaa acaaaccgta | 4620 |
| caaagtaatt | ctctctttgg | gaggctcctt tcgtgataga | gggacatggg tggaattgac | 4680 |
| aatgaaactt | agatgaacaa | ggtccatgtt attttaggtg | gtagaacagg gtagagtcat | 4740 |
| gtcattattt | gctggtggaa | gacactattt accaggtgtt | ctttgctgaa taaatcatta | 4800 |
| aacattttta | aaaatccaac | aatccacttt attttgtgtc | attgacaaaa ggatctttta | 4860 |
| aatcagaagg | tttcaatgca | attttttggtt tggctgtttg | aataatggtt atgtactgtt | 4920 |
| ataattgtag | acattttctc | acgtctacca ggaattgaag | tgtaaaacta aaatattttt | 4980 |
| cataatgcct | ctgccgtgca | gaaggaatga taatccttt | gtatacttct ttaattttat | 5040 |
| tgtaaaatgt | gtaatgactt | ttacctatat gctgtgggca | ggtcctcagt aaaatctatt | 5100 |
| gagtcaattt | ctagtattaa | caggcttttg cttgctatct | aagtgtttca aattatggga | 5160 |

-continued

```
agtgtgagac actggaaggc aagaaaatta acaataatgg catgtgatag caaaattgta    5220
tttcacttat tcctgtgaat atttcttgtt ggtaccaatg gtactgtaca aagtgaatgt    5280
tatagccaca acattctctt gaaaagaaca ctgtcaagaa gtgggaaatt gctgtcaggc    5340
atttcattgt tgttttaaa cttttttaaa agaaatactg gttttgcaat atagagatca    5400
tgtggtaaag aattttaata agatcttata ctaaaaagcc ttaaatcaat ttattgagat    5460
tcaaaaaata ctattataat taattacatc ccatacatat aggcaaactc atttaaaaaa    5520
taaaactaat tttggtaaaa gtacatggcc tttgtttta aaatacataa ttttaaaata    5580
aatcacttgt catgataaag tccaaaaaga agttatcatt caacattcaa ctaaggttgg    5640
agctaagaat ttactaatac aaaaaaagtt aaaattttt ggaccatata tatcttgaca    5700
gtgtaacttt taagtaggtt catttccatt tgcacagaaa gtttctgtct ttaggaaact    5760
gaaaatgaaa tactgtggat gctatgactg tttgtcttgt atgtaaatag gaaattaata    5820
agctgcctat tgagtggtat agctgtatgc ttacccaaaa aagggaacac tgtggttatg    5880
acttgtatta taaactttct gtagttaata aagttgttat ttttataacc atgattatat    5940
tattattatt aataaaatat tttatcaaaa tgaaaaaaaa aaaaaaa                  5987
```

<210> SEQ ID NO 76  
<211> LENGTH: 723  
<212> TYPE: PRT  
<213> ORGANISM: homo sapiens

<400> SEQUENCE: 76

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
    210                 215                 220

Lys Ile Cys Gln Arg Trp Asp His Gln Thr Pro His Arg His Lys Phe
```

-continued

```
            225                 230                 235                 240
        Leu Pro Glu Arg Tyr Pro Asp Lys Gly Phe Asp Asp Asn Tyr Cys Arg
                        245                 250                 255

Asn Pro Asp Gly Gln Pro Arg Pro Trp Cys Tyr Thr Leu Asp Pro His
                        260                 265                 270

Thr Arg Trp Glu Tyr Cys Ala Ile Lys Thr Cys Ala Asp Asn Thr Met
                        275                 280                 285

Asn Asp Thr Asp Val Pro Leu Glu Thr Thr Glu Cys Ile Gln Gly Gln
                290                 295                 300

Gly Glu Gly Tyr Arg Gly Thr Val Asn Thr Ile Trp Asn Gly Ile Pro
        305                 310                 315                 320

Cys Gln Arg Trp Asp Ser Gln Tyr Pro His Glu His Asp Met Thr Pro
                        325                 330                 335

Glu Asn Phe Lys Cys Lys Asp Leu Arg Glu Asn Tyr Cys Arg Asn Pro
                        340                 345                 350

Asp Gly Ser Glu Ser Pro Trp Cys Phe Thr Thr Asp Pro Asn Ile Arg
                        355                 360                 365

Val Gly Tyr Cys Ser Gln Ile Pro Asn Cys Asp Met Ser His Gly Gln
                370                 375                 380

Asp Cys Tyr Arg Gly Asn Gly Lys Asn Tyr Met Gly Asn Leu Ser Gln
        385                 390                 395                 400

Thr Arg Ser Gly Leu Thr Cys Ser Met Trp Asp Lys Asn Met Glu Asp
                        405                 410                 415

Leu His Arg His Ile Phe Trp Glu Pro Asp Ala Ser Lys Leu Asn Glu
                        420                 425                 430

Asn Tyr Cys Arg Asn Pro Asp Asp Ala His Gly Pro Trp Cys Tyr
                        435                 440                 445

Thr Gly Asn Pro Leu Ile Pro Trp Asp Tyr Cys Pro Ile Ser Arg Cys
                450                 455                 460

Glu Gly Asp Thr Thr Pro Thr Ile Val Asn Leu Asp His Pro Val Ile
        465                 470                 475                 480

Ser Cys Ala Lys Thr Lys Gln Leu Arg Val Val Asn Gly Ile Pro Thr
                        485                 490                 495

Arg Thr Asn Ile Gly Trp Met Val Ser Leu Arg Tyr Arg Asn Lys His
                        500                 505                 510

Ile Cys Gly Gly Ser Leu Ile Lys Glu Ser Trp Val Leu Thr Ala Arg
                        515                 520                 525

Gln Cys Phe Pro Ser Arg Asp Leu Lys Asp Tyr Glu Ala Trp Leu Gly
                530                 535                 540

Ile His Asp Val His Gly Arg Gly Asp Glu Lys Cys Lys Gln Val Leu
        545                 550                 555                 560

Asn Val Ser Gln Leu Val Tyr Gly Pro Glu Gly Ser Asp Leu Val Leu
                        565                 570                 575

Met Lys Leu Ala Arg Pro Ala Val Leu Asp Asp Phe Val Ser Thr Ile
                        580                 585                 590

Asp Leu Pro Asn Tyr Gly Cys Thr Ile Pro Glu Lys Thr Ser Cys Ser
                        595                 600                 605

Val Tyr Gly Trp Gly Tyr Thr Gly Leu Ile Asn Tyr Asp Gly Leu Leu
                610                 615                 620

Arg Val Ala His Leu Tyr Ile Met Gly Asn Glu Lys Cys Ser Gln His
        625                 630                 635                 640

His Arg Gly Lys Val Thr Leu Asn Glu Ser Glu Ile Cys Ala Gly Ala
                        645                 650                 655
```

```
Glu Lys Ile Gly Ser Gly Pro Cys Glu Gly Asp Tyr Gly Gly Pro Leu
            660                 665                 670

Val Cys Glu Gln His Lys Met Arg Met Val Leu Gly Val Ile Val Pro
        675                 680                 685

Gly Arg Gly Cys Ala Ile Pro Asn Arg Pro Gly Ile Phe Val Arg Val
    690                 695                 700

Ala Tyr Tyr Ala Lys Trp Ile His Lys Ile Ile Leu Thr Tyr Lys Val
705                 710                 715                 720

Pro Gln Ser

<210> SEQ ID NO 77
<211> LENGTH: 1354
<212> TYPE: DNA
<213> ORGANISM: homo sapiens

<400> SEQUENCE: 77
gaggaaagga gggggctgga agagagtaaa gggctgttgt taaacagttt cttaccgtaa      60
gagggagttc agacctagat cttccagtt aatcacacaa caaacttagc tcatcgcaat     120
aaaaagcagc tcagagccga ctggctcttt taggcactga ctccgaacag gattctttca     180
cccaggcatc tcctccagag ggatccgcca gcccgtccag cagcaccatg tgggtgacca     240
aactcctgcc agccctgctg ctgcagcatg tcctcctgca tctcctcctg ctccccatcg     300
ccatccccta tgcagaggga caaggaaaa gaagaaatac aattcatgaa ttcaaaaaat     360
cagcaaagac taccctaatc aaaatagatc cagcactgaa gataaaaacc aaaaaagtga     420
atactgcaga ccaatgtgct aatagatgta ctaggaataa aggacttcca ttcacttgca     480
aggcttttgt ttttgataaa gcaagaaaac aatgcctctg gttcccctc aatagcatgt     540
caagtggagt gaaaaagaa tttggccatg aatttgacct ctatgaaaac aaagactaca     600
ttagaaactg catcattggt aaaggacgca gctacaaggg aacagtatct atcactaaga     660
gtggcatcaa atgtcagccc tggagttcca tgataccaca cgaacacagc tatcggggta     720
aagacctaca ggaaaactac tgtcgaaatc ctcgagggga agaagggga ccctggtgtt     780
tcacaagcaa tccagaggta cgctacgaag tctgtgacat tcctcagtgt tcagaagttg     840
aatgcatgac ctgcaatggg gagagttatc gaggtctcat ggatcataca gaatcaggca     900
agatttgtca gcgctgggat catcagacac acaccggca caattcttg cctgaaagat     960
atcccgacaa gggctttgat gataattatt gccgcaatcc cgatggccag ccgaggccat    1020
ggtgctatac tcttgaccct cacacccgct gggagtactg tgcaattaaa acatgcgaga    1080
cataacatgg gctctcaact gatggtgaac ttcttctggt gagtgacaga ggctgcagtg    1140
aagaataatg agtctaatag aagtttatca cagatgtctc taatctttat agctgatccc    1200
tacctctctc gctgtctttg tacccagcct gcattctgtt tcgatctgtc ttttagcagt    1260
ccatacaatc attttctac atgctggccc ttacctagct tttctgaatt tacaataaaa    1320
actattttt aacgtgaaaa aaaaaaaaaaa aaaa                                1354

<210> SEQ ID NO 78
<211> LENGTH: 285
<212> TYPE: PRT
<213> ORGANISM: homo sapiens

<400> SEQUENCE: 78

Met Trp Val Thr Lys Leu Leu Pro Ala Leu Leu Leu Gln His Val Leu
1               5                   10                  15
```

```
Leu His Leu Leu Leu Pro Ile Ala Ile Pro Tyr Ala Glu Gly Gln
         20                  25                  30

Arg Lys Arg Arg Asn Thr Ile His Glu Phe Lys Lys Ser Ala Lys Thr
     35                  40                  45

Thr Leu Ile Lys Ile Asp Pro Ala Leu Lys Ile Lys Thr Lys Lys Val
 50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Glu Thr
        275                 280                 285

<210> SEQ ID NO 79
<211> LENGTH: 2102
<212> TYPE: DNA
<213> ORGANISM: homo sapiens

<400> SEQUENCE: 79
gaggaaagga gggggctgga agagagtaaa gggctgttgt taaacagttt cttaccgtaa      60
gagggagttc agacctagat ctttccagtt aatcacacaa caaacttagc tcatcgcaat     120
aaaaagcagc tcagagccga ctggctcttt taggcactga ctccgaacag gattctttca     180
cccaggcatc tcctccagag ggatccgcca gcccgtccag cagcaccatg tgggtgacca     240
aactcctgcc agccctgctg ctgcagcatg tcctcctgca tctcctcctg ctccccatcg     300
ccatccccta tgcagaggga caaggaaaa gaagaaatac aattcatgaa ttcaaaaaat      360
cagcaaagac taccctaatc aaaatagatc cagcactgaa gataaaaacc aaaaagtga     420 atactgcaga ccaatgtgct aatagatgta ctaggaataa aggcttcca ttcacttgca      480 aggcttttgt ttttgataaa gcaagaaaac aatgcctctg gttccccttc aatagcatgt     540
caagtggagt gaaaaagaa tttggccatg aatttgacct ctatgaaaac aaagactaca     600
```

```
ttagaaactg catcattggt aaaggacgca gctacaaggg aacagtatct atcactaaga      660
gtggcatcaa atgtcagccc tggagttcca tgataccaca cgaacacagc tttttgcctt      720
cgagctatcg gggtaaagac ctacaggaaa actactgtcg aaatcctcga ggggaagaag      780
ggggaccctg tgtttcaca agcaatccag aggtacgcta cgaagtctgt gacattcctc       840
agtgttcaga aggtaaataa acctgaatgc catgtgggcc attctattcc ccctatgtgt      900
agaactgtaa ctcacattaa aggttaacag caacgaatca atcataacaa atatgttgtt      960
cgtgcaaatg caactacaaa taattattta acattttta tacaatgttt ttaaaactgt      1020
tggattatca ccagattaat gcaaaataac agagcgagtt atcagtttga atttcaacac     1080
tgcctgagac atccctctgg ggaaagtgaa agagagggtt tacttaccta ctgtcttgag     1140
ctcacatacc tcaaaatcta ctactgtgtg cacctgaaa ggagttgaat gaagcttagc      1200
ctttcattag caatgttaat tctattcaac cagcacctgc ttccacagaa attctgtcca     1260
aactatcatg aagtggtgtg acaagggtat atggacccag aagataatac aatataagaa     1320
gggatcactg gaagcttgac cccatgcaca ttttggtgaa aatgtgccta gaatcaaatg     1380
tgacacgtag gctggaactg agtaccattc agaataggat ctgaagagat caaagcaatg     1440
gagaccacca aactgtcttg aaggcatgtc tatggacctt aagtccatgt ctatgttttc     1500
agctcttctc acagcataaa agggcattgt ccttactttt gcagtggaaa actgaatggc     1560
tgacaagatg gaagagtaac catttcagca ttgtatgtgg tttcattttt cttagttatc     1620
tggctactga atagccggat ttttcagttc tgtcagaaac tctaaatttc caaaatcta     1680
agtgaaacat ggatgaaact ctgttagaaa attgttagga ttttggagta tttggggagg     1740
gggactactg gaatgctgtc caagttttat actaagatat cttacctgtt tgttattaac     1800
caaatatttt taaaaatatt tcctccataa atattcattt aatattaggt tgatatttat     1860
cacataaaaa gtaaaggcta ctgttagcta attgtcacag agaaggattt gttttctgtt     1920
gttagtgaat ttgaaatcct tgactttatg tgctacagcc agttccatct ctgtttgtaa     1980
attcttactt tccattccat atcatattct gttccctata acctcttcat tgttttctttt    2040
tcttttaaaa ataataaact tttctatgat caaaaaaaaa aaaaaaaaa aaaaaaaaa      2100
aa                                                                    2102
```

<210> SEQ ID NO 80
<211> LENGTH: 210
<212> TYPE: PRT
<213> ORGANISM: homo sapiens

<400> SEQUENCE: 80

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95
```

```
Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Gly Lys
    210

<210> SEQ ID NO 81
<211> LENGTH: 469
<212> TYPE: DNA
<213> ORGANISM: homo sapiens

<400> SEQUENCE: 81
agccctccag gacaggctgc atcagaagag gccatcaagc agatcactgt ccttctgcca      60
tggccctgtg gatgcgcctc ctgccctgc tggcgctgct ggccctctgg ggacctgacc      120
cagccgcagc ctttgtgaac caacacctgt gcggctcaca cctggtggaa gctctctacc      180
tagtgtgcgg ggaacgaggc ttcttctaca cacccaagac ccgccgggag gcagaggacc      240
tgcaggtggg gcaggtggag ctgggcgggg gccctggtgc aggcagcctg cagcccttgg      300
ccctggaggg gtccctgcag aagcgtggca ttgtggaaca atgctgtacc agcatctgct      360
ccctctacca gctggagaac tactgcaact agacgcagcc cgcaggcagc ccacacccg      420 ccgcctcctg caccgagaga gatggaataa agcccttgaa ccagcaaaa                 469

<210> SEQ ID NO 82
<211> LENGTH: 110
<212> TYPE: PRT
<213> ORGANISM: homo sapiens

<400> SEQUENCE: 82

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 83
```

<211> LENGTH: 495
<212> TYPE: DNA
<213> ORGANISM: homo sapiens

<400> SEQUENCE: 83

```
agccctccag  dacaggctgc  atcagaagag  gccatcaagc  aggtctgttc  caagggcctt    60
tgcgtcagat  cactgtcctt  ctgccatggc  cctgtggatg  cgcctcctgc  ccctgctggc   120
gctgctggcc  ctctggggac  ctgacccagc  cgcagccttt  gtgaaccaac  acctgtgcgg   180
ctcacacctg  gtggaagctc  tctacctagt  gtgcggggaa  cgaggcttct  tctacacacc   240
caagacccgc  cggaggcag   aggacctgca  ggtggggcag  gtggagctgg  gcggggggccc  300
tggtgcaggc  agcctgcagc  ccttggccct  ggaggggtcc  ctgcagaagc  gtggcattgt   360
ggaacaatgc  tgtaccagca  tctgctccct  ctaccagctg  gagaactact  gcaactagac   420
gcagcccgca  ggcagcccca  cacccgccgc  ctcctgcacc  gagagagatg  gaataaagcc   480
cttgaaccag  caaaa                                                         495
```

<210> SEQ ID NO 84
<211> LENGTH: 110
<212> TYPE: PRT
<213> ORGANISM: homo sapiens

<400> SEQUENCE: 84

```
Met Ala Leu Trp Met Arg Leu Leu Pro Leu Leu Ala Leu Leu Ala Leu
1               5                   10                  15
Trp Gly Pro Asp Pro Ala Ala Ala Phe Val Asn Gln His Leu Cys Gly
            20                  25                  30
Ser His Leu Val Glu Ala Leu Tyr Leu Val Cys Gly Glu Arg Gly Phe
        35                  40                  45
Phe Tyr Thr Pro Lys Thr Arg Arg Glu Ala Glu Asp Leu Gln Val Gly
    50                  55                  60
Gln Val Glu Leu Gly Gly Gly Pro Gly Ala Gly Ser Leu Gln Pro Leu
65                  70                  75                  80
Ala Leu Glu Gly Ser Leu Gln Lys Arg Gly Ile Val Glu Gln Cys Cys
                85                  90                  95
Thr Ser Ile Cys Ser Leu Tyr Gln Leu Glu Asn Tyr Cys Asn
            100                 105                 110
```

<210> SEQ ID NO 85
<211> LENGTH: 648
<212> TYPE: DNA
<213> ORGANISM: homo sapiens

<400> SEQUENCE: 85

```
agccctccag  gacaggctgc  atcagaagag  gccatcaagc  aggtctgttc  caagggcctt    60
tgcgtcaggt  gggctcagga  ttccagggtg  gctggacccc  aggccccagc  tctgcagcag   120
ggaggacgtg  gctgggctcg  tgaagcatgt  ggggtgagc   ccaggggccc  caaggcaggg   180
cacctggcct  tcagcctgcc  tcagccctgc  ctgtctccca  gatcactgtc  cttctgccat   240
ggccctgtgg  atgcgcctcc  tgcccctgct  ggcgctgctg  gccctctggg  gacctgaccc   300
agccgcagcc  tttgtgaacc  aacacctgtg  cggctcacac  ctggtggaag  ctctctacct   360
agtgtgcggg  gaacgaggct  tcttctacac  acccaagacc  cgccgggagg  cagaggacct   420
gcaggtgggg  caggtggagc  tgggcggggg  ccctggtgca  ggcagcctgc  agcccttggc   480
cctggagggg  tccctgcaga  agcgtggcat  tgtggaacaa  tgctgtacca  gcatctgctc   540
```

```
cctctaccag ctggagaact actgcaacta gacgcagccc gcaggcagcc ccacacccgc      600
cgcctcctgc accgagagag atggaataaa gcccttgaac cagcaaaa                   648
```

<210> SEQ ID NO 86
<211> LENGTH: 110
<212> TYPE: PRT
<213> ORGANISM: homo sapiens

<400> SEQUENCE: 86

```
Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

<210> SEQ ID NO 87
<211> LENGTH: 529
<212> TYPE: DNA
<213> ORGANISM: homo sapiens

<400> SEQUENCE: 87

```
agccctccag gacaggctgc atcagaagag gccatcaagc aggtctgttc caagggcctt      60
tgcgtcaggt gggctcagga ttccagggtg gctggacccc agatcactgt ccttctgcca      120
tggccctgtg gatgcgcctc ctgcccctgc tggcgctgct ggccctctgg ggacctgacc      180
cagccgcagc ctttgtgaac caacacctgt gcggctcaca cctggtggaa gctctctacc      240
tagtgtgcgg ggaacgaggc ttcttctaca cacccaagac ccgccgggag gcagaggacc      300
tgcaggtggg gcaggtggag ctgggcgggg gccctggtgc aggcagcctg cagcccttgg      360
ccctggaggg gtccctgcag aagcgtggca ttgtggaaca atgctgtacc agcatctgct      420
ccctctacca gctggagaac tactgcaact agacgcagcc gcaggcagc cccacacccg       480 ccgcctcctg caccgagaga gatggaataa agcccttgaa ccagcaaaa                  529
```

<210> SEQ ID NO 88
<211> LENGTH: 70
<212> TYPE: PRT
<213> ORGANISM: homo sapiens

<400> SEQUENCE: 88

```
Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60
```

```
Gln Val Glu Leu Gly Gly
 65                  70
```